US008222375B2

(12) United States Patent
Terrett et al.

(10) Patent No.: US 8,222,375 B2
(45) Date of Patent: Jul. 17, 2012

(54) HUMAN MONOCLONAL ANTIBODIES TO PROTEIN TYROSINE KINASE 7 (PTK7) AND METHODS FOR USING ANTI-PTK7 ANTIBODIES

(75) Inventors: Jonathan Alexander Terrett, Sunnyvale, CA (US); Li-Sheng Lu, Mountain View, CA (US); Chin Pan, Los Altos, CA (US)

(73) Assignee: MEDAREX, Inc., Princeton, NJ (US)

( * ) Notice: Subject to any disclaimer, the term of this patent is extended or adjusted under 35 U.S.C. 154(b) by 818 days.

(21) Appl. No.: 12/095,986

(22) PCT Filed: Dec. 8, 2006

(86) PCT No.: PCT/US2006/046837
§ 371 (c)(1),
(2), (4) Date: Nov. 14, 2008

(87) PCT Pub. No.: WO2007/067730
PCT Pub. Date: Jun. 14, 2007

(65) Prior Publication Data
US 2010/0034826 A1 Feb. 11, 2010

Related U.S. Application Data

(60) Provisional application No. 60/748,373, filed on Dec. 8, 2005.

(51) Int. Cl.
*C07K 16/40* (2006.01)
*C07K 16/00* (2006.01)
*A61K 39/395* (2006.01)
(52) U.S. Cl. ............ 530/388.26; 530/388.15; 530/388.1; 530/387.1; 424/146.1; 424/141.1; 424/130.1
(58) Field of Classification Search .................. None
See application file for complete search history.

(56) References Cited

U.S. PATENT DOCUMENTS

| 2005/0047996 | A1 | 3/2005 | Vogelstein et al. |
| 2006/0019256 | A1 | 1/2006 | Clarke et al. |
| 2006/0147478 | A1 | 7/2006 | Terrett |
| 2006/0166214 | A1 | 7/2006 | Kato et al. |
| 2007/0015163 | A1 | 1/2007 | Isogai et al. |
| 2007/0202107 | A1 | 8/2007 | Whyte et al. |
| 2007/0212352 | A1 | 9/2007 | McPherson et al. |

FOREIGN PATENT DOCUMENTS

| WO | WO-9637610 | 11/1996 |
| WO | WO-9845708 | 10/1998 |
| WO | WO-02059377 | 8/2002 |
| WO | WO-02086443 | 10/2002 |
| WO | WO-03003906 | 1/2003 |
| WO | WO-03025138 | 3/2003 |
| WO | WO-03031930 | 4/2003 |
| WO | WO-03042661 | 5/2003 |
| WO | WO-2004006838 | 1/2004 |
| WO | WO-2004017992 | 3/2004 |
| WO | WO-2004081174 | 9/2004 |
| WO | WO-2005005601 | 1/2005 |
| WO | WO-2005117941 | 12/2005 |
| WO | WO-2006002203 | 1/2006 |
| WO | WO-2006110593 | 10/2006 |
| WO | 2007/038658 A2 | 4/2007 |

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428).*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Bioslide Technologies, "PTKY monoclonal antibody (M02), clone 4C6," retrieved online at: http://www.bioslide.com/product_detail.asp?CartID-BIO@D8LJYEUPNU6HVNTB6QSFSW2 (2007).
Easty, David J. et al., "Loss of Expression of Receptor Tyrosine Kinase Family Genes PTKY and SEK in Metastatic Melanoma," Int. J. Cancer, vol. 71:1061-1065 (1997).
Jung, Jae-Won et al., "Organization of the human PTK7 gene encoding a receptor protein tyrosine kinase-like molecule and alternative splicing of its mRNA," Biochimica et Biophysica Acta, vol. 1579:153-163 (2002).
Kobus, Felix J. et al., "The GxxxG-Containing Transmembrane Domain of the CCK4 Oncogene Does Not Encode Preferential Self-Interaction," Biochemistry, vol. 44:1464-1470 (2005).
Kyriakos, Raymond J. et al., "The Fate of Antibodies Bound to the Surface of Tumor Cells in Vitro," Cancer Research, vol. 52:835-842 (1992).
Lu, Xiaowei et al., "PTK7/CCK-4 is a novel regulator of planar cell polarity in vertebrates," Nature, vol. 430:93-98 (2004). Mossie, Kevin et al., "Colon carcinoma kinase-4 defines a new subclass of the receptor tyrosine kinase family," Oncogene, vol. 11:2179-2184 (1995).
Park, Sang-Kyu et al., "Characterization of the Human Full-Length PTK7 cDNA Encoding a Receptor Protein Kinase-Like Molecule Closely Related to Chick KLG," J. Biochem., vol. 119:235-239 (1996).
Shih, Lisa B. et al., "The Processing and Fate of Antibodies and Their Radiolabels Bound to the Surface of Tumor Cells In Vitro: A Comparison of Nine Radiolabels," J. Nucl. Med., vol. 35:899-908 (1994).
International Preliminary Report on Patentability and Written Opinion for Application No. PCT/US2006/046837, dated Jun. 11, 2008.
International Search Report for Application No. PCT/US2006/046837, dated Sep. 4, 2007.

* cited by examiner

*Primary Examiner* — Sharon Wen
(74) *Attorney, Agent, or Firm* — Nelson Mullins Riley & Scarborough LLP; Jane E. Remillard, Esq.; Jill Gorny Sloper, Esq.

(57) ABSTRACT

The present invention provides isolated monoclonal antibodies, particularly human monoclonal antibodies, that specifically bind to PTK7 with high affinity. Nucleic acid molecules encoding the antibodies of the invention, expression vectors, host cells and methods for expressing the antibodies of the invention are also provided. Immunoconjugates, bispecific molecules and pharmaceutical compositions comprising the antibodies of the invention are also provided. The invention also provides methods for detecting PTK7, as well as methods for treating various diseases, including cancer and infectious diseases, using anti-PTK7 antibodies.

9 Claims, 32 Drawing Sheets

```
Anti-PTK7 3G8 VH
  V segment:  3-30.3
  D segment:  undetermined
  J segment:  JH4b Q   V   Q   L   V   E   S   G   G   G   V   V   Q   P   G   R   S   L
  1   CAG GTG CAG CTG GTG GAG TCT GGG GGA GGC GTG GTC CAG CCT GGG AGG TCC CTG R   L   S   C   A   A   S   G   F   I   F   S   N   Y   A   M   H   W
 55   CGA CTC TCC TGT GCA GCC TCT GGA TTC ATC TTC AGT AAC TAT GCT ATG CAC TGG
                                               ~~~~~~~~~~~~~~~~~~~~~~~~~~~~~~
                                                            CDR1

V   R   Q   A   P   G   K   G   L   E   W   V   A   V   I   S   Y   D
109   GTC CGC CAG GCT CCA GGC AAG GGG CTG GAG TGG GTG GCA GTT ATA TCA TAT GAT
                                                           ~~~~~~~~~~~~~~~~~~
                                                                   CDR2

G   N   N   K   Y   Y   A   D   S   V   K   G   R   F   T   I   S   R
163   GGA AAC AAT AAA TAC TAC GCA GAC TCC GTG AAG GGC CGA TTC ACC ATC TCC AGA
      ~~~~~~~~~~~~
        CDR2

D   N   S   K   N   T   L   Y   L   Q   M   N   S   L   R   A   E   D
217   GAC AAT TCC AAG AAC ACG CTG TAT CTG CAA ATG AAC AGC CTG AGA GCT GAG GAC

T   A   V   Y   Y   C   A   R   E   V   W   S   I   D   N   W   G   Q
271   ACG GCT GTG TAT TAC TGT GCG AGA GAG GTC TGG AGT ATT GAC AAC TGG GGC CAG
                                      ~~~~~~~~~~~~~~~~~~~~~~~~~~~~
                                                CDR3

G   T   L   V   T   V   S   S
325   GGA ACC CTG GTC ACC GTC TCC TCA
```

Fig. 1A

Anti-PTK7 3G8 VK
  V segment: L15
  J segment: JK1

```
      D   I   Q   M   T   Q   S   P   S   S   L   S   A   S   V   G   D   R
1     GAC ATC CAG ATG ACC CAG TCT CCA TCC TCA CTG TCT GCA TCT GTA GGA GAC AGA
                                                            CDR1
                                                  ~~~~~~~~~~~~~~~~~~~~~~~~~~
      V   T   I   T   C   R   A   S   Q   G   I   S   S   W   L   A   W   Y
55    GTC ACC ATC ACT TGT CGG GCG AGT CAG GGT ATT AGC AGC TGG TTA GCC TGG TAT
      ~~~~~~~~~~~~~~~~~~~~~~~~~~~~~~~~~~~~~~~~~~~~~~~~~~~~~~~~~~~~~~
                                                               CDR2
                                                       ~~~~~~~~~~~~~~~~~~~~~~
      Q   Q   K   P   E   K   A   P   K   S   L   I   Y   A   A   S   S   L
109   CAG CAG AAA CCA GAG AAA GCC CCT AAG TCC CTG ATC TAT GCA GCA TCC AGT TTG
      CDR2
      ~~~~~
      Q   S   G   V   P   S   R   F   S   G   S   G   S   G   T   D   F   T
163   CAA AGT GGG GTC CCA TCA AGG TTC AGC GGC AGT GGA TCT GGG ACA GAT TTC ACT
                                                                     CDR3
                                                             ~~~~~~~~~~~~~~~~
      L   T   I   S   S   L   Q   P   E   D   F   A   T   Y   Y   C   Q   Q
217   CTC ACC ATC AGC AGC CTG CAG CCT GAA GAT TTT GCA ACT TAT TAC TGC CAA CAG
           CDR3
      ~~~~~~~~~~~~~~~~~~~~~~~~~~~~~~~~~~
      Y   N   S   Y   P   R   T   F   G   Q   G   T   K   V   E   I   K
271   TAT AAT AGT TAC CCT CGG ACG TTC GGC CAA GGG ACC AAG GTG GAA ATC AAA
```

Fig. 1B

Anti-PTK7 3G8a VK
V segment: L15
J segment: JK3

```
      D   I   Q   M   T   Q   S   P   S   S   L   S   A   S   V   G   D   R
  1   GAC ATC CAG ATG ACC CAG TCT CCA TCC TCA CTG TCT GCA TCT GTA GGA GAC AGA
                                      ~~~~~~~~~~~~~~~~~~~~~~~~~~~~~~~~~~~~~~
                                                     CDR1
      V   T   I   T   C   R   A   S   Q   G   I   S   S   W   L   A   W   Y
 55   GTC ACC ATC ACT TGT CGG GCG AGT CAG GGT ATT AGC AGC TGG TTA GCC TGG TAT
      ~~~~~~~~~~~~~~~~~                                    ~~~~~~~~~~~~~~~~~
                                                                    CDR2
      Q   Q   K   P   E   K   A   P   K   S   L   I   Y   A   A   S   S   L
109   CAG CAG AAA CCA GAG AAG GCC CCT AAG TCC CTG ATC TAT GCT GCA TCC AGT TTG
      ~~~~~~~~~~~~~~~~~~~~~~~~~~~~~~~~~~~~~~~~~~~~~
            CDR2
      Q   S   G   V   P   S   R   F   S   G   S   G   S   G   T   D   F   T
163   CAA AGT GGG GTC CCA TCA AGG TTC AGC GGC AGT GGA TCT GGG ACA GAT TTC ACT
                                                                          ~~~
                                                                          CDR3
      L   T   I   S   S   L   Q   P   E   D   F   A   T   Y   Y   C   Q   Q
217   CTC ACC ATC AGC AGC CTG CAG CCT GAA GAT TTT GCA ACT TAT TAC TGC CAA CAG
      ~~~~~~~~~~~~~~~~~~~~~~~~~~~~~~~~~~~~~~~~~~~~~~~~~~~~~~~~~~~~~~~~~~~~~~
                              CDR3
      Y   N   S   Y   P   F   T   F   G   P   G   T   K   V   D   I   K
271   TAT AAT AGT TAC CCA TTC ACT TTC GGC CCT GGG ACC AAA GTG GAT ATC AAA
```

Fig. 1C

Anti-PTK7 4D5 VH
V segment: 3-30.3
D segment: undetermined
J segment: JH4b

```
  1  Q   V   Q   L   V   E   S   G   G   G   V   V   Q   P   G   R   S   L
     CAG GTG CAG CTG GTG GAG TCT GGG GGA GGC GTG GTC CAG CCT GGG AGG TCC CTG

55  R   L   S   C   A   A   S   G   F   T   F   S   S   Y   A   F   H   W
     AGA CTC TCC TGT GCA GCC TCT GGA TTC ACC TTC AGT AGC TAT GCT TTC CAC TGG
                                                        ~~~~~~~~~~~~~~~~~~~~
                                                                CDR1

109  V   R   Q   A   P   G   K   G   L   E   W   V   A   V   I   S   Y   D
     GTC CGC CAG GCT CCA GGC AAG GGG CTG GAG TGG GTG GCA GTT ATA TCA TAT GAT
                                                        ~~~~~~~~~~~~~~~~~~~~
163  G   S   I   K   Y   Y   A   D   S   V   K   G   R   F   T   I   S   R
     GGA AGC ATT AAA TAC TAC GCA GAC TCC GTG AAG GGC CGA TTC ACC ATC TCC AGA
     ~~~~~~~~~~~~~~~~~~~~
             CDR2

217  D   N   S   K   N   T   L   Y   L   Q   M   N   S   L   R   A   E   D
     GAC AAT TCC AAG AAC ACG CTG TAT CTG CAA ATG AAC AGC CTG AGA GCT GAG GAC

271  T   A   V   Y   Y   C   A   R   T   Y   Y   F   D   Y   W   G   Q   G
     ACG GCT GTG TAT TAC TGT GCG AGG ACG TAC TAC TTT GAC TAC TGG GGC CAG GGA
                                 ~~~~~~~~~~~~~~~~~~~~~~~~~~~~~~~~
                                           CDR3

325  T   L   V   T   V   S   S
     ACC CTG GTC ACC GTC TCC TCA
```

Fig. 2A

Anti-PTK7 4D5 VK
V segment: A10
J segment: JK5

```
1    E   I   V   L   T   Q   S   P   D   F   Q   S   V   T   P   K   E   K
     GAA ATT GTG CTG ACT CAG TCT CCA GAC TTT CAG TCT GTG ACT CCA AAG GAG AAA

55   V   T   I   T   C   R   A   S   Q   S   I   G   S   S   L   H   W   Y
     GTC ACC ATC ACC TGC CGG GCC AGT CAG AGC ATT GGT AGT AGC TTA CAC TGG TAC
                             CDR1

109  Q   Q   K   P   D   Q   S   P   K   L   L   I   K   Y   A   S   Q   S
     CAG CAG AAA CCA GAT CAG TCT CCA AAG CTC CTC ATC AAG TAT GCT TCC CAG TCC
                     CDR2                                CDR2

163  F   S   G   V   P   S   R   F   S   G   S   G   S   G   T   D   F   T
     TTC TCA GGG GTC CCC TCG AGG TTC AGT GGC AGT GGA TCT GGG ACA GAT TTC ACC

217  L   T   I   N   S   L   E   A   E   D   A   A   A   Y   Y   C   H   Q
     CTC ACC ATC AAT AGC CTG GAA GCT GAA GAT GCT GCA GCG TAT TAC TGT CAT CAG

271  S   S   S   L   P   I   T   F   G   Q   G   T   R   L   E   I   K
     AGT AGT AGT TTA CCG ATC ACC TTC GGC CAA GGG ACA CGA CTG GAG ATT AAA
           CDR3
```

Fig. 2B

Anti-PTK7 12C6 VH
V segment:    DP-44
D segment:    undetermined
J segment:    JH4b

```
      E   V   Q   L   V   Q   S   G   G   G   L   V   H   P   G   G   S   L
  1   GAG GTT CAG CTG GTG CAG TCT GGG GGA GGC TTG GTA CAT CCT GGG GGG TCC CTG

R   L   S   C   A   G   S   G   F   T   F   S   T   Y   L   M   Y   W
                                                            ~~~~~~~~~~~~~~~~~
 55   AGA CTC TCC TGT GCA GGC TCT GGA TTC ACC TTC AGT ACC TAT CTT ATG TAC TGG
                                                                 CDR1

V   R   Q   A   P   G   K   T   L   E   W   V   S   A   I   G   S   G
                                                            ~~~~~~~~~~~~~~~~~
109   GTT CGC CAG GCT CCA GGA AAA ACT CTG GAG TGG GTC TCA GCT ATT GGT TCT GGT
                                CDR2                        ~~~~~~~~~~~~~~~~~

G   D   T   Y   Y   A   D   S   V   K   G   R   F   T   I   S   R   D
      ~~~~~~~~~~~~~~~~~
163   GGT GAT ACA TAC TAT GCA GAC TCC GTG AAG GGC CGA TTC ACC ATC TCC AGA GAC

N   A   K   N   S   L   Y   L   Q   M   N   S   L   R   A   E   D   M
217   AAT GCC AAG AAC TCC TTG TAT CTT CAA ATG AAC AGC CTG AGA GCC GAG GAC ATG

A   V   Y   Y   C   A   R   G   L   G   Y   W   N   G   Q   G   T   L   V
                                      ~~~~~~~~~~~~~~~~~~~~~~~~~~~
271   GCT GTG TAT TAC TGT GCA AGA GGA CTG GGC TAC TGG AAC GGC CAG GGA ACC CTG GTC
                                              CDR3

T   V   S   S
325   ACC GTC TCC TCA
```

Fig. 3A

Anti-PTK7 12C6 VK
V segment: A27
J segment: JK2

```
      E   I   V   L   T   Q   S   P   G   T   L   S   L   S   P   G   E   R
  1  GAA ATT GTG TTG ACG CAG TCT CCA GGC ACC CTG TCT TTG TCT CCA GGG GAA AGA
                                              ~~~~~~~~~~~~~~~~~~~~~~~~~~~~~~~
                                                          CDR1
      A   T   L   S   C   R   A   S   Q   S   V   S   S   S   Y   L   A   W
 55  GCC ACC CTC TCC TGC AGG GCC AGT CAG AGT GTT AGC AGC AGC TAC TTA GCC TGG
     ~~~~~~~~~~~~~~~~~~~~~~~~~~~~~~~~~~~~~~~~~~~~~~~~~~~~~~~~~
                                                                      CDR2
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC
                                                      ~~~~~~~~~~~~~~~~~~~~~~
     CDR2
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC
     ~~~~~~~~~
                                                                         CDR3
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG
                                                              ~~~~~~~~~~~~~~~
             CDR3
      Q   Y   G   S   S   P   M   Y   T   F   G   Q   G   T   K   L   E   I
271  CAG TAT GGT AGC TCA CCC ATG TAC ACT TTT GGC CAG GGG ACC AAG CTG GAG ATC
     ~~~~~~~~~~~~~~~~~~~~~~~~~~~~~~~~~~~

K
325  AAA
```

Fig. 3B

Anti-PTK7 12C6a VK
V segment: L15
J segment: JK2

```
      D   I   Q   M   T   Q   S   P   S   S   L   S   A   S   V   G   D   R
  1   GAC ATC CAG ATG ACC CAG TCT CCA TCC TCA CTG TCT GCA TCT GTA GGA GAC AGA

V   T   I   T   C   R   A   S   Q   G   I   S   W   L   A   W   Y
 55   GTC ACC ATC ACT TGT CGG GCG AGT CAG GGT ATT AGC AGC TGG TTA GCC TGG TAT
                              ~~~~~~~~~~~~~~~~~~~~~~~~~~~~~~~~~~~~~~~~~~~~~~~
                                          CDR1

Q   Q   K   P   E   K   A   P   K   S   L   I   Y   A   A   S   S   L
109   CAG CAG AAA CCA GAG AAA GCC CCT AAG TCC CTG ATC TAT GCT GCA TCC AGT TTG
      ~~~~~~~~~~~~~~~~~~                              ~~~~~~~~~~~~~~~~~~~~~~~
                                                              CDR2

Q   S   G   V   P   S   R   F   S   G   S   G   S   G   T   D   F   T
163   CAA AGT GGG GTC CCA TCA AGG TTC AGC GGC AGT GGA TCT GGG ACA GAT TTC ACT
      ~~~~~~                                                          
                                                                      CDR3

L   T   I   S   S   L   Q   P   E   D   F   A   T   Y   Y   C   Q   Q
217   CTC ACC ATC AGC AGC CTG CAG CCT GAA GAT TTT GCA ACT TAT TAC TGC CAA CAG
                                                              ~~~~~~~~~~~~~~~

Y   N   S   Y   P   Y   T   F   G   Q   G   T   K   L   E   I   K
271   TAT AAT AGT TAC CCG TAC ACT TTT GGC CAG GGG ACC AAG CTG GAG ATC AAA
      ~~~~~~~~~~~~~~~~~~~~~~~~~~~~
              CDR3
```

Fig. 3C

Anti-PTK7 7C8 VH
V segment:   3-33
D segment:   3-10
J segment:   JH6b

```
        Q   V   Q   L   V   E   S   G   G   G   V   V   Q   P   G   R   S   L
  1    CAG GTG CAA CTG GTG GAG TCT GGG GGA GGC GTG GTC CAG CCT GGG AGG TCC CTG
                                                               CDR1
        R   L   S   C   A   A   S   G   F   T   F   S   S   Y   G   M   H   W
  55   AGA CTC TCC TGT GCA GCG TCT GGA TTC ACC TTC AGT AGC TAT GGC ATG CAC TGG
                                                         CDR2
        V   R   Q   A   P   G   K   G   L   E   W   V   A   V   I   W   D   D
 109   GTC CGC CAG GCT CCA GGC AAG GGG CTG GAG TGG GTG GCA GTT ATA TGG GAT GAT
        G   S   N   K   Y   Y   V   D   S   V   K   G   R   F   T   I   S   R
 163   GGA AGT AAT AAA TAC TAT GTA GAC TCC GTG AAG GGC CGA TTC ACC ATC TCC AGA
        D   N   S   K   N   T   L   Y   L   Q   M   N   S   L   R   A   E   D
 217   GAC AAT TCC AAG AAC ACG CTG TAT CTG CAA ATG AAC AGC CTG AGA GCC GAG GAC
        T   A   V   Y   Y   C   A   R   D   D   Y   G   S   G   S   F   N
 271   ACG GCT GTG TAT TAC TGT GCG AGA GAT GAT TAC TAT GGT TCG GGG AGT TTT AAC
                                        CDR3
        S   Y   Y   G   T   D   V   W   G   Q   G   T   T   V   T   V   S   S
 325   TCC TAC TAC GGT ACG GAC GTC TGG GGC CAA GGG ACC ACG GTC ACC GTC TCC TCA
```

Fig. 4A

Anti-PTK7 7C8 VK
V segment: L6
J segment: JK3

```
     E   I   V   L   T   Q   S   P   A   T   L   S   L   S   P   G   E   R
 1   GAA ATT GTG TTG ACA CAG TCT CCA GCC ACC CTG TCT TTG TCT CCA GGG GAA AGA
                                         ~~~~~~~~~~~~~~~~~~~~~~~~~~~~~~~~~~
                                                   CDR1
     A   T   L   S   C   R   A   S   Q   S   V   S   I   Y   L   A   W   Y
55   GCC ACC CTC TCC TGC TGC AGG GCC AGT CAG AGT GTT AGC ATC TAC TTA GCC TGG TAC
     ~~~~~~~~~~~~~~~~~~~~~~~~~~~~~~~~~~~~~~~~~~~~~~~~~~~~~~~~~
                                                               CDR2
                                                               ~~~~~~~~~~~~
     Q   Q   K   P   G   Q   A   P   R   L   L   I   Y   D   A   S   N   R
109  CAA CAG AAA CCT GGC CAG GCT CCC AGG CTC CTC ATC TAT GAT GCA TCC AAC AGG
     ~~~~~~~~~~~~~~~~~~~~~~~~~~~~~~~~~~~~~~~~~~~~~~~~~~~~
       CDR2
     A   T   G   I   P   A   R   F   S   G   S   G   S   G   T   D   F   T
163  GCC ACT GGC ATC CCA GCC AGG TTC AGT GGC AGT GGG TCT GGG ACA GAC TTC ACT
                                                                     ~~~~~~
                                                                       CDR3
                                                                       ~~~~
     L   T   I   S   S   L   E   P   E   D   F   A   V   Y   Y   C   Q   Q
217  CTC ACC ATC AGC AGC CTA GAG CCT GAA GAT TTT GCA GTT TAT TAC TGT CAG CAG
     ~~~~~~~~~~~~~~~~~~~~~~~~~~~~~~~~~~~~~~~~~~~~~~~~~~~~~~~~~~~~~~
       CDR3
     R   S   N   W   P   P   T   F   G   P   G   T   K   V   D   I   K
271  CGT AGC AAC TGG CCT CCA ACT TTC GGC CCT GGG ACC AAA GTG GAT ATC AAA
     ~~~~~~~~~~~~~~~~~~~~~~~~~~~~~
```

Fig. 4B

Anti-PTK7 3G8 and 3G8a VH region

```
                                                                CDR1
3-30.3 germline  Q V Q L V E S G G G V V Q P G R S L R L S C A A S G F T F S S Y A M H W
3G8 VH           - - - - - - - - - - - - - - - - - - - - - - - - - - I - - - N - - - -
3G8a VH          - - - - - - - - - - - - - - - - - - - - - - - - - - I - - - N - - - -

CDR2
3-30.3 germline  V R Q A P G K G L E W V A V I S Y D G S N K Y Y A D S V K G R F T I S R
3G8 VH           - - - - - - - - - - - - - - - - - - - - N - - - - - - - - - - - - - -
3G8a VH          - - - - - - - - - - - - - - - - - - - - N - - - - - - - - - - - - - -

CDR3
3-30.3 germline  D N S K N T L Y L Q M N S L R A E D T A V Y Y C A R         D Y W G Q
JH4b germline
3G8 VH           - - - - - - - - - - - - - - - - - - - - - - - - -  E V W S I - N - -
3G8a VH          - - - - - - - - - - - - - - - - - - - - - - - - -  E V W S I - N - -

JH4b germline    G T L V T V S S             (JH4b)
3G8 VH           - - - - - - - -             (JH4b)
3G8a VH          - - - - - - - -
```

Fig. 5

Anti-PTK7 4D5 VH region

```
                                                                    CDR1
3-30.3 germline  Q V Q L V E S G G G V V Q P G R S L R L S C A A S G F T F S S Y A M H W V R
4D5 VH           - - - - - - - - - - - - - - - - - - - - - - - - - - - F - - - - - - - - -

CDR2
3-30.3 germline  Q A P G K G L E W V A V I S Y D G S N K Y Y A D S V K G R F T I S R D N S K
4D5 VH           - - - - - - - - - - - - - - - I - - - - - - - - - - - - - - - - - - - - -

CDR3
3-30.3 germline  N T L Y L Q M N S L R A E D T A V Y Y C A R                   Y F D Y W G Q G T L V T V S
JH4b germline                                                                  - - - - - - - - - - - - -
4D5 VH           - - - - - - - - - - - - - - - - - - - - -         T Y        - - - - - - - - - - - - -

JH4b germline    S    (JH4b)
4D5 VH           -
```

Fig. 6

Anti-PTK7 12C6 and 12C6a VH region

```
                                                          CDR1
DP-44 germline  E V Q L V Q S G G G L V H P G G S L R L S C A G S G F T F S S Y A M H W V R
3-7 Germline:   - E - - - - - - - - - - - Q - - - - - - - - - - - - - - - - - W - S - - -
3-23 Germline:  - - - L E - - - - - - - - Q - - - - - - - - A - - - - - - - - - - S - - - -
12C6 VH         - - - - - - - - - - - - - - - - - - - - - - A - - - - - T - T - L - Y - - -
12C6a VH        - - - - - - - - - - - - - - - - - - - - - - - - - - - - T - T - L - Y - - -

CDR2
DP-44 germline  Q A P G K G L E W V S A I G T G G G T Y Y A D S V K G R F T I S R D N A K N
3-7 Germline:   - - - - - - - - - - - A N - K Q D - S E K - V - - - - - - - - - - - - - - -
3-23 Germline:  - - - - - - - - - - - - - - S G S - S - - - - - - - - - - - - - - - - - S -
12C6 VH         - - - - - - - - - - T - - - - - S - - - - - - - - - - - - - - - - - - - - -
12C6a VH        - - - - - - - - - - T - - - - - S - - - - - - - - - - - - - - - - - - - - -

CDR3
DP-44 germline  S L Y L Q M N S L R A E D M A V Y Y C A R
3-7 Germline:   - - - - - - - - - - - - - T - - - - - - -
3-23 Germline:  - - - - - - - - - - - - - T - - - - - - K
JH4b germline                                             Y W G Q G T L V T V S S
12C6 VH         T - - - - - - - - - - - - - - - - - G L G                         (JH4b)
12C6a VH        - - - - - - - - - - - - - - - - - - G L G                         (JH4b)
```

Fig. 7

Anti-PTK7 7C8 VH region

```
                     CDR1
3-33 germline   Q V Q L V E S G G G V V Q P G R S L R L S C A A S G F T F S S Y G M H W
7C8 VH          - - - - - - - - - - - - - - - - - - - - - - - - - - - - - - - - - - -

CDR2
3-33 germline   V R Q A P G K G L E W V A V I W Y D G S N K Y Y A D S V K G R F T I S R
7C8 VH          - - - - - - - - - - - - - - - - - D - - - - - - V - - - - - - - - - -

CDR3
3-33 germline   D N S K N T L Y L Q M N S L R A E D T A V Y Y C A R
7C8 VH          - - - - - - - - - - - - - - - - - - - - - - - - - -   - D D Y Y G S G S F N JH6b germline   Y Y Y G M D V W G Q G T T V T V S S
7C8 VH          S - - T - - - - - - - - - - - - - -   (JH6b)
```

Fig. 8

Anti-PTK7 3G8 and 3G8a VK regions

```
                                                          CDR1
L15 germline   D I Q M T Q S P S S L S A S V G D R V T I T C R A S Q G I S S
3G8 VK         - - - - - - - - - - - - - - - - - - - - - - - - - - - - - -
3G8a VK        - - - - - - - - - - - - - - - - - - - - - - - - - - - - - -

CDR2
L15 germline   W L A W Y Q Q K P E K A P K S L I Y A A S S L Q S G V P S R F
3G8 VK         - - - - - - - - - - - - - - - - - - - - - - - - - - - - - -
3G8a VK        - - - - - - - - - - - - - - - - - - - - - - - - - - - - - -

CDR3
L15 germline   S G S G S G T D F T L T I S S L Q P E D F A T Y Y C Q Q Y N S
3G8 VK         - - - - - - - - - - - - - - - - - - - - - - - - - - - - - -
3G8a VK        - - - - - - - - - - - - - - - - - - - - - - - - - - - - - -

L15 germline   Y P
JK1 germline       T F G Q G T K V E I K    (JK1)
3G8 VK         - - R - - - - - - - - - -    (JK3)
3G8a VK        - - F - - - P - - D - - -
```

Fig. 9

Anti-PTK7 4D5 VK region

```
                        CDR1
A10 germline   E I V L T Q S P D F Q S V T P K E K V T I T C R A S Q S I G S
4D5 VK         - - - - - - - - - - - - - - - - - - - - - - - - - - - - - -

CDR2
A10 germline   S L H W Y Q Q K P D Q S P K L L I K Y A S Q S F S G V P S R F
4D5 VK         - - - - - - - - - - - - - - - - - - - - - - - - - - - - - -

CDR3
A10 germline   S G S G S G T D F T L T I N S L E A E D A A T Y Y C H Q S S S
4D5 VK         - - - - - - - - - - - - - - - - - - - - - - A - - - - - - - -

A10 germline   L P
JK5 germline         I T F G Q G T R L E I K   (JK5)
4D5 VK         - -   - - - - - - - - - - - -
```

Fig. 10

Anti-PTK7 12C6 VK region

```
                                                   CDR1
A27 germline     E I V L T Q S P G T L S L S P G E R A T L S C R A S Q S V S S S Y L A W
12C6 VK1         - - - - - - - - - - - - - - - - - - - - - - - - - - - - - - - - - - -

CDR2
A27 germline     Y Q Q K P G Q A P R L L I Y G A S S R A T G I P D R F S G S G S G T D F
12C6 VK1         - - - - - - - - - - - - - - - - - - - - - - - - - - - - - - - - - - -

CDR3
A27 germline     T L T I S R L E P E D F A V Y Y C Q Q Y G S S P
JK2 germline                                                     Y T F G Q G T K L E I K   (JK2)
12C6 VK1         - - - - - - - - - - - - - - - - - - - - - M - -  - - - - - - - - - - -
```

Fig. 11

Anti-PTK7 12C6a VK region

```
L15 germline   D I Q M T Q S P S S L S A S V G D R V T I T C R A S Q G I S S
12C6 VK2       - - - - - - - - - - - - - - - - - - - - - - - - - - - - - -
                                                                CDR1

L15 germline   W L A W Y Q Q K P E K A P K S L I Y A A S S L Q S G V P S R F
12C6 VK2       - - - - - - - - - - - - - - - - - - - - - - - - - - - - - -
                                              CDR2

L15 germline   S G S G S G T D F T L T I S S L Q P E D F A T Y Y C Q Q Y N S
12C6 VK2       - - - - - - - - - - - - - - - - - - - - - - - - - - - - - -
                                                                CDR3

L15 germline       Y P
12C6 VK2           - -

JK2 germline   Y T F G Q G T K L E I K    (JK2)
12C6 VK2       - - - - - - - - - - -
```

Fig. 12

Anti-PTK7 7C8 VK region

```
                                                    CDR1
L6 germline    E I V L T Q S P A T L S L S P G E R A T L S C R A S Q S V S S Y L A W Y
7C8 VK1        - - - - - - - - - - - - - - - - - - - - - - - - - - - - - I - - - - -

CDR2
L6 germline    Q Q K P G Q A P R L L I Y D A S N R A T G I P A R F S G S G S G T D F T
7C8 VK1        - - - - - - - - - - - - - - - - - - - - - - - - - - - - - - - - - - -

CDR3
L6 germline    L T I S S L E P E D F A V Y Y C Q Q R S N W P P
JK3 germline                                               P P  F T F G P G T K V D I K   (JK3)
7C8 VK1        - - - - - - - - - - - - - - - - - - - - - - -  - - - - - - - - - - - -
```

Fig. 13

ID NO:8;

SEQUENCE LISTING

<160> NUMBER OF SEQ ID NOS: 69

<210> SEQ ID NO 1
<211> LENGTH: 116
<212> TYPE: PRT
<213> ORGANISM: Homo sapiens

<400> SEQUENCE: 1

```
Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Ile Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Val Trp Ser Ile Asp Asn Trp Gly Gln Gly Thr Leu Val
            100                 105                 110

Thr Val Ser Ser
        115
```

<210> SEQ ID NO 2
<211> LENGTH: 115
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Phe His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Tyr Tyr Phe Asp Tyr Trp Gly Gln Gly Thr Leu Val Thr
            100                 105                 110

Val Ser Ser
        115

<210> SEQ ID NO 3
<211> LENGTH: 112
<212> TYPE: PRT
<213> ORGANISM: Homo sapiens

<400> SEQUENCE: 3

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Thr Tyr
            20                  25                  30

Leu Met Tyr Trp Val Arg Gln Ala Pro Gly Lys Thr Leu Glu Trp Val
        35                  40                  45

Ser Ala Ile Gly Ser Gly Gly Asp Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Leu Gly Tyr Trp Gly Gln Gly Thr Leu Val Thr Val Ser Ser
            100                 105                 110

<210> SEQ ID NO 4
<211> LENGTH: 126
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Asp Tyr Tyr Gly Ser Gly Ser Phe Asn Ser Tyr Tyr Gly
                100                 105                 110

Thr Asp Val Trp Gly Gln Gly Thr Thr Val Thr Val Ser Ser
                115                 120                 125

<210> SEQ ID NO 5
<211> LENGTH: 107
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
                100                 105

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Phe
                 85                  90                  95

Thr Phe Gly Pro Gly Thr Lys Val Asp Ile Lys
                100                 105

<210> SEQ ID NO 7
<211> LENGTH: 107
<212> TYPE: PRT
<213> ORGANISM: Homo sapiens

<400> SEQUENCE: 7
```

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
 65                  70                  75                  80

Glu Asp Ala Ala Ala Tyr Tyr Cys His Gln Ser Ser Ser Leu Pro Ile
                85                  90                  95

Thr Phe Gly Gln Gly Thr Arg Leu Glu Ile Lys
            100                 105
```

<210> SEQ ID NO 8
<211> LENGTH: 109
<212> TYPE: PRT
<213> ORGANISM: Homo sapiens

<400> SEQUENCE: 8

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Met Tyr Thr Phe Gly Gln Gly Thr Lys Leu Glu Ile Lys
            100                 105
```

<210> SEQ ID NO 9
<211> LENGTH: 107
<212> TYPE: PRT
<213> ORGANISM: Homo sapiens

<400> SEQUENCE: 9

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105
```

```
<210> SEQ ID NO 10
<211> LENGTH: 108
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
 1               5                   10                  15

Glu Arg Ala Thr Leu Ser Cys Arg Ala Ser Gln Ser Val Ser Ile Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 11
<211> LENGTH: 5
<212> TYPE: PRT
<213> ORGANISM: Homo sapiens

<400> SEQUENCE: 11

Asn Tyr Ala Met His
 1               5

<210> SEQ ID NO 12
<211> LENGTH: 5
<212> TYPE: PRT
<213> ORGANISM: Homo sapiens

<400> SEQUENCE: 12

Ser Tyr Ala Phe His
 1               5

<210> SEQ ID NO 13
<211> LENGTH: 5
<212> TYPE: PRT
<213> ORGANISM: Homo sapiens

<400> SEQUENCE: 13

Thr Tyr Leu Met Tyr
 1               5

<210> SEQ ID NO 14
<211> LENGTH: 5
<212> TYPE: PRT
<213> ORGANISM: Homo sapiens

<400> SEQUENCE: 14

Ser Tyr Gly Met His
 1               5

<210> SEQ ID NO 15
<211> LENGTH: 17
<212> TYPE: PRT
<213> ORGANISM: Homo sapiens

<400> SEQUENCE: 15
```

Val Ile Ser Tyr Asp Gly Asn Asn Lys Tyr Tyr Ala Asp Ser Val Lys
1               5                   10                  15
Gly

<210> SEQ ID NO 16
<211> LENGTH: 17
<212> TYPE: PRT
<213> ORGANISM: Homo sapiens

<400> SEQUENCE: 16

Val Ile Ser Tyr Asp Gly Ser Ile Lys Tyr Tyr Ala Asp Ser Val Lys
1               5                   10                  15
Gly

<210> SEQ ID NO 17
<211> LENGTH: 16
<212> TYPE: PRT
<213> ORGANISM: Homo sapiens

<400> SEQUENCE: 17

Ala Ile Gly Ser Gly Gly Asp Thr Tyr Tyr Ala Asp Ser Val Lys Gly
1               5                   10                  15

<210> SEQ ID NO 18
<211> LENGTH: 17
<212> TYPE: PRT
<213> ORGANISM: Homo sapiens

<400> SEQUENCE: 18

Val Ile Trp Asp Asp Gly Ser Asn Lys Tyr Tyr Val Asp Ser Val Lys
1               5                   10                  15
Gly

<210> SEQ ID NO 19
<211> LENGTH: 7
<212> TYPE: PRT
<213> ORGANISM: Homo sapiens

<400> SEQUENCE: 19

Glu Val Trp Ser Ile Asp Asn
1               5

<210> SEQ ID NO 20
<211> LENGTH: 6
<212> TYPE: PRT
<213> ORGANISM: Homo sapiens

<400> SEQUENCE: 20

Thr Tyr Tyr Phe Asp Tyr
1               5

<210> SEQ ID NO 21
<211> LENGTH: 4
<212> TYPE: PRT
<213> ORGANISM: Homo sapiens

<400> SEQUENCE: 21

Gly Leu Gly Tyr
1

<210> SEQ ID NO 22
<211> LENGTH: 17
<212> TYPE: PRT
<213> ORGANISM: Homo sapiens

<400> SEQUENCE: 22

Asp Asp Tyr Tyr Gly Ser Gly Ser Phe Asn Ser Tyr Tyr Gly Thr Asp
1               5                   10                  15
Val

<210> SEQ ID NO 23
<211> LENGTH: 11
<212> TYPE: PRT
<213> ORGANISM: Homo sapiens

<400> SEQUENCE: 23

Arg Ala Ser Gln Gly Ile Ser Ser Trp Leu Ala
1               5                   10

<210> SEQ ID NO 24
<211> LENGTH: 11
<212> TYPE: PRT
<213> ORGANISM: Homo sapiens

<400> SEQUENCE: 24

Arg Ala Ser Gln Gly Ile Ser Ser Trp Leu Ala
1               5                   10

<210> SEQ ID NO 25
<211> LENGTH: 11
<212> TYPE: PRT
<213> ORGANISM: Homo sapiens

<400> SEQUENCE: 25

Arg Ala Ser Gln Ser Ile Gly Ser Ser Leu His
1               5                   10

<210> SEQ ID NO 26
<211> LENGTH: 12
<212> TYPE: PRT
<213> ORGANISM: Homo sapiens

<400> SEQUENCE: 26

Arg Ala Ser Gln Ser Val Ser Ser Ser Tyr Leu Ala
1               5                   10

<210> SEQ ID NO 27
<211> LENGTH: 11
<212> TYPE: PRT
<213> ORGANISM: Homo sapiens

<400> SEQUENCE: 27

Arg Ala Ser Gln Gly Ile Ser Ser Trp Leu Ala
1               5                   10

<210> SEQ ID NO 28
<211> LENGTH: 11
<212> TYPE: PRT
<213> ORGANISM: Homo sapiens

<400> SEQUENCE: 28

Arg Ala Ser Gln Ser Val Ser Ile Tyr Leu Ala
1               5                   10

<210> SEQ ID NO 29
<211> LENGTH: 7
<212> TYPE: PRT
<213> ORGANISM: Homo sapiens

```
<400> SEQUENCE: 29

Ala Ala Ser Ser Leu Gln Ser
  1               5

<210> SEQ ID NO 30
<211> LENGTH: 7
<212> TYPE: PRT
<213> ORGANISM: Homo sapiens

<400> SEQUENCE: 30

Ala Ala Ser Ser Leu Gln Ser
  1               5

<210> SEQ ID NO 31
<211> LENGTH: 7
<212> TYPE: PRT
<213> ORGANISM: Homo sapiens

<400> SEQUENCE: 31

Tyr Ala Ser Gln Ser Phe Ser
  1               5

<210> SEQ ID NO 32
<211> LENGTH: 7
<212> TYPE: PRT
<213> ORGANISM: Homo sapiens

<400> SEQUENCE: 32

Gly Ala Ser Ser Arg Ala Thr
  1               5

<210> SEQ ID NO 33
<211> LENGTH: 7
<212> TYPE: PRT
<213> ORGANISM: Homo sapiens

<400> SEQUENCE: 33

Ala Ala Ser Ser Leu Gln Ser
  1               5

<210> SEQ ID NO 34
<211> LENGTH: 7
<212> TYPE: PRT
<213> ORGANISM: Homo sapiens

<400> SEQUENCE: 34

Asp Ala Ser Asn Arg Ala Thr
  1               5

<210> SEQ ID NO 35
<211> LENGTH: 9
<212> TYPE: PRT
<213> ORGANISM: Homo sapiens

<400> SEQUENCE: 35

Gln Gln Tyr Asn Ser Tyr Pro Arg Thr
  1               5

<210> SEQ ID NO 36
<211> LENGTH: 9
<212> TYPE: PRT
<213> ORGANISM: Homo sapiens

<400> SEQUENCE: 36

Gln Gln Tyr Asn Ser Tyr Pro Phe Thr
```

<210> SEQ ID NO 37
<211> LENGTH: 9
<212> TYPE: PRT
<213> ORGANISM: Homo sapiens

<400> SEQUENCE: 37

His Gln Ser Ser Ser Leu Pro Ile Thr
 1               5

<210> SEQ ID NO 38
<211> LENGTH: 10
<212> TYPE: PRT
<213> ORGANISM: Homo sapiens

<400> SEQUENCE: 38

Gln Gln Tyr Gly Ser Ser Pro Met Tyr Thr
 1               5                  10

<210> SEQ ID NO 39
<211> LENGTH: 9
<212> TYPE: PRT
<213> ORGANISM: Homo sapiens

<400> SEQUENCE: 39

Gln Gln Tyr Asn Ser Tyr Pro Tyr Thr
 1               5

<210> SEQ ID NO 40
<211> LENGTH: 10
<212> TYPE: PRT
<213> ORGANISM: Homo sapiens

<400> SEQUENCE: 40

Gln Gln Arg Ser Asn Trp Pro Pro Phe Thr
 1               5                  10

<210> SEQ ID NO 41
<211> LENGTH: 348
<212> TYPE: DNA
<213> ORGANISM: Homo sapiens
<220> FEATURE:
<221> NAME/KEY: CDS
<222> LOCATION: (1)..(348)

<400> SEQUENCE: 41 cag gtg cag ctg gtg gag tct ggg gga ggc gtg gtc cag cct ggg agg        48
Gln Val Gln Leu Val Glu Ser Gly Gly Gly Val Val Gln Pro Gly Arg
 1               5                  10                  15 tcc ctg cga ctc tcc tgt gca gcc tct gga ttc atc ttc agt aac tat        96
Ser Leu Arg Leu Ser Cys Ala Ala Ser Gly Phe Ile Phe Ser Asn Tyr
             20                  25                  30 gct atg cac tgg gtc cgc cag gct cca ggc aag ggg ctg gag tgg gtg       144
Ala Met His Trp Val Arg Gln Ala Pro Gly Lys Gly Leu Glu Trp Val
         35                  40                  45 gca gtt ata tca tat gat gga aac aat aaa tac tac gca gac tcc gtg       192
Ala Val Ile Ser Tyr Asp Gly Asn Asn Lys Tyr Tyr Ala Asp Ser Val
     50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt       288
Leu Gln Met Asn Ser Leu Arg Ala Glu Asp Thr Ala Val Tyr Tyr Cys
                 85                  90                  95

```
gcg aga gag gtc tgg agt att gac aac tgg ggc cag gga acc ctg gtc      336
Ala Arg Glu Val Trp Ser Ile Asp Asn Trp Gly Gln Gly Thr Leu Val
                100                 105                 110 acc gtc tcc tca                                                       348
Thr Val Ser Ser
        115

<210> SEQ ID NO 42
<211> LENGTH: 345
<212> TYPE: DNA
<213> ORGANISM: Homo sapiens
<220> FEATURE:
<221> NAME/KEY: CDS
<222> LOCATION: (1)..(345)

<400> SEQUENCE: 42 cag gtg cag ctg gtg gag tct ggg gga ggc gtg gtc cag cct ggg agg       48
Gln Val Gln Leu Val Glu Ser Gly Gly Gly Val Val Gln Pro Gly Arg
 1               5                  10                  15 tcc ctg aga ctc tcc tgt gca gcc tct gga ttc acc ttc agt agc tat       96
Ser Leu Arg Leu Ser Cys Ala Ala Ser Gly Phe Thr Phe Ser Ser Tyr
             20                  25                  30 gct ttc cac tgg gtc cgc cag gct cca ggc aag ggg ctg gag tgg gtg      144
Ala Phe His Trp Val Arg Gln Ala Pro Gly Lys Gly Leu Glu Trp Val
         35                  40                  45 gca gtt ata tca tat gat gga agc att aaa tac tac gca gac tcc gtg      192
Ala Val Ile Ser Tyr Asp Gly Ser Ile Lys Tyr Tyr Ala Asp Ser Val
     50                  55                  60 aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt      288
Leu Gln Met Asn Ser Leu Arg Ala Glu Asp Thr Ala Val Tyr Tyr Cys
                 85                  90                  95 gcg agg acg tac tac ttt gac tac tgg ggc cag gga acc ctg gtc acc      336
Ala Arg Thr Tyr Tyr Phe Asp Tyr Trp Gly Gln Gly Thr Leu Val Thr
            100                 105                 110 gtc tcc tca                                                           345
Val Ser Ser
    115

<210> SEQ ID NO 43
<211> LENGTH: 336
<212> TYPE: DNA
<213> ORGANISM: Homo sapiens
<220> FEATURE:
<221> NAME/KEY: CDS
<222> LOCATION: (1)..(336)

<400> SEQUENCE: 43 gag gtt cag ctg gtg cag tct ggg gga ggc ttg gta cat cct ggg ggg       48
Glu Val Gln Leu Val Gln Ser Gly Gly Gly Leu Val His Pro Gly Gly
 1               5                  10                  15 tcc ctg aga ctc tcc tgt gca ggc tct gga ttc acc ttc agt acc tat       96
Ser Leu Arg Leu Ser Cys Ala Gly Ser Gly Phe Thr Phe Ser Thr Tyr
             20                  25                  30 ctt atg tac tgg gtt cgc cag gct cca gga aaa act ctg gag tgg gtc      144
Leu Met Tyr Trp Val Arg Gln Ala Pro Gly Lys Thr Leu Glu Trp Val
         35                  40                  45 tca gct att ggt tct ggt ggt gat aca tac tat gca gac tcc gtg aag      192
Ser Ala Ile Gly Ser Gly Gly Asp Thr Tyr Tyr Ala Asp Ser Val Lys
     50                  55                  60 ggc cga ttc acc atc tcc aga gac aat gcc aag aac tcc ttg tat ctt      240
```

```
Gly Arg Phe Thr Ile Ser Arg Asp Asn Ala Lys Asn Ser Leu Tyr Leu
 65                  70                  75                  80 caa atg aac agc ctg aga gcc gag gac atg gct gtg tat tac tgt gca        288
Gln Met Asn Ser Leu Arg Ala Glu Asp Met Ala Val Tyr Tyr Cys Ala
                 85                  90                  95 aga gga ctg ggc tac tgg ggc cag gga acc ctg gtc acc gtc tcc tca        336
Arg Gly Leu Gly Tyr Trp Gly Gln Gly Thr Leu Val Thr Val Ser Ser
            100                 105                 110

<210> SEQ ID NO 44
<211> LENGTH: 378
<212> TYPE: DNA
<213> ORGANISM: Homo sapiens
<220> FEATURE:
<221> NAME/KEY: CDS
<222> LOCATION: (1)..(378)

<400> SEQUENCE: 44 cag gtg caa ctg gtg gag tct ggg gga ggc gtg gtc cag cct ggg agg         48
Gln Val Gln Leu Val Glu Ser Gly Gly Gly Val Val Gln Pro Gly Arg
  1               5                  10                  15 tcc ctg aga ctc tcc tgt gca gcg tct gga ttc acc ttc agt agc tat         96
Ser Leu Arg Leu Ser Cys Ala Ala Ser Gly Phe Thr Phe Ser Ser Tyr
             20                  25                  30 ggc atg cac tgg gtc cgc cag gct cca ggc aag ggg ctg gag tgg gtg        144
Gly Met His Trp Val Arg Gln Ala Pro Gly Lys Gly Leu Glu Trp Val
         35                  40                  45 gca gtt ata tgg gat gat gga agt aat aaa tac tat gta gac tcc gtg        192
Ala Val Ile Trp Asp Asp Gly Ser Asn Lys Tyr Tyr Val Asp Ser Val
     50                  55                  60 aag ggc cga ttc acc atc tcc aga gac aat tcc aag aac acg ctg tat        240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt        288
Leu Gln Met Asn Ser Leu Arg Ala Glu Asp Thr Ala Val Tyr Tyr Cys
                 85                  90                  95 gcg aga gat gat tac tat ggt tcg ggg agt ttt aac tcc tac tac ggt        336
Ala Arg Asp Asp Tyr Tyr Gly Ser Gly Ser Phe Asn Ser Tyr Tyr Gly
            100                 105                 110 acg gac gtc tgg ggc caa ggg acc acg gtc acc gtc tcc tca                378
Thr Asp Val Trp Gly Gln Gly Thr Thr Val Thr Val Ser Ser
        115                 120                 125

<210> SEQ ID NO 45
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 45 gac atc cag atg acc cag tct cca tcc tca ctg tct gca tct gta gga         48
Asp Ile Gln Met Thr Gln Ser Pro Ser Ser Leu Ser Ala Ser Val Gly
  1               5                  10                  15 gac aga gtc acc atc act tgt cgg gcg agt cag ggt att agc agc tgg         96
Asp Arg Val Thr Ile Thr Cys Arg Ala Ser Gln Gly Ile Ser Ser Trp
             20                  25                  30 tta gcc tgg tat cag cag aaa cca gag aaa gcc cct aag tcc ctg atc        144
Leu Ala Trp Tyr Gln Gln Lys Pro Glu Lys Ala Pro Lys Ser Leu Ile
         35                  40                  45 tat gct gca tcc agt ttg caa agt ggg gtc cca tca agg ttc agc ggc        192
Tyr Ala Ala Ser Ser Leu Gln Ser Gly Val Pro Ser Arg Phe Ser Gly
     50                  55                  60
```

```
agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gca act tat tac tgc caa cag tat aat agt tac cct cgg    288
Glu Asp Phe Ala Thr Tyr Tyr Cys Gln Gln Tyr Asn Ser Tyr Pro Arg
                 85                  90                  95 acg ttc ggc caa ggg acc aag gtg gaa atc aaa                        321
Thr Phe Gly Gln Gly Thr Lys Val Glu Ile Lys
            100                 105

<210> SEQ ID NO 46
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 46 gac atc cag atg acc cag tct cca tcc tca ctg tct gca tct gta gga     48
Asp Ile Gln Met Thr Gln Ser Pro Ser Ser Leu Ser Ala Ser Val Gly
  1               5                  10                  15 gac aga gtc acc atc act tgt cgg gcg agt cag ggt att agc agc tgg     96
Asp Arg Val Thr Ile Thr Cys Arg Ala Ser Gln Gly Ile Ser Ser Trp
                 20                  25                  30 tta gcc tgg tat cag cag aaa cca gag aaa gcc cct aag tcc ctg atc    144
Leu Ala Trp Tyr Gln Gln Lys Pro Glu Lys Ala Pro Lys Ser Leu Ile
             35                  40                  45 tat gct gca tcc agt ttg caa agt ggg gtc cca tca agg ttc agc ggc    192
Tyr Ala Ala Ser Ser Leu Gln Ser Gly Val Pro Ser Arg Phe Ser Gly
 50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gca act tat tac tgc caa cag tat aat agt tac cca ttc    288
Glu Asp Phe Ala Thr Tyr Tyr Cys Gln Gln Tyr Asn Ser Tyr Pro Phe
                 85                  90                  95 act ttc ggc cct ggg acc aaa gtg gat atc aaa                        321
Thr Phe Gly Pro Gly Thr Lys Val Asp Ile Lys
            100                 105

<210> SEQ ID NO 47
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 47 gaa att gtg ctg act cag tct cca gac ttt cag tct gtg act cca aag     48
Glu Ile Val Leu Thr Gln Ser Pro Asp Phe Gln Ser Val Thr Pro Lys
  1               5                  10                  15 gag aaa gtc acc atc acc tgc cgg gcc agt cag agc att ggt agt agc     96
Glu Lys Val Thr Ile Thr Cys Arg Ala Ser Gln Ser Ile Gly Ser Ser
                 20                  25                  30 tta cac tgg tac cag cag aaa cca gat cag tct cca aag ctc ctc atc    144
Leu His Trp Tyr Gln Gln Lys Pro Asp Gln Ser Pro Lys Leu Leu Ile
             35                  40                  45 aag tat gct tcc cag tcc ttc tca ggg gtc ccc tcg agg ttc agt ggc    192
Lys Tyr Ala Ser Gln Ser Phe Ser Gly Val Pro Ser Arg Phe Ser Gly
 50                  55                  60 agt gga tct ggg aca gat ttc acc ctc acc atc aat agc ctg gaa gct    240
Ser Gly Ser Gly Thr Asp Phe Thr Leu Thr Ile Asn Ser Leu Glu Ala
```

```
Ser Gly Ser Gly Thr Asp Phe Thr Leu Thr Ile Asn Ser Leu Glu Ala
 65                  70                  75                  80 gaa gat gct gca gcg tat tac tgt cat cag agt agt agt tta ccg atc      288
Glu Asp Ala Ala Ala Tyr Tyr Cys His Gln Ser Ser Ser Leu Pro Ile
                 85                  90                  95 acc ttc ggc caa ggg aca cga ctg gag att aaa                          321
Thr Phe Gly Gln Gly Thr Arg Leu Glu Ile Lys
            100                 105
```

<210> SEQ ID NO 48
<211> LENGTH: 327
<212> TYPE: DNA
<213> ORGANISM: Homo sapiens
<220> FEATURE:
<221> NAME/KEY: CDS
<222> LOCATION: (1)..(327)

<400> SEQUENCE: 48

```
gaa att gtg ttg acg cag tct cca ggc acc ctg tct ttg tct cca ggg       48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc       96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc ctc      144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
 50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca ccc      288
Pro Glu Asp Phe Ala Val Tyr Tyr Cys Gln Gln Tyr Gly Ser Ser Pro
                 85                  90                  95 atg tac act ttt ggc cag ggg acc aag ctg gag atc aaa                  327
Met Tyr Thr Phe Gly Gln Gly Thr Lys Leu Glu Ile Lys
            100                 105
```

<210> SEQ ID NO 49
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 49

```
gac atc cag atg acc cag tct cca tcc tca ctg tct gca tct gta gga       48
Asp Ile Gln Met Thr Gln Ser Pro Ser Ser Leu Ser Ala Ser Val Gly
 1               5                  10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
                20                  25                  30 tta gcc tgg tat cag cag aaa cca gag aaa gcc cct aag tcc ctg atc      144
Leu Ala Trp Tyr Gln Gln Lys Pro Glu Lys Ala Pro Lys Ser Leu Ile
            35                  40                  45 tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
 50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80
```

```
gaa gat ttt gca act tat tac tgc caa cag tat aat agt tac ccg tac       288
Glu Asp Phe Ala Thr Tyr Tyr Cys Gln Gln Tyr Asn Ser Tyr Pro Tyr
             85                  90                  95 act ttt ggc cag ggg acc aag ctg gag atc aaa                           321
Thr Phe Gly Gln Gly Thr Lys Leu Glu Ile Lys
            100                 105
```

<210> SEQ ID NO 50
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 50

```
gaa att gtg ttg aca cag tct cca gcc acc ctg tct ttg tct cca ggg        48
Glu Ile Val Leu Thr Gln Ser Pro Ala Thr Leu Ser Leu Ser Pro Gly
 1               5                  10                  15 gaa aga gcc acc ctc tcc tgc agg gcc agt cag agt gtt agc atc tac        96
Glu Arg Ala Thr Leu Ser Cys Arg Ala Ser Gln Ser Val Ser Ile Tyr
             20                  25                  30 tta gcc tgg tac caa cag aaa cct ggc cag gct ccc agg ctc ctc atc      144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc      192
Tyr Asp Ala Ser Asn Arg Ala Thr Gly Ile Pro Ala Arg Phe Ser Gly
     50                  55                  60 agt ggg tct ggg aca gac ttc act ctc acc atc agc agc cta gag cct      240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt agc aac tgg cct cca      288
Glu Asp Phe Ala Val Tyr Tyr Cys Gln Gln Arg Ser Asn Trp Pro Pro
             85                  90                  95 ttc act ttc ggc cct ggg acc aaa gtg gat atc aaa                      324
Phe Thr Phe Gly Pro Gly Thr Lys Val Asp Ile Lys
            100                 105
```

<210> SEQ ID NO 51
<211> LENGTH: 98
<212> TYPE: PRT
<213> ORGANISM: Homo sapiens

<400> SEQUENCE: 51

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg
```

<210> SEQ ID NO 52
<211> LENGTH: 97
<212> TYPE: PRT

-continued

<213> ORGANISM: Homo sapiens

<400> SEQUENCE: 52

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg

<210> SEQ ID NO 53
<211> LENGTH: 98
<212> TYPE: PRT
<213> ORGANISM: Homo sapiens

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 54
<211> LENGTH: 95
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 55

```
<211> LENGTH: 95
<212> TYPE: PRT
<213> ORGANISM: Homo sapiens

<400> SEQUENCE: 55

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 56
<211> LENGTH: 96
<212> TYPE: PRT
<213> ORGANISM: Homo sapiens

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 57
<211> LENGTH: 95
<212> TYPE: PRT
<213> ORGANISM: Homo sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 58
<211> LENGTH: 1070
<212> TYPE: PRT
```

<213> ORGANISM: Homo sapiens

<400> SEQUENCE: 58

```
Met Gly Ala Ala Arg Gly Ser Pro Ala Arg Pro Arg Arg Leu Pro Leu
 1               5                  10                  15

Leu Ser Val Leu Leu Leu Pro Leu Leu Gly Gly Thr Gln Thr Ala Ile
            20                  25                  30

Val Phe Ile Lys Gln Pro Ser Ser Gln Asp Ala Leu Gln Gly Arg Arg
        35                  40                  45

Ala Leu Leu Arg Cys Glu Val Glu Ala Pro Gly Pro Val His Val Tyr
    50                  55                  60

Trp Leu Leu Asp Gly Ala Pro Val Gln Asp Thr Glu Arg Arg Phe Ala
65                  70                  75                  80

Gln Gly Ser Ser Leu Ser Phe Ala Ala Val Asp Arg Leu Gln Asp Ser
                85                  90                  95

Gly Thr Phe Gln Cys Val Ala Arg Asp Asp Val Thr Gly Glu Glu Ala
            100                 105                 110

Arg Ser Ala Asn Ala Ser Phe Asn Ile Lys Trp Ile Glu Ala Gly Pro
        115                 120                 125

Val Val Leu Lys His Pro Ala Ser Glu Ala Glu Ile Gln Pro Gln Thr
    130                 135                 140

Gln Val Thr Leu Arg Cys His Ile Asp Gly His Pro Arg Pro Thr Tyr
145                 150                 155                 160

Gln Trp Phe Arg Asp Gly Thr Pro Leu Ser Asp Gly Gln Ser Asn His
                165                 170                 175

Thr Val Ser Ser Lys Glu Arg Asn Leu Thr Leu Arg Pro Ala Gly Pro
            180                 185                 190

Glu His Ser Gly Leu Tyr Ser Cys Cys Ala His Ser Ala Phe Gly Gln
        195                 200                 205

Ala Cys Ser Ser Gln Asn Phe Thr Leu Ser Ile Ala Asp Glu Ser Phe
    210                 215                 220

Ala Arg Val Val Leu Ala Pro Gln Asp Val Val Ala Arg Tyr Glu
225                 230                 235                 240

Glu Ala Met Phe His Cys Gln Phe Ser Ala Gln Pro Pro Pro Ser Leu
                245                 250                 255

Gln Trp Leu Phe Glu Asp Glu Thr Pro Ile Thr Asn Arg Ser Arg Pro
            260                 265                 270

Pro His Leu Arg Arg Ala Thr Val Phe Ala Asn Gly Ser Leu Leu Leu
        275                 280                 285

Thr Gln Val Arg Pro Arg Asn Ala Gly Ile Tyr Arg Cys Ile Gly Gln
    290                 295                 300

Gly Gln Arg Gly Pro Pro Ile Ile Leu Glu Ala Thr Leu His Leu Ala
305                 310                 315                 320

Glu Ile Glu Asp Met Pro Leu Phe Glu Pro Arg Val Phe Thr Ala Gly
                325                 330                 335

Ser Glu Glu Arg Val Thr Cys Leu Pro Pro Lys Gly Leu Pro Glu Pro
            340                 345                 350

Ser Val Trp Trp Glu His Ala Gly Val Arg Leu Pro Thr His Gly Arg
        355                 360                 365

Val Tyr Gln Lys Gly His Glu Leu Val Leu Ala Asn Ile Ala Glu Ser
    370                 375                 380

Asp Ala Gly Val Tyr Thr Cys His Ala Ala Asn Leu Ala Gly Gln Arg
385                 390                 395                 400

Arg Gln Asp Val Asn Ile Thr Val Ala Thr Val Pro Ser Trp Leu Lys
```

-continued

```
                    405                 410                 415
Lys Pro Gln Asp Ser Gln Leu Glu Glu Gly Lys Pro Gly Tyr Leu Asp
                420                 425                 430

Cys Leu Thr Gln Ala Thr Pro Lys Pro Thr Val Val Trp Tyr Arg Asn
                435                 440                 445

Gln Met Leu Ile Ser Glu Asp Ser Arg Phe Glu Val Phe Lys Asn Gly
                450                 455                 460

Thr Leu Arg Ile Asn Ser Val Glu Val Tyr Asp Gly Thr Trp Tyr Arg
465                 470                 475                 480

Cys Met Ser Ser Thr Pro Ala Gly Ser Ile Glu Ala Gln Ala Arg Val
                485                 490                 495

Gln Val Leu Glu Lys Leu Lys Phe Thr Pro Pro Gln Pro Gln Gln
                500                 505                 510

Cys Met Glu Phe Asp Lys Glu Ala Thr Val Pro Cys Ser Ala Thr Gly
                515                 520                 525

Arg Glu Lys Pro Thr Ile Lys Trp Glu Arg Ala Asp Gly Ser Ser Leu
                530                 535                 540

Pro Glu Trp Val Thr Asp Asn Ala Gly Thr Leu His Phe Ala Arg Val
545                 550                 555                 560

Thr Arg Asp Asp Ala Gly Asn Tyr Thr Cys Ile Ala Ser Asn Gly Pro
                565                 570                 575

Gln Gly Gln Ile Arg Ala His Val Gln Leu Thr Val Ala Val Phe Ile
                580                 585                 590

Thr Phe Lys Val Glu Pro Glu Arg Thr Thr Val Tyr Gln Gly His Thr
                595                 600                 605

Ala Leu Leu Gln Cys Glu Ala Gln Gly Asp Pro Lys Pro Leu Ile Gln
                610                 615                 620

Trp Lys Gly Lys Asp Arg Ile Leu Asp Pro Thr Lys Leu Gly Pro Arg
625                 630                 635                 640

Met His Ile Phe Gln Asn Gly Ser Leu Val Ile His Asp Val Ala Pro
                645                 650                 655

Glu Asp Ser Gly Arg Tyr Thr Cys Ile Ala Gly Asn Ser Cys Asn Ile
                660                 665                 670

Lys His Thr Glu Ala Pro Leu Tyr Val Val Asp Lys Pro Val Pro Glu
                675                 680                 685

Glu Ser Glu Gly Pro Gly Ser Pro Pro Pro Tyr Lys Met Ile Gln Thr
                690                 695                 700

Ile Gly Leu Ser Val Gly Ala Ala Val Ala Tyr Ile Ile Ala Val Leu
705                 710                 715                 720

Gly Leu Met Phe Tyr Cys Lys Lys Arg Cys Lys Ala Lys Arg Leu Gln
                725                 730                 735

Lys Gln Pro Glu Gly Glu Glu Pro Glu Met Glu Cys Leu Asn Gly Gly
                740                 745                 750

Pro Leu Gln Asn Gly Gln Pro Ser Ala Glu Ile Gln Glu Glu Val Ala
                755                 760                 765

Leu Thr Ser Leu Gly Ser Gly Pro Ala Ala Thr Asn Lys Arg His Ser
770                 775                 780

Thr Ser Asp Lys Met His Phe Pro Arg Ser Ser Leu Gln Pro Ile Thr
785                 790                 795                 800

Thr Leu Gly Lys Ser Glu Phe Gly Glu Val Phe Leu Ala Lys Ala Gln
                805                 810                 815

Gly Leu Glu Glu Gly Val Ala Thr Leu Val Leu Val Lys Ser Leu
                820                 825                 830
```

```
Gln Ser Lys Asp Glu Gln Gln Leu Asp Phe Arg Arg Glu Leu Glu
    835                 840                 845
Met Phe Gly Lys Leu Asn His Ala Asn Val Val Arg Leu Leu Gly Leu
850                 855                 860
Cys Arg Glu Ala Glu Pro His Tyr Met Val Leu Glu Tyr Val Asp Leu
865                 870                 875                 880
Gly Asp Leu Lys Gln Phe Leu Arg Ile Ser Lys Ser Lys Asp Glu Lys
                885                 890                 895
Leu Lys Ser Gln Pro Leu Ser Thr Lys Gln Lys Val Ala Leu Cys Thr
            900                 905                 910
Gln Val Ala Leu Gly Met Glu His Leu Ser Asn Asn Arg Phe Val His
        915                 920                 925
Lys Asp Leu Ala Ala Arg Asn Cys Leu Val Ser Ala Gln Arg Gln Val
930                 935                 940
Lys Val Ser Ala Leu Gly Leu Ser Lys Asp Val Tyr Asn Ser Glu Tyr
945                 950                 955                 960
Tyr His Phe Arg Gln Ala Trp Val Pro Leu Arg Trp Met Ser Pro Glu
                965                 970                 975
Ala Ile Leu Glu Gly Asp Phe Ser Thr Lys Ser Asp Val Trp Ala Phe
            980                 985                 990
Gly Val Leu Met Trp Glu Val Phe Thr His Gly Glu Met Pro His Gly
        995                 1000                1005
Gly Gln Ala Asp Asp Glu Val Leu Ala Asp Leu Gln Ala Gly Lys Ala
    1010                1015                1020
Arg Leu Pro Gln Pro Glu Gly Cys Pro Ser Lys Leu Tyr Arg Leu Met
1025                1030                1035                1040
Gln Arg Cys Trp Ala Leu Ser Pro Lys Asp Arg Pro Ser Phe Ser Glu
                1045                1050                1055
Ile Ala Ser Ala Leu Gly Asp Ser Thr Val Asp Ser Lys Pro
            1060                1065                1070

<210> SEQ ID NO 59
<211> LENGTH: 13
<212> TYPE: PRT
<213> ORGANISM: Homo sapiens

<400> SEQUENCE: 59

Asp Tyr Trp Gly Gln Gly Thr Leu Val Thr Val Ser Ser
1               5                   10

<210> SEQ ID NO 60
<211> LENGTH: 15
<212> TYPE: PRT
<213> ORGANISM: Homo sapiens

<400> SEQUENCE: 60

Tyr Phe Asp Tyr Trp Gly Gln Gly Thr Leu Val Thr Val Ser Ser
1               5                   10                  15

<210> SEQ ID NO 61
<211> LENGTH: 97
<212> TYPE: PRT
<213> ORGANISM: Homo sapiens

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Trp Met Ser Trp Val Arg Gln Ala Pro Gly Lys Gly Leu Glu Trp Ala
            35                  40                  45

Asn Ala Lys Gln Asp Gly Ser Glu Lys Tyr Tyr Val Asp Ser Val Lys
        50                  55                  60

Gly Arg Phe Thr Ile Ser Arg Asp Asn Ala Lys Asn Ser Leu Tyr Leu
 65                 70                  75                  80

Gln Met Asn Ser Leu Arg Ala Glu Asp Thr Ala Val Tyr Tyr Cys Ala
                85                  90                  95

Arg

<210> SEQ ID NO 62
<211> LENGTH: 97
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ser Gly Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
 65                 70                  75                  80

Gln Met Asn Ser Leu Arg Ala Glu Asp Thr Ala Val Tyr Tyr Cys Ala
                85                  90                  95

Lys

<210> SEQ ID NO 63
<211> LENGTH: 12
<212> TYPE: PRT
<213> ORGANISM: Homo sapiens

<400> SEQUENCE: 63

Tyr Trp Gly Gln Gly Thr Leu Val Thr Val Ser Ser
 1               5                  10

<210> SEQ ID NO 64
<211> LENGTH: 18
<212> TYPE: PRT
<213> ORGANISM: Homo sapiens

<400> SEQUENCE: 64

Tyr Tyr Tyr Gly Met Asp Val Trp Gly Gln Gly Thr Thr Val Thr Val
 1               5                  10                  15

Ser Ser

<210> SEQ ID NO 65
<211> LENGTH: 11
<212> TYPE: PRT
<213> ORGANISM: Homo sapiens

<400> SEQUENCE: 65

Thr Phe Gly Gln Gly Thr Lys Val Glu Ile Lys
 1               5                  10

<210> SEQ ID NO 66

```
<211> LENGTH: 12
<212> TYPE: PRT
<213> ORGANISM: Homo sapiens

<400> SEQUENCE: 66

Ile Thr Phe Gly Gln Gly Thr Arg Leu Glu Ile Lys
 1               5                  10

<210> SEQ ID NO 67
<211> LENGTH: 12
<212> TYPE: PRT
<213> ORGANISM: Homo sapiens

<400> SEQUENCE: 67

Tyr Thr Phe Gly Gln Gly Thr Lys Leu Glu Ile Lys
 1               5                  10

<210> SEQ ID NO 68
<211> LENGTH: 12
<212> TYPE: PRT
<213> ORGANISM: Homo sapiens

<400> SEQUENCE: 68

Tyr Thr Phe Gly Gln Gly Thr Lys Leu Glu Ile Lys
 1               5                  10

<210> SEQ ID NO 69
<211> LENGTH: 12
<212> TYPE: PRT
<213> ORGANISM: Homo sapiens

<400> SEQUENCE: 69

Phe Thr Phe Gly Pro Gly Thr Lys Val Asp Ile Lys
 1               5                  10
```

HUMAN MONOCLONAL ANTIBODIES TO PROTEIN TYROSINE KINASE 7 (PTK7) AND METHODS FOR USING ANTI-PTK7 ANTIBODIES

RELATED APPLICATIONS

This application claims priority to U.S. Provisional Application No. 60/748,373, filed on Dec. 8, 2005, which is incorporated herein in its entirety by this reference.

BACKGROUND OF THE INVENTION

Receptor tyrosine kinases (RTKs) are transmembrane signaling proteins that transmit biological signals from the extracellular environment to the interior of the cell. The regulation of RTK signals is important for regulation of cell growth, differentiation, axonal growth, epithelial growth, development, adhesion, migration, and apoptosis (Prenzel et al. (2001) *Endocr. Relat. Cancer* 8:11-31; Hubbard and Till (2000) *Annu. Rev. Biochem.* 69:373-98). RTKs are known to be involved in the development and progression of several forms of cancer. In most of the RTK-related cancers, there has been an amplification of the receptor protein rather than a mutation of the gene (Kobus and Fleming (2005) *Biochemistry* 44:1464-70).

Protein tyrosine kinase 7 (PTK7), a member of the receptor protein tyrosine kinase family, was first isolated from normal human melanocytes and cloned by RT-PCR (Lee et al., (1993) *Oncogene* 8:3403-10; Park et al., (1996) *J. Biochem* 119:235-9). Separately, the gene was cloned from human colon carcinoma-derived cell lines and named colon carcinoma kinase 4 (CCK4) (Mossie et al. (1995) *Oncogene* 11:2179-84). PTK7 belongs to a subset of RTKs that lack detectable catalytic tyrosine kinase activity but retain signal transduction activity and is thought to possibly function as a cell adhesion molecule.

The mRNA for PTK7 was found to be variably expressed in colon carcinoma derived cell lines but not found to be expressed in human adult colon tissues (Mossie et al., supra). PTK7 expression was also seen in some melanoma cell lines and melanoma biopsies (Easty, et al. (1997) *Int. J. Cancer* 71:1061-5). An alternative splice form was found to be expressed in hepatomas and colon cancer cells (Jung et al. (2002) *Biochim Biophys Acta* 1579:153-63). In addition, PTK7 was found to be highly overexpressed in acute myeloid leukemia samples (Muller-Tidow et al., (2004) *Clin. Cancer Res.* 10:1241-9). By immunohistochemistry, tumor specific staining of PTK7 was observed in breast, colon, lung, pancreatic, kidney and bladder cancers, as described in PCT Publication WO 04/17992.

Accordingly, agents that recognize PTK7, and methods of using such agents, are desired.

SUMMARY OF THE INVENTION

The present invention provides isolated monoclonal antibodies, in particular human monoclonal antibodies, that bind to PTK7 and that exhibit numerous desirable properties. These properties include high affinity binding to human PTK7 and binding to Wilms' tumor cells. Also provided are methods for treating a variety of PTK7 mediated diseases using the antibodies and compositions of the invention.

In one aspect, the invention pertains to an isolated monoclonal antibody, or an antigen-binding portion thereof, wherein the antibody:
  (a) specifically binds to human PTK7; and
  (b) binds to a Wilms' tumor cell line (ATCC Acc No. CRL-1441).

Preferably the antibody is a human antibody, although in alternative embodiments the antibody can be a murine antibody, a chimeric antibody or humanized antibody.

In more preferred embodiments, the antibody binds to Wilms' tumor cells with an $EC_{50}$ of 4.0 nM or less or binds to Wilms' tumor cells with an $EC_{50}$ of 3.5 nM or less.

In another embodiment, the antibody binds to a cancer cell line selected from the group consisting of A-431 (ATCC Acc No. CRL-1555), Saos-2 (ATCC Acc No. HTB-85), SKOV-3 (ATCC Acc No. HTB-77), PC3 (ATCC Acc No. CRL-1435), DMS114 (ATCC Acc No. CRL-2066), ACHN (ATCC Ace No. CRL-1611), LNCaP (ATCC Ace No. CRL-1740), DU 145 (ATCC Ace No. HTB-81), LoVo (ATCC Ace No. CCL-229) and MIA PaCa-2 (ATCC Ace No. CRL-1420) cell lines.

In another embodiment, the invention provides an isolated monoclonal antibody, or antigen binding portion thereof, wherein the antibody cross-competes for binding to PTK7 with a reference antibody, wherein the reference antibody:
  (a) specifically binds to human PTK7; and
  (b) binds to a Wilms' tumor cell line (ATCC Ace No. CRL-1441)
In various embodiments, the reference antibody comprises:
  (a) a heavy chain variable region comprising the amino acid sequence of SEQ ID NO:1; and
  (b) a light chain variable region comprising the amino acid sequence of SEQ ID NO:5;
or the reference antibody comprises:
  (a) a heavy chain variable region comprising the amino acid sequence of SEQ ID NO:1; and
  (b) a light chain variable region comprising the amino acid sequence of SEQ ID NO:6;
or the reference antibody comprises:
  (a) a heavy chain variable region comprising the amino acid sequence of SEQ ID NO:2; and
  (b) a light chain variable region comprising the amino acid sequence of SEQ ID NO:7;
or the reference antibody comprises:
  (a) a heavy chain variable region comprising the amino acid sequence of SEQ ID NO:3; and
  (b) a light chain variable region comprising the amino acid sequence of SEQ ID NO:8;
or the reference antibody comprises,
  (a) a heavy chain variable region comprising the amino acid sequence of SEQ ID NO:3; and
  (b) a light chain variable region comprising the amino acid sequence of SEQ ID NO:9;
or the reference antibody comprises:
  (a) a heavy chain variable region comprising the amino acid sequence of SEQ ID NO:4; and
  (b) a light chain variable region comprising the amino acid sequence of SEQ ID NO:10.

In one aspect, the invention pertains to an isolated monoclonal antibody, or an antigen-binding portion thereof, comprising a heavy chain variable region that is the product of or derived from a human $V_H$ 3-30.3 gene, wherein the antibody specifically binds PTK7. The invention also provides an isolated monoclonal antibody, or an antigen-binding portion thereof, comprising a heavy chain variable region that is the product of or derived from a human $V_H$ DP44 gene, wherein the antibody specifically binds PTK7. The invention also provides an isolated monoclonal antibody, or an antigen-binding portion thereof, comprising a heavy chain variable region that is the product of or derived from a human $V_H$ 3-33 gene, wherein the antibody specifically binds PTK7. The invention further provides an isolated monoclonal antibody, or an antigen-binding portion thereof, comprising a light chain variable region that is the product of or derived from a human $V_K L15$ gene, wherein the antibody specifically binds PTK7. The invention further provides an isolated monoclonal antibody, or an antigen-binding portion thereof, comprising a light chain variable region that is the product of or derived from a human $V_K A10$ gene, wherein the antibody specifically binds PTK7. The invention further provides an isolated monoclonal antibody, or an antigen-binding portion thereof, comprising a light chain variable region that is the product of or derived from a human $V_K A27$ gene, wherein the antibody specifically binds PTK7 The invention further provides an isolated monoclonal antibody, or an antigen-binding portion thereof, comprising a light chain variable region that is the product of or derived from a human $V_K L6$ gene, wherein the antibody specifically binds PTK7.

A preferred combination comprises:
 (a) a heavy chain variable region CDR1 comprising SEQ ID NO:11;
 (b) a heavy chain variable region CDR2 comprising SEQ ID NO:15;
 (c) a heavy chain variable region CDR3 comprising SEQ ID NO:19;
 (d) a light chain variable region CDR1 comprising SEQ ID NO:23;
 (e) a light chain variable region CDR2 comprising SEQ ID NO:29; and
 (f) a light chain variable region CDR3 comprising SEQ ID NO:35.

Another preferred combination comprises:
 (a) a heavy chain variable region CDR1 comprising SEQ ID NO:11;
 (b) a heavy chain variable region CDR2 comprising SEQ ID NO:15;
 (c) a heavy chain variable region CDR3 comprising SEQ ID NO:19;
 (d) a light chain variable region CDR1 comprising SEQ ID NO:24;
 (e) a light chain variable region CDR2 comprising SEQ ID NO:30; and
 (f) a light chain variable region CDR3 comprising SEQ ID NO:36.

Another preferred combination comprises:
 (a) a heavy chain variable region CDR1 comprising SEQ ID NO:12;
 (b) a heavy chain variable region CDR2 comprising SEQ ID NO:16;
 (c) a heavy chain variable region CDR3 comprising SEQ ID NO:20;
 (d) a light chain variable region CDR1 comprising SEQ ID NO:25;
 (e) a light chain variable region CDR2 comprising SEQ ID NO:31; and
 (f) a light chain variable region CDR3 comprising SEQ ID NO:37.

Another preferred combination comprises:
 (a) a heavy chain variable region CDR1 comprising SEQ ID NO:13;
 (b) a heavy chain variable region CDR2 comprising SEQ ID NO:17;
 (c) a heavy chain variable region CDR3 comprising SEQ ID NO:21;
 (d) a light chain variable region CDR1 comprising SEQ ID NO:26;
 (e) a light chain variable region CDR2 comprising SEQ ID NO:32; and
 (f) a light chain variable region CDR3 comprising SEQ ID NO:38.

Another preferred combination comprises:
 (a) a heavy chain variable region CDR1 comprising SEQ ID NO:13;
 (b) a heavy chain variable region CDR2 comprising SEQ ID NO:17;
 (c) a heavy chain variable region CDR3 comprising SEQ ID NO:21;
 (d) a light chain variable region CDR1 comprising SEQ ID NO:27;
 (e) a light chain variable region CDR2 comprising SEQ ID NO:33; and
 (f) a light chain variable region CDR3 comprising SEQ ID NO:39.

Another preferred combination comprises:
 (a) a heavy chain variable region CDR1 comprising SEQ ID NO:14;
 (b) a heavy chain variable region CDR2 comprising SEQ ID NO:18;
 (c) a heavy chain variable region CDR3 comprising SEQ ID NO:22;
 (d) a light chain variable region CDR1 comprising SEQ ID NO:28;
 (e) a light chain variable region CDR2 comprising SEQ ID NO:34; and
 (f) a light chain variable region CDR3 comprising SEQ ID NO:40.

Other preferred antibodies of the invention, or antigen binding portions thereof comprise:
 (a) a heavy chain variable region comprising the amino acid sequence of SEQ ID NO:1; and
 (b) a light chain variable region comprising the amino acid sequence of SEQ ID NO:5.

Another preferred combination comprises:
 (a) a heavy chain variable region comprising the amino acid sequence of SEQ ID NO:1; and
 (b) a light chain variable region comprising the amino acid sequence of SEQ ID NO:6.

Another preferred combination comprises:
 (a) a heavy chain variable region comprising the amino acid sequence of SEQ ID NO:2; and
 (b) a light chain variable region comprising the amino acid sequence of SEQ ID NO:7.

Another preferred combination comprises:
 (a) a heavy chain variable region comprising the amino acid sequence of SEQ ID NO:3; and
 (b) a light chain variable region comprising the amino acid sequence of SEQ ID NO:8.

Another preferred combination comprises:
 (a) a heavy chain variable region comprising the amino acid sequence of SEQ ID NO:3; and
 (b) a light chain variable region comprising the amino acid sequence of SEQ ID NO:9.

Another preferred combination comprises:
 (a) a heavy chain variable region comprising the amino acid sequence of SEQ ID NO:4; and
 (b) a light chain variable region comprising the amino acid sequence of SEQ ID NO:10.

The antibodies of the invention can be, for example, full-length antibodies, for example of an IgG1 or IgG4 isotype. Alternatively, the antibodies can be antibody fragments, such as Fab or Fab'2 fragments, or single chain antibodies.

The invention also provides an immunoconjugate comprising an antibody of the invention, or antigen-binding portion thereof, linked to a therapeutic agent, such as a cytotoxin or a radioactive isotope. The invention also provides a bispecific molecule comprising an antibody, or antigen-binding portion thereof, of the invention, linked to a second functional moiety having a different binding specificity than said antibody, or antigen binding portion thereof.

Compositions comprising an antibody, or antigen-binding portion thereof, or immunoconjugate or bispecific molecule of the invention and a pharmaceutically acceptable carrier are also provided.

Nucleic acid molecules encoding the antibodies, or antigen-binding portions thereof, of the invention are also encompassed by the invention, as well as expression vectors comprising such nucleic acids and host cells comprising such expression vectors. Moreover, the invention provides a transgenic mouse comprising human immunoglobulin heavy and light chain transgenes, wherein the mouse expresses an antibody of the invention, as well as hybridomas prepared from such a mouse, wherein the hybridoma produces the antibody of the invention.

In yet another aspect, the invention provides a method of treating or preventing a disease characterized by growth of tumor cells expressing PTK7, comprising administering to the subject the antibody, or antigen-binding portion thereof, of the invention in an amount effective to treat or prevent the disease. The disease can be, for example, cancer, e.g., colon cancer (including small intestine cancer), lung cancer, breast cancer, pancreatic cancer, melanoma (e.g., metastatic malignant melanoma), acute myeloid leukemia, kidney cancer, bladder cancer, ovarian cancer and prostate cancer.

In a preferred embodiment, the invention provides a method of treating cancer in vivo using an anti-PTK7 antibody. The anti-PTK7 antibody may be a murine, chimeric, humanized or human antibody. Examples of other cancers that may be treated using the methods of the invention include renal cancer (e.g., renal cell carcinoma), glioblastoma, brain tumors, chronic or acute leukemias including acute lymphocytic leukemia (ALL), adult T-cell leukemia (T-ALL), chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), embryonal carcinomas, undifferentiated carcinomas of the rhinopharynx (e.g., Schmincke's tumor), Castleman's disease, Kaposi's Sarcoma, multiple myeloma, Waldenstrom's macroglobulinemia and other B-cell lymphomas, nasopharangeal carcinomas, bone cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, epidermoid cancer, squamous cell cancer, environmentally induced cancers including those induced by asbestos, e.g., mesothelioma and combinations of said cancers.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO:41) and amino acid sequence (SEQ ID NO:1) of the heavy chain variable region of the 3G8 and 3G8a human monoclonal antibodies. The CDR1 (SEQ ID NO:11), CDR2 (SEQ ID NO:15) and CDR3 (SEQ ID NO:19) regions are delineated and the V, D and J germline derivations are indicated.

FIG. 1B shows the nucleotide sequence (SEQ ID NO:45) and amino acid sequence (SEQ ID NO:5) of the light chain variable region of the 3GS human monoclonal antibody. The CDR1 (SEQ ID NO:23), CDR2 (SEQ ID NO:29) and CDR3 (SEQ ID NO:35) regions are delineated and the V and J germline derivations are indicated.

FIG. 1C shows the nucleotide sequence (SEQ ID NO:46) and amino acid sequence (SEQ ID NO. 6) of the light chain variable region of the 3G8a human monoclonal antibody. The CDR1 (SEQ ID NO:24), CDR2 (SEQ ID NO:30) and CDR3 (SEQ ID NO:36) regions are delineated and the V and J germline derivations are indicated.

FIG. 2A shows the nucleotide sequence (SEQ ID NO:42) and amino acid sequence (SEQ ID NO:2) of the heavy chain variable region of the 4D5 human monoclonal antibody. The CDR1 (SEQ ID NO:12), CDR2 (SEQ ID NO:16) and CDR3 (SEQ ID NO:20) regions are delineated and the V, D and J germline derivations are indicated.

FIG. 2B shows the nucleotide sequence (SEQ ID NO:47) and amino acid sequence (SEQ ID NO:7) of the light chain variable region of the 4D5 human monoclonal antibody. The CDR1 (SEQ ID NO:25), CDR2 (SEQ ID NO:31) and CDR3 (SEQ ID NO:37) regions are delineated and the V and J germline derivations are indicated.

FIG. 3A shows the nucleotide sequence (SEQ ID NO:43) and amino acid sequence (SEQ ID NO:3) of the heavy chain variable region of the 12C6 human monoclonal antibodies. The CDR1 (SEQ ID NO:13), CDR2 (SEQ ID NO:17) and CDR3 (SEQ ID NO:21) regions are delineated and the V, D and J germline derivations are indicated.

FIG. 3B shows the nucleotide sequence (SEQ ID NO:48) and amino acid sequence (SEQ ID NO:8) of the light chain variable region of the 12C6 human monoclonal antibody. The CDR1 (SEQ ID NO:26), CDR2 (SEQ ID NO:32) and CDR3 (SEQ ID NO:38) regions are delineated and the V and J germline derivations are indicated.

FIG. 3C shows the nucleotide sequence (SEQ ID NO:49) and amino acid sequence (SEQ ID NO:9) of the light chain variable region of the 12C6a human monoclonal antibody. The CDR1 (SEQ ID NO:27), CDR2 (SEQ ID NO:33) and CDR3 (SEQ ID NO:39) regions are delineated and the V and J germline derivations are indicated.

FIG. 4A shows the nucleotide sequence (SEQ ID NO:44) and amino acid sequence (SEQ ID NO:4) of the heavy chain variable region of the 7C8 human monoclonal antibody. The CDR1 (SEQ ID NO:14), CDR2 (SEQ ID NO:18) and CDR3 (SEQ ID NO:22) regions are delineated and the V, D and J germline derivations are indicated.

FIG. 4B shows the nucleotide sequence (SEQ ID NO:50) and amino acid sequence (SEQ ID NO:10) of the light chain variable region of the 7C8 human monoclonal antibody. The CDR1 (SEQ ID NO:28), CDR2 (SEQ ID NO:34) and CDR3 (SEQ ID NO:40) regions are delineated and the V and J germline derivations are indicated.

FIG. 5 shows the alignment of the amino acid sequences of the heavy chain variable regions of 3G8 (SEQ ID NO: 1) and 3G8a (SEQ ID NO: 1) with the human germline $V_H$ 3-30.3 amino acid sequence (SEQ ID NO:51) (JH4b germline disclosed as SEQ ID NO: 59).

FIG. 6 shows the alignment of the amino acid sequence of the heavy chain variable region of 4D5 (SEQ ID NO: 2) with the human germline $V_H$ 3-30.3 amino acid sequence (SEQ ID NO:51) (JH4b germline disclosed as SEQ ID NO: 60).

FIG. 7 shows the alignment of the amino acid sequences of the heavy chain variable regions of 12C6 (SEQ ID NO: 3) and 12C6a (SEQ ID NO: 2) with the human germline $V_H$ DP44 amino acid sequence (SEQ ID NO:52) (3-7, 3-23, and JH4b germlines disclosed as SEQ ID NOS 61-63, respectively).

FIG. 8 shows the alignment of the amino acid sequence of the heavy chain variable region of 7C8 (SEQ ID NO: 4) with the human germline $V_H$ 3-33 amino acid sequence (SEQ ID NO:53) (JH6b germline disclosed as SEQ ID NO: 64).

FIG. 9 shows the alignment of the amino acid sequences of the light chain variable regions of 3G8 (SEQ ID NO: 5) and 3G8a (SEQ ID NO: 6) with the human germline $V_k$ L15 amino acid sequence (SEQ ID NO:54) (JK1 germline disclosed as SEQ ID NO: 65).

FIG. 10 shows the alignment of the amino acid sequence of the light chain variable region of 4D5 (SEQ ID NO: 7) with the human germline $V_k$ A10 amino acid sequence (SEQ ID NO:55) (JK5 germline disclosed as SEQ ID NO: 66).

FIG. 11 shows the alignment of the amino acid sequence of the light chain variable region of 12C6 (SEQ ID NO: 8) with the human germline $V_k$ A27 amino acid sequence (SEQ ID NO:56) (JK2 germline disclosed as SEQ ID NO: 67).

FIG. 12 shows the alignment of the amino acid sequence of the light chain variable region of 12C6a (SEQ ID NO: 9) with the human germline $V_k$ L15 amino acid sequence (SEQ ID NO:54) (JK2 germline disclosed as SEQ ID NO: 68).

FIG. 13 shows the alignment of the amino acid sequence of the light chain variable region of 7C8 (SEQ ID NO: 10) with the human germline $V_k$ L6 amino acid sequence (SEQ ID NO:57) (JK3 germline disclosed as SEQ ID NO: 69).

DETAILED DESCRIPTION OF THE INVENTION

Figure 14:
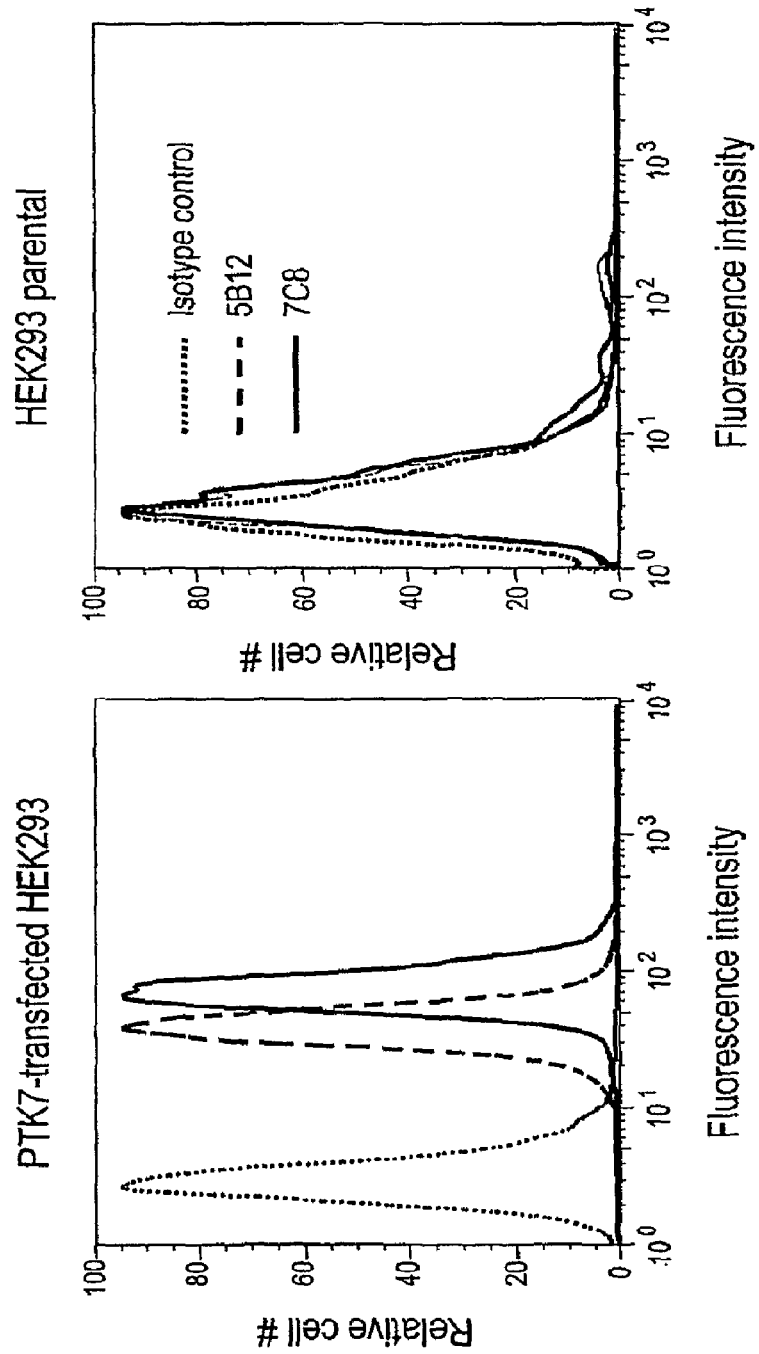
FIG. 14 shows the results of flow cytometry experiments demonstrating that the human monoclonal antibody 7C8, directed against human PTK7, binds the cell surface of HEK3 cells transfected with full-length human PTK7.

In one aspect, the present invention relates to isolated monoclonal antibodies, particularly human monoclonal antibodies, that bind specifically to PTK7. In certain embodiments, the antibodies of the invention exhibit one or more desirable functional properties, such as high affinity binding to PTK7 and/or the ability to inhibit growth of tumor cells in vitro or in vivo. In certain embodiments, the antibodies of the invention are derived from particular heavy and light chain germline sequences and/or comprise particular structural features such as CDR regions comprising particular amino acid sequences. The invention provides isolated antibodies, methods of making such antibodies, immunoconjugates and bispecific molecules comprising such antibodies and pharmaceutical compositions containing the antibodies, immunoconjugates or bispecific molecules of the invention. The invention also relates to methods of using the antibodies, such as to treat diseases such as cancer.

In order that the present invention may be more readily understood, certain terms are first defined. Additional definitions are set forth throughout the detailed description.

The terms "PTK7" and "CCK4" are used interchangeably and include variants, isoforms and species homologs of human PTK7. Accordingly, human antibodies of the invention may, in certain cases, cross-react with PTK7 from species other than human. In certain embodiments, the antibodies may be completely specific for one or more human PTK7 and may not exhibit species or other types of non-human cross-reactivity. The complete amino acid sequence of an exemplary human PTK7 has Genbank accession number NM_002821 (SEQ ID NO:58).

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the PTK7 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_h$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., PTK7). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_H$ and $C_H1$ domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g. an isolated antibody that specifically binds PTK7 is substantially free of antibodies that specifically bind antigens other than PTK7). An isolated antibody that specifically binds PTK7 may, however, have cross-reactivity to other antigens, such as PTK7 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human PTK7" is intended to refer to an antibody that binds to human PTK7 with a $K_D$ of $1 \times 10^{-7}$ M or less, more preferably $5 \times 10^{-8}$ M or less, more preferably $1 \times 10^{-8}$ M or less, more preferably $5 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Various aspects of the invention are described in further detail in the following subsections.

Anti-PTK7 Antibodies

The antibodies of the invention are characterized by particular functional features or properties of the antibodies. For example, the antibodies bind specifically to PTK7. Preferably, an antibody of the invention binds to PTK7 with high affinity, for example with a $K_D$ of $1 \times 10^{-7}$ M or less. The anti-PTK7 antibodies of the invention preferably exhibit one or more of the following characteristics:

(a) specifically binds to human PTK7; or (b) binds to a Wilms' tumor cell line (ATCC Acc No. CRL-1441).

Preferably, the antibody binds to human PTK7 with a $K_D$ of $5 \times 10^{-8}$ M or less, binds to human PTK7 with a $K_D$ of $1 \times 10^{-8}$ M or less, binds to human PTK7 with a $K_D$ of $5 \times 10^{-9}$ M or less, or binds to human PTK7 with a $K_D$ of between $1 \times 10^{-8}$ M and $1 \times 10^{-10}$ M or less. Preferably, the antibody binds to Wilms' tumor cells with an $EC_{50}$ of 4.0 nM or less, or binds to Wilms' tumor cells with an $EC_{50}$ of 3.5 nM or less. Standard assays to evaluate the binding ability of the antibodies toward PTK7 are known in the art, including for example, ELISAs, Western blots and RIAs. The binding kinetics (e.g., binding affinity) of the antibodies also can be assessed by standard assays known in the art, such as by ELISA, Scatchard and Biacore analysis. As another example, the antibodies of the present invention may bind to a kidney carcinoma tumor cell line, for example, the Wilms' tumor cell line. Suitable assays for evaluating any of the above-described characteristics are described in detail in the Examples.

Monoclonal Antibodies 3G8, 3G8a, 4D5, 12C6, 12C6a and 7C8

Preferred antibodies of the invention are the human monoclonal antibodies 3G8, 3G8a, 4D5, 12C6, 12C6a and 7C8, isolated and structurally characterized as described in Examples 1 and 2. Those having ordinary skill in the art shall appreciate that the antibodies 3G8 and 3G8a, as well as the antibodies 12C6 and 12C6a have the same heavy chain sequence, while differing in their light chain sequences. The $V_H$ amino acid sequences of 3G8, 3G8a, 4D5, 12C6, 12C6a and 7C8 are shown in SEQ ID NOs: 1 (3G8 and 3G8a), 2 (4D5), 3 (12C6 and 12C6a) and 4 (7C8). The $V_L$ amino acid sequences of 3G8, 3G8a, 4D5, 12C6, 12C6a, and 7C8 are shown in SEQ ID NOs: 5, 6, 7, 8, 9 and 10, respectively.

Given that each of these antibodies can bind to PTK7, the $V_H$ and $V_L$ sequences can be "mixed and matched" to create other anti-PTK7 binding molecules of the invention. PTK7 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, the invention provides an isolated monoclonal antibody, or antigen binding portion thereof comprising:

(a) a heavy chain variable region comprising an amino acid sequence selected from the group consisting of SEQ ID NOs: 1, 2, 3 and 4; and (b) a light chain variable region comprising an amino acid sequence selected from the group consisting of SEQ ID NOs: 5, 6, 7, 8, 9 and 10;

wherein the antibody specifically binds PTK7, preferably human PTK7. Preferred heavy and light chain combinations include:

(a) a heavy chain variable region comprising the amino acid sequence of SEQ ID NO:1; and (b) a light chain variable region comprising the amino acid sequence of SEQ ID NO:5; or (a) a heavy chain variable region comprising the amino acid sequence of SEQ ID NO:1; and (b) a light chain variable region comprising the amino acid sequence of SEQ ID NO:6; or (a) a heavy chain variable region comprising the amino acid sequence of SEQ ID NO:2; and (b) a light chain variable region comprising the amino acid sequence of SEQ ID NO:7; or (a) a heavy chain variable region comprising the amino acid sequence of SEQ ID NO:3; and (b) a light chain variable region comprising the amino acid sequence of SEQ ID NO:8; or (a) a heavy chain variable region comprising the amino acid sequence of SEQ ID NO:3; and (b) a light chain variable region comprising the amino acid sequence of SEQ ID NO:9; or (a) a heavy chain variable region comprising the amino acid sequence of SEQ ID NO:4; and (b) a light chain variable region comprising the amino acid sequence of SEQ ID NO:10.

In another aspect, the invention provides antibodies that comprise the heavy chain and light chain CDR1s, CDR2s and CDR3s of 3G8, 3G8a, 4D5, 12C6, 12C6a and 7C8, or combinations thereof. The amino acid sequences of the $V_H$ CDR1 s of 3G8, 3G8a, 4D5, 12C6, 12C6a and 7C8 are shown in SEQ ID NOs: 11 (3G8 and 3G8a), 12 (4D5), 13 (12C6 and 12C6a) and 14 (7C8). The amino acid sequences of the $V_H$ CDR2s of 3G8, 3G8a, 4D5, 12C6, 12C6a and 7C8 are shown in SEQ ID NOs: (3G8 and 3G8a), 16 (4D5), 17 (12C6 and 12C6a) and 18 (7C8). The amino acid sequences of the $V_H$ CDR3s of 3G8, 3G8a, 4D5, 12C6, 12C6a and 7C8 are shown in SEQ ID NOs: 19 (3G8 and 3G8a), 20 (4D5), 21 (12C6 and 12C6a) and 22 (7C8). The amino acid sequences of the $V_k$ CDR1 s of 3G8, 3G8a, 4D5, 12C6, 12C6a and 7C8 are shown in SEQ ID NOs: 23, 24, 25, 26, 27 and 28, respectively. The amino acid sequences of the $V_k$ CDR2s of 3G8, 3G8a, 4D5, 12C6, 12C6a and 7C8 are shown in SEQ ID NOs: 29, 30, 31, 32, 33 and 34, respectively. The amino acid sequences of the $V_k$ CDR3s of 3G8, 3G8a, 4D5, 12C6, 12C6a and 7C8 are shown in SEQ ID NOs: 35, 36, 37, 38, 39 and 40, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to PTK7 and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-PTK7 binding molecules of the invention. PTK7 binding of such "mixed and matched" antibodies can be tested using the binding assays described above and in the Examples (e.g., ELISAs, Biacore analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 3G8, 3G8a, 4D5, 12C6, 12C6a and 7C8.

Accordingly, in another aspect, the invention provides an isolated monoclonal antibody, or antigen binding portion thereof comprising:

(a) a heavy chain variable region CDR1 comprising an amino acid sequence selected from the group consisting of SEQ ID NOs: 11, 12, 13 and 14;

(b) a heavy chain variable region CDR2 comprising an amino acid sequence selected from the group consisting of SEQ ID NOs: 15, 16, 17 and 18;

(c) a heavy chain variable region CDR3 comprising an amino acid sequence selected from the group consisting of SEQ ID NOs: 19, 20, 21 and 22;

(d) a light chain variable region CDR1 comprising an amino acid sequence selected from the group consisting of SEQ ID NOs: 23, 24, 25, 26, 27 and 28;

(e) a light chain variable region CDR2 comprising an amino acid sequence selected from the group consisting of SEQ ID NOs: 29, 30, 31, 32, 33 and 34; and (f) a light chain variable region CDR3 comprising an amino acid sequence selected from the group consisting of SEQ ID NOs: 35, 36, 37, 38, 39 and 40;

wherein the antibody specifically binds PTK7, preferably human PTK7.

In a preferred embodiment, the antibody comprises:
(a) a heavy chain variable region CDR1 comprising SEQ ID NO:11;
(b) a heavy chain variable region CDR2 comprising SEQ ID NO:15;
(c) a heavy chain variable region CDR3 comprising SEQ ID NO:19;
(d) a light chain variable region CDR1 comprising SEQ ID NO:23;
(e) a light chain variable region CDR2 comprising SEQ ID NO:29; and
(f) a light chain variable region CDR3 comprising SEQ ID NO:35.

In another preferred embodiment, the antibody comprises:
(a) a heavy chain variable region CDR1 comprising SEQ ID NO:11;
(b) a heavy chain variable region CDR2 comprising SEQ ID NO:15;
(c) a heavy chain variable region CDR3 comprising SEQ ID NO:19;
(d) a light chain variable region CDR1 comprising SEQ ID NO:24;
(e) a light chain variable region CDR2 comprising SEQ ID NO:30; and
(f) a light chain variable region CDR3 comprising SEQ ID NO:36.

In another preferred embodiment, the antibody comprises:
(a) a heavy chain variable region CDR1 comprising SEQ ID NO:12;
(b) a heavy chain variable region CDR2 comprising SEQ ID NO:16;
(c) a heavy chain variable region CDR3 comprising SEQ ID NO:20;
(d) a light chain variable region CDR1 comprising SEQ ID NO:25;
(e) a light chain variable region CDR2 comprising SEQ ID NO:31; and
(f) a light chain variable region CDR3 comprising SEQ ID NO:37.

In another preferred embodiment, the antibody comprises:
(a) a heavy chain variable region CDR1 comprising SEQ ID NO:13;
(b) a heavy chain variable region CDR2 comprising SEQ ID NO:17;
(c) a heavy chain variable region CDR3 comprising SEQ ID NO:21;

(d) a light chain variable region CDR1 comprising SEQ ID NO:26;

(e) a light chain variable region CDR2 comprising SEQ ID NO:32; and (f) a light chain variable region CDR3 comprising SEQ ID NO:38.

In another preferred embodiment, the antibody comprises:

(a) a heavy chain variable region CDR1 comprising SEQ ID NO:13;

(b) a heavy chain variable region CDR2 comprising SEQ ID NO:17;

(c) a heavy chain variable region CDR3 comprising SEQ ID NO:21;

(d) a light chain variable region CDR1 comprising SEQ ID NO:27;

(e) a light chain variable region CDR2 comprising SEQ ID NO:33; and (f) a light chain variable region CDR3 comprising SEQ ID NO:39.

In another preferred embodiment, the antibody comprises:

(a) a heavy chain variable region CDR1 comprising SEQ ID NO:14;

(b) a heavy chain variable region CDR2 comprising SEQ ID NO:18;

(c) a heavy chain variable region CDR3 comprising SEQ ID NO:22;

(d) a light chain variable region CDR1 comprising SEQ ID NO:28;

(e) a light chain variable region CDR2 comprising SEQ ID NO:34; and (f) a light chain variable region CDR3 comprising SEQ ID NO:40.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et. al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, the present invention provides monoclonal antibodies comprising one or more heavy and/or light chain CDR3 domains from an antibody derived from a human or non-human animal, wherein the monoclonal antibody is capable of specifically binding to PTK7. Within certain aspects, the present invention provides monoclonal antibodies comprising one or more heavy and/or light chain CDR3 domain from a non-human antibody, such as a mouse or rat antibody, wherein the monoclonal antibody is capable of specifically binding to PTK7. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present invention provides monoclonal antibodies comprising one or more heavy and/or light chain CDR3 domain from a human antibody, such as, for example, a human antibody obtained from a non-human animal, wherein the human antibody is capable of specifically binding to PTK7. Within other aspects, the present invention provides monoclonal antibodies comprising one or more heavy and/or light chain CDR3 domain from a first human antibody, such as, for example, a human antibody obtained from a non-human animal, wherein the first human antibody is capable of specifically binding to PTK7 and wherein the CDR3 domain from the first human antibody replaces a CDR3 domain in a human antibody that is lacking binding specificity for PTK7 to generate a second human antibody that is capable of specifically binding to PTK7. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody. In preferred embodiments, the first human antibody is 3G8, #g8a, 4D5, 12C6, 12C6a or 7C8.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a human $V_H$ 3-30.3 gene, wherein the antibody specifically binds PTK7, preferably human PTK7. In another preferred embodiment, the invention provides an isolated monoclonal antibody, or an antigen-binding portion thereof, comprising a heavy chain variable region that is the product of or derived from a human $V_H$ DP44 gene, wherein the antibody specifically binds PTK7, preferably human PTK7. In another preferred embodiment, the invention provides an isolated monoclonal antibody, or an antigen-binding portion thereof, comprising a heavy chain variable region that is the product of or derived from a human $V_H$ 3-33 gene, wherein the antibody specifically binds PTK7, preferably human PTK7. In yet another preferred embodiment, the invention provides an isolated monoclonal antibody, or an antigen-binding portion thereof, comprising a light chain variable region that is the product of or derived from a human $V_K$ L15 gene, wherein the antibody specifically binds PTK7, preferably human PTK7. In yet another preferred embodiment, the invention provides an isolated monoclonal antibody, or an antigen-binding portion thereof, comprising a light chain variable region that is the product of or derived from a human $V_K$A10 gene, wherein the antibody specifically binds PTK7, preferably human PTK7. In yet another preferred embodiment, the invention provides an isolated monoclonal antibody, or an antigen-binding portion thereof, comprising a light chain variable region that is the product of or derived from a human $V_K$A27 gene, wherein the antibody specifically binds PTK7, preferably human PTK7. In yet another preferred embodiment, the invention provides an isolated monoclonal antibody, or an antigen-binding portion thereof, comprising a light chain variable region that is the product of or derived from a human $V_K$L6 gene, wherein the antibody specifically binds PTK7, preferably human PTK7. In yet another preferred embodiment, the invention provides an isolated monoclonal antibody, or antigen-binding portion thereof, wherein the antibody:

(a) comprises a heavy chain variable region that is the product of or derived from a human $V_H$3-30.3, DP44 or 3-33 gene (which gene encodes the amino acid sequence set forth in SEQ ID NOs: 51, 52 or 53, respectively);

(b) comprises a light chain variable region that is the product of or derived from a human $V_K$L15, A10, A27 or L6 gene (which gene encodes the amino acid sequence set forth in SEQ ID NO:54, 55, 56 or 57, respectively); and (c) specifically binds to PTK7.

Examples of antibodies having $V_H$ and $V_K$ of $V_H$3-30.3 and $V_K$L15, respectively, are 3G8 and 3G8a. An example of an antibody having $V_H$ and $V_K$ of $V_H$3-30.3 and $V_K$A10, respectively is 4D5. An example of an antibody having $V_H$ and $V_K$ of $V_H$DP44 and $V_K$A27, respectively is 12C6. An example of an antibody having $V_H$ and $V_K$ of $V_H$DP44 and $V_K$L15, respectively is 12C6a. An example of an antibody having $V_H$ and $V_K$ of $V_H$3-33 and $V_K$L6, respectively is 7C8.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-PTK7 antibodies of the invention.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 1, 2, 3 and 4;

(b) the light chain variable region comprises an amino acid sequence that is at least 80% homologous to an amino acid sequence selected from the group consisting of SEQ ID NOs: 5, 6, 7, 8, 9 and 10; and the antibody exhibits one or more of the following properties:

(c) the antibody binds to human PTK7 with a $K_D$ of 1×1-7 M or less;

(d) the antibody binds to the Wilms' tumor cell line.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 41, 42, 43, 44, 45, 46, 47, 48, 49 and 50, followed by testing of the encoded altered antibody for retained function (i.e., the functions set forth in (c) and (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. (See www.ncbi.nlm.nih.gov).

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 3G8, 3G8a, 4D5, 12C6, 12C6a or 7C8), or conservative modifications thereof, and wherein the antibodies retain the desired functional properties of the anti-PTK7 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 19, 20, 21 and 22, and conservative modifications thereof;

(b) the light chain variable region CDR3 sequence comprises an amino acid sequence selected from the group consisting of amino acid sequence of SEQ ID NOs: 35, 36, 37, 38, 39 and 40, and conservative modifications thereof; and the antibody exhibits one or more of the following properties:

(c) specifically binds to human PTK7; and (d) binds to a Wilms' tumor cell line (ATCC Acc No. CRL-1441).

In a preferred embodiment, the heavy chain variable region CDR2 sequence comprises an amino acid sequence selected from the group consisting of amino acid sequences of SEQ ID NOs: 15, 16, 17 and 18, and conservative modifications thereof; and the light chain variable region CDR2 sequence comprises an amino acid sequence selected from the group consisting of amino acid sequences of SEQ ID NOs: 29, 30, 31, 32, 33 and 34, and conservative modifications thereof. In another preferred embodiment, the heavy chain variable region CDR1 sequence comprises an amino acid sequence selected from the group consisting of amino acid sequences of SEQ ID NOs: 11, 12, 13 and 14, and conservative modifications thereof; and the light chain variable region CDR1 sequence comprises an amino acid sequence selected from the group consisting of amino acid sequences of SEQ ID NOs: 23, 24, 25, 26, 27 and 28, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, praline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) and (d) above) using the functional assays described herein.

Antibodies that Bind to the Same Epitope as Anti-PTK7 Antibodies of the Invention In another embodiment, the invention provides antibodies that bind to the same epitope on human PTK7 as any of the PTK7 monoclonal antibodies of the invention (i.e., antibodies that have the ability to cross-compete for binding to PTK7 with any of the monoclonal antibodies of the invention). In preferred embodiments, the reference antibody for cross-competition studies can be the monoclonal antibody 3G8 (having $V_H$ and $V_L$ sequences as shown in SEQ ID NOs: 1 and 5, respectively), or the monoclonal antibody 3G8a (having $V_H$ and $V_L$ sequences as shown in SEQ ID NOs: 1 and 6, respectively), or the monoclonal antibody 4D5 (having $V_H$ and $V_L$ sequences as shown in SEQ ID NOs: 2 and 7, respectively), or the monoclonal antibody 12C6 (having $V_H$ and $V_L$ sequences as shown in SEQ ID NOs: 3 and 8, respectively), or the monoclonal antibody 12C6a (having $V_H$ and $V_L$ sequences as shown in SEQ ID NOs: 3 and 9, respectively), or the monoclonal antibody 7C8 (having $V_H$ and $V_L$ sequences as shown in SEQ ID NOs: 4 and 10, respectively). Such cross-competing antibodies can be identified based on their ability to cross-compete with 3G8, 3G8a, 4D5, 12C6, 12C6a or 7C8 in standard PTK7 binding assays. For example, BIAcore analysis, ELISA assays or flow cytometry may be used to demonstrate cross-competition with the antibodies of the current invention. The ability of a test antibody to inhibit the binding of, for example, 3G8, 3G8a, 4D5, 12C6, 12C6a or 7C8, to human PTK7 demonstrates that the test antibody can compete with 3G8, 3G8a, 4D5, 12C6, 12C6a or 7C8 for binding to human PTK7 and thus binds to the same epitope on human PTK7 as 3G8, 3G8a, 4D5, 12C6, 12C6a or 7C8. In a preferred embodiment, the antibody that binds to the same epitope on human PTK7 as 3G8, 3G8a, 4D5, 12C6, 12C6a or 7C8 is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CD2, and CDR3 sequences comprising an amino acid sequence selected from the group consisting of SEQ ID NOs: 11, 12, 13 and 14, SEQ ID NOs: 15, 16, 17 and 18 and SEQ ID NOs: 19, 20, 21 and 22, respectively, and a light chain variable region comprising CDR1, CDR2, and CDR3 sequences comprising an amino acid sequence selected from the group consisting of SEQ ID NOs: 23, 24, 25, 26, 27 and 28, SEQ ID NOs: 29, 30, 31, 32, 33 and 34 and SEQ ID NOs: 35, 36, 37, 38, 39 and 40, respectively. Thus, such antibodies contain the $V_H$ and $V_L$ CDR sequences of monoclonal antibodies 3G8, 3G8a, 4D5, 12C6, 12C6a or 7C8 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase, as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (?) and 3-23 (AJ406678).

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (http://vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the invention are those that are structurally similar to the framework sequences used by selected antibodies of the invention, e.g., similar to the $V_H$ 3-30.3 framework sequences (SEQ ID NO:51) and/or the $V_H$ DP44 framework sequences (SEQ ID NO:52) and/or the $V_H$ 3-33 framework sequences (SEQ ID NO:53) and/or the $V_K$ L15 framework sequences (SEQ ID NO:54) and/or the $V_K$ A10 framework sequences (SEQ ID NO:55) and/or the $V_K$ L15 framework sequences (SEQ ID NO:54) and/or the $V_K$ A27 framework sequences (SEQ ID NO:56) and/or the $V_K$ L15 framework sequences (SEQ ID NO:54) and/or the $V_K$ L6 framework sequences (SEQ ID NO:57) used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-PTK7 monoclonal antibodies, or antigen binding portions thereof, comprising a heavy chain variable region comprising: (a) a $V_H$ CDR1 region comprising an amino acid sequence selected from the group consisting of SEQ ID NOs: 11, 12, 13 and 14, or an amino acid sequence having one, two, three, four or five amino acid substitutions, deletions or additions as compared to SEQ ID NOs: 11, 12, 13 and 14; (b) a $V_H$ CDR2 region comprising an amino acid sequence selected from the group consisting of SEQ ID NOs: 15, 16, 17 and 18, or an amino acid sequence having one, two, three, four or five amino acid substitutions, deletions or additions as compared to SEQ ID NOs: 15, 16, 17 and 18; (c) a $V_H$ CDR3 region comprising an amino acid sequence selected from the group consisting of SEQ ID NOs: 19, 20, 21 and 22, or an amino acid sequence having one, two, three, four or five amino acid substitutions, deletions or additions as compared to SEQ ID NOs: 19, 20, 21 and 22; (d) a $V_K$ CDR1 region comprising an amino acid sequence selected from the group consisting of SEQ ID NOs: 23, 24, 25, 26, 27 and 28, or an amino acid sequence having one, two, three, four or five amino acid substitutions, deletions or additions as compared to SEQ ID NOs: 23, 24, 25, 26, 27 and 28; (e) a $V_K$ CDR2 region comprising an amino acid sequence selected from the group consisting of SEQ ID NOs: 29, 30, 31, 32, 33 and 34, or an amino acid sequence having one, two, three, four or five amino acid substitutions, deletions or additions as compared to SEQ ID NOs: 29, 30, 31, 32, 33 and 34; and (f) a $V_K$ CDR3 region comprising an amino acid sequence selected from the group consisting of SEQ ID NOs: 35, 36, 37, 38, 39 and 40, or an amino acid sequence having one, two, three, four or five amino acid substitutions, deletions or additions as compared to SEQ ID NOs: 35, 36, 37, 38, 39 and 40.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, for 3G8 (and 3G8a), amino acid residue #28 (within FR1) of $V_H$ is an isoleucine whereas this residue in the corresponding $V_H$ 3-30.3 germline sequence is a threonine. To return the framework region sequences to their germline configuration, the somatic mutations can be "backmutated" to the germline sequence by, for example, site-directed mutagenesis or PCR-mediated mutagenesis (e.g., residue #28 of FR1 of the $V_H$ of 3G8 (and 3G8a) can be "backmutated" from isoleucine to threonine).

As another example, for 12C6 (and 12C6a), amino acid residue #44 (within FR2) of $V_H$ is a threonine whereas this residue in the corresponding $V_H$ DP44 germline sequence is a glycine. To return the framework region sequences to their germline configuration, for example, residue #44 (residue #9 of FR2) of the $V_H$ of 12C6 (and 12C6a) can be "backmutated" from threonine to glycine. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fe region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) $J. Biol. Chem.$ 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8v-cell lines were created by the targeted disruption of the FUT8 gene in CHO/DG44 cells using two replacement vectors (see U.S. Patent Publication No. 20040110704 by Yamane et al. and Yamane-Ohnuki et al. (2004) $Biotechnol Bioeng$ 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) $J. Biol. Chem.$ 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) $Nat. Biotech.$ 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) $Biochem.$ 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Antibody Physical Properties

The antibodies of the present invention may be further characterized by the various physical properties of the anti-PTK7 antibodies. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) $Annu Rev Biochem$ 41:673-702; Gala F A and Morrison S L (2004) $J Immunol$ 172:5489-94; Wallick et at (1988) $J Exp Med$ 168:1099-109; Spiro R G (2002) $Glycobiology$ 12:43R-56R; Parekh et al (1985) $Nature$ 316:452-7; Mimura et al. (2000) $Mol Immunol$ 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-PTK7 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-PTK7 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning M C (2002) *Curr Pharm Biotechnol* 3:361-71). A higher thermal stability indicates greater overall antibody stability in vivo. The melting point of an antibody may be measure using techniques such as differential scanning calorimetry (Chen et at (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-PTK7 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-PTK7 antibodies having $V_H$ and $V_K$ sequences disclosed herein can be used to create new anti-PTK7 antibodies by modifying the VH and/or $V_K$ sequences, or the constant region(s) attached thereto. Thus, in another aspect of the invention, the structural features of an anti-PTK7 antibody of the invention, e.g. 3G8, 3G8a, 4D5, 12C6, 12C6a or 7C8, are used to create structurally related anti-PTK7 antibodies that retain at least one functional property of the antibodies of the invention, such as binding to human PTK7. For example, one or more CDR regions of 3G8, 3G8a, 4D5, 12C6, 12C6a or 7C8, or mutations thereof, can be combined recombinantly with known framework regions and/or other CDRs to create additional, recombinantly-engineered, anti-PTK7 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequencers) derived from the original sequencers) and then the "second generation" sequence(s) is prepared and expressed as a protein.

Accordingly, in another embodiment, the invention provides a method for preparing an anti-PTK7 antibody comprising:

(a) providing: (i) a heavy chain variable region antibody sequence comprising a CDR1 sequence selected from the group consisting of SEQ ID NOs: 11, 12, 13 and 14, a CDR2 sequence selected from the group consisting of SEQ ID NOs: 15, 16, 17 and 18, and/or a CDR3 sequence selected from the group consisting of SEQ ID NOs: 19, 20, 21 and 22; and/or (ii) a light chain variable region antibody sequence comprising a CDR1 sequence selected from the group consisting of SEQ ID NOs: 23, 24, 25, 26, 27 and 28, a CDR2 sequence selected from the group consisting of SEQ ID NOs: 29, 30, 31, 32, 33 and 34, and/or a CDR3 sequence selected from the group consisting of SEQ ID NOs: 35, 36, 37, 38, 39 and 40;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-PTK7 antibodies described herein, which functional properties include, but are not limited to:

(a) the antibody binds to human PTK7 with a $K_D$ of $1 \times 10^{-7}$ M or less;

(b) the antibody binds the Wilms' tumor cell line.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-PTK7 antibody coding sequence and the resulting modified anti-PTK7 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 3G8, 3G8a, 4D5, 12C6, 12C6a or 7C8 monoclonal antibodies. DNA sequences encoding the VH sequences of 3G8, 3G8a, 4D5, 12C6, 12C6a and 7C8 are shown in SEQ ID NOs: 41 (3G8 and 3G8a), 42 (4D5), 43 (12C6 and 12C6a) and 44 (7C8). DNA sequences encoding the VL sequences of 3G8, 3G8a, 4D5, 12C6, 12C6a and 7C8 are shown in SEQ ID NOs: 45, 46, 47, 48, 49 and 50, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g. human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against PTK7 can be generated using transgenic or transchromosomic mice carrying parts of the human immune system rather than the mouse system. These transgenic and transchromosomic mice include mice referred to herein as HuMAb mice and KM Mice™, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368 (6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchromosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-PTK7 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-PTK7 antibodies of the invention. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-PTK7 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of PTK7 antigen and/or recombinant PTK7, or a PTK7 fusion protein, as described by Lonberg, N. et al. (1994) Nature 368 (6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 μg) of PTK7 antigen can be used to immunize the human Ig mice intraperitoneally.

Detailed procedures to generate fully human monoclonal antibodies to PTK7 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-PTK7 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse™ strain can be used, as described in Example 1.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to PTK7 by, for example, standard ELISA. Briefly, microtiter plates are coated with purified PTK7 at 0.25 µg/ml in PBS, and then blocked with 5% bovine serum albumin in PBS. Dilutions of antibody (e.g., dilutions of plasma from PTK7-immunized mice) are added to each well and incubated for 1-2 hours at 37° C. The plates are washed with PBS/Tween and then incubated with secondary reagent (e.g. for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with PTK7 immunogen. Hybridomas that bind with high avidity to PTK7 are subcloned and further characterized. One clone from each hybridoma, which retains the reactivity of the parent cells (by ELISA), can be chosen for making a 5-10 vial cell bank stored at −140° C., and for antibody purification.

To purify anti-PTK7 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-PTK7 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using PTK7 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4D C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-PTK7 human IgGs can be further tested for reactivity with PTK7 antigen by Western blotting. Briefly, PTK7 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present invention features an anti-PTK7 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e-g, dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst). Examples of therapeutic cytotoxins may be found, for example, in U.S. Pat. Nos. 6,548,530 and 6,281,354 and US Patent application Nos: US 2003/0064984, US 2003/0073852 and US 2003/0050331.

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunoconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Delkker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-PTK7 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for PTK7 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR or FcαR expressing effector cells (e.g., monocytes, macrophages or polymorphonuclear cells (PMNs)), and to target cells expressing PTK7. These bispecific molecules target PTK7 expressing cells to effector cell and trigger Fc receptor-mediated effector cell activities, such as phagocytosis of an PTK7 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-PTK7 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_c$ receptor or target cell antigen. The "anti-enhancement factor portion" can bind an $F_c$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRIII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mnAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. Fcα RI (CD89) is constitutively expressed on monocytes/macrophages, eosinophilic and neutrophilic granulocytes, but not on non-effector cell populations. FcαRI has medium affinity ($\approx 5 \times 10^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-PTK7 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-PTK7 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PTK7 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-PTK7 antibody of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

The antibodies, antibody compositions and methods of the present invention have numerous in vitro and in vivo diagnostic and therapeutic utilities involving the diagnosis and treatment of PTK7 mediated disorders. In a preferred embodiment, the antibodies of the present invention are human antibodies. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles. Preferred subjects include human patients having disorders mediated by PTK7 activity. The methods are particularly suitable for treating human patients having a disorder associated with aberrant PTK7 expression. When antibodies to PTK7 are administered together with another agent, the two can be administered in either order or simultaneously.

Given the specific binding of the antibodies of the invention for PTK7, the antibodies of the invention can be used to specifically detect PTK7 expression on the surface of cells and, moreover, can be used to purify PTK7 via immunoaffinity purification.

The invention further provides methods for detecting the presence of human PTK7 antigen in a sample, or measuring the amount of human PTK7 antigen, comprising contacting the sample, and a control sample, with a human monoclonal antibody, or an antigen binding portion thereof, which specifically binds to human PTK7, under conditions that allow for formation of a complex between the antibody or portion thereof and human PTK7. The formation of a complex is then detected, wherein a difference complex formation between the sample compared to the control sample is indicative the presence of human PTK7 antigen in the sample.

PTK7 is expressed in colon carcinoma derived cell lines but not found to be expressed in human adult colon tissues Mossie et al. (1995) *Oncogene* 11:2179-84). PTK7 expression was also seen in some melanoma cell lines and melanoma biopsies Hasty, et al. (1997) *Int. J. Cancer* 71:1061-5). In addition, PTK7 was found to be highly overexpressed in acute myeloid leukemia samples (Muller-Tidow et al., (2004) *Clin. Cancer Res.* 10:1241-9). An anti-PTK7 antibody may be used alone to inhibit the growth of cancerous tumors. Alternatively, an anti-PTK7 antibody may be used in conjunction with other immunogenic agents, standard cancer treatments or other antibodies, as described below.

Preferred cancers whose growth may be inhibited using the antibodies of the invention include cancers typically responsive to immunotherapy. Non-limiting examples of preferred cancers for treatment include colon cancer (including small intestine cancer), lung cancer, breast cancer, pancreatic cancer, melanoma (e.g., metastatic malignant melanoma), acute myeloid leukemia, kidney cancer, bladder cancer, ovarian cancer and prostate cancer. Examples of other cancers that may be treated using the methods of the invention include renal cancer (e.g., renal cell carcinoma), glioblastoma, brain tumors, chronic or acute leukemias including acute lymphocytic leukemia (ALL), adult T-cell leukemia (T-ALL), chronic myeloid leukemia, acute lymphoblastic leukemia, chronic lymphocytic leukemia, lymphomas (e.g., Hodglin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas, nasopharangeal carcinomas, bone cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, epidermoid cancer, squamous cell cancer, environmentally induced cancers including those induced by asbestos, e.g., mesothelioma and combinations of said cancers.

Furthermore, given the expression of PTK7 on various tumor cells, the human antibodies, antibody compositions and methods of the present invention can be used to treat a subject with a tumorigenic disorder, e.g., a disorder characterized by the presence of tumor cells expressing PTK7 including, for example, colon cancer (including small intestine cancer), melanoma (e.g., metastatic malignant melanoma), acute myeloid leukemia, lung cancer, breast cancer, bladder cancer, pancreatic cancer, ovarian cancer and prostate cancer. Examples of other subjects with a tumorigenic disorder include subjects having renal cancer (e.g., renal cell carcinoma), glioblastoma, brain tumors, chronic or acute leukemias including acute lymphocytic leukemia (ALL), adult T-cell leukemia (T-ALL), chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas, nasopharangeal carcinomas, bone cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, epidermoid cancer, squamous cell cancer, environmentally induced cancers including those induced by asbestos, e.g., mesothelioma and combinations of said cancers.

Accordingly, in one embodiment, the invention provides a method of inhibiting growth of tumor cells in a subject, comprising administering to the subject a therapeutically effective amount of an anti-PTK7 antibody or antigen-binding portion thereof. Preferably, the antibody is a human anti-PTK7 antibody (such as any of the human anti-human PTK7 antibodies described herein). Additionally or alternatively, the antibody may be a chimeric or humanized anti-PTK7 antibody.

In one embodiment, the antibodies (e.g., human monoclonal antibodies, multispecific and bispecific molecules and compositions) of the invention can be used to detect levels of PTK7 or levels of cells which contain PTK7 on their membrane surface, which levels can then be linked to certain disease symptoms. Alternatively, the antibodies can be used to inhibit or block PTK7 function which, in turn, can be linked to the prevention or amelioration of certain disease symptoms, thereby implicating PTK7 as a mediator of the disease. This can be achieved by contacting an experimental sample and a control sample with the anti-PTK7 antibody under conditions that allow for the formation of a complex between the antibody and PTK7. Any complexes formed between the antibody and PTK7 are detected and compared in the experimental sample and the control.

In another embodiment, the antibodies (e.g., human antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g., human antibodies, multispecific and bispecific molecules, immunoconjugates and compositions) of the invention have additional utility in therapy and diagnosis of PTK7-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing PTK7; to mediate phagocytosis or ADCC of a cell expressing PTK7 in the presence of human effector cells; or to block PTK7 ligand binding to PTK7.

In a particular embodiment, the antibodies (e.g., human antibodies, multispecific and bispecific molecules and compositions) are used in vivo to treat, prevent or diagnose a variety of PTK7-related diseases. Examples of PTK7-related diseases include, among others, colon cancer (including small intestine cancer), melanoma (e.g., metastatic malignant melanoma), acute myeloid leukemia, lung cancer, breast cancer, bladder cancer, pancreatic cancer, ovarian cancer and prostate cancer.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-PTK7 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-PTK7 antibodies or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

In one embodiment, immunoconjugates of the invention can be used to target compounds (e.g., therapeutic agents, labels, cytotoxins, radiotoxins immunosuppressants, etc.) to cells which have PTK7 cell surface receptors by linking such compounds to the antibody. For example, an anti-PTK7 antibody can be conjugated to any of the toxin compounds described in U.S. Pat. Nos. 6,281,354 and 6,548,530, US patent publication Nos. 20030050331, 20030064984, 20030073852 and 20040087497 or published in WO 03/022806, which are hereby incorporated by reference in their entireties. Thus, the invention also provides methods for localizing ex vivo or in vivo cells expressing PTK7 (e.g., with a detectable label, such as a radioisotope, a fluorescent compound, an enzyme or an enzyme co-factor). Alternatively, the immunoconjugates can be used to kill cells which have PTK7 cell surface receptors by targeting cytotoxins or radiotoxins to PTK7.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing PTK7 and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-PTK7 antibodies linked to anti-Fc-gamma RI or anti-CD3 may be used in conjunction with IgG- or IgA-receptor specific binding agents.

Bispecific and multi specific molecules of the invention can also be used to modulate FcγR or FcγR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of the invention which have complement binding sites, such as portions from IgG1, -2 or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules and immunoconjugates) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Accordingly, patients treated with antibody compositions of the invention can be additionally administered (prior to, simultaneously with or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ) and tumor necrosis factor (TNF).

The compositions (e.g., human antibodies, multispecific and bispecific molecules) of the invention can also be used to target cells expressing FcγR or PTK7, for example for labeling such cells. For such use, the binding agent can be linked to a molecule that can be detected. Thus, the invention provides methods for localizing ex vivo or in vitro cells expressing Fc receptors, such as FcγR or PTK7. The detectable label can be, e.g., a radioisotope, a fluorescent compound, an enzyme or an enzyme co-factor.

Also within the scope of the present invention are kits comprising the antibody compositions of the invention (e.g., human antibodies, bispecific or multispecific molecules, or immunoconjugates) and instructions for use. The kit can further contain one more additional reagents, such as an immunosuppressive reagent, a cytotoxic agent or a radiotoxic agent or one or more additional human antibodies of the invention (e.g., a human antibody having a complementary activity which binds to an epitope in the PTK7 antigen distinct from the first human antibody). Kits typically include a label indicating the intended use of the contents of the kit. The term label includes any writing, or recorded material supplied on or with the kit, or which otherwise accompanies the kit.

The present invention is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against PTK7

Antigen

Immunization protocols utilized as antigen both (i) a recombinant fusion protein comprising the extracellular portion of PTK7 with both a myc and his tag and (ii) membrane bound full-length PTK7. Both antigens were generated by recombinant transfection methods in a CHO cell line.

Transgenic HuMab and KM Mice™

Fully human monoclonal antibodies to PTK7 were prepared using the HCo7 and HCo12 strains of HuMab transgenic mice and the KM strain of transgenic transchromosomic mice, each of which express human antibody genes. In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,770,429; 5,545,806; 5,625,825; and 5,545,807. The HCo12 strain carries the HCo12 human heavy chain transgene as described in Example 2 of WO 01/09187 or example 2 WO 01/14424. The KM strain contains the SC20 transchromosome as described in PCT Publication WO 02/43478.

HuMab and KM Immunizations:

To generate fully human monoclonal antibodies to PTK7, HuMab mice and KM Mice™ were immunized with purified recombinant PTK7 fusion protein and PTK7-transfected CHO cells as antigen. General immunization schemes for HuMab mice are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen. A purified recombinant preparation (5-50 μg) of PTK7 fusion protein antigen and 5–10×10$^6$ cells were used to immunize the HuMab mice and KM Mice™ intraperitonealy, subcutaneously (Sc) or via footpad injection.

Transgenic mice were immunized twice with antigen in complete Freund's adjuvant or Ribi adjuvant IP, followed by 3-21 days IP (up to a total of 11 immunizations) with the antigen in incomplete Freund's or Ribi adjuvant. The immune response was monitored by retroorbital bleeds. The plasma was screened by ELISA (as described below), and mice with sufficient titers of anti-PTK7 human immunoglobulin were used for fusions. Mice were boosted intravenously with antigen 3 days before sacrifice and removal of the spleen. Typically, 10-35 fusions for each antigen were performed. Several dozen mice were immunized for each antigen.

Selection of HuMab or KM Mice™ Producing Anti-PTK7 Antibodies:

To select HuMab or KM Mice™ producing antibodies that bound PTK7, sera from immunized mice were tested by ELISA as described by Fishwild, D. et al. (1996). Briefly, microtiter plates were coated with purified recombinant PTK7 fusion protein from transfected CHO cells at 1-2 µg/ml in PBS, 100 µl/wells incubated 4° C. overnight then blocked with 200 µl/well of 5% fetal bovine serum in PBS/Tween (0.05%). Dilutions of sera from PTK7-immunized mice were added to each well and incubated for 1-2 hours at ambient temperature. The plates were washed with PBS/Tween and then incubated with a goat-anti-human IgG polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-PTK7 antibodies were used for fusions. Fusions were performed as described below and hybridoma supernatants were tested for anti-PTK7 activity by ELISA.

Generation of Hybridomas Producing Human Monoclonal Antibodies to PTK7:

The mouse splenocytes, isolated from the HuMab mice, were fused with PEG to a mouse myeloma cell line based upon standard protocols. The resulting hybridomas were then screened for the production of antigen-specific antibodies. Single cell suspensions of splenocytes from immunized mice were fused to one-fourth the number of SP2/0 nonsecreting mouse myeloma cells (ATCC, CRL 1581) with 50% PEG (Sigma). Cells were plated at approximately $1 \times 10^5$/well in flat bottom microtiter plate, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by ELISA (described above) for human anti-PTK7 monoclonal IgG antibodies. Once extensive hybridoma growth occurred, medium was monitored usually after 10-14 days. The antibody-secreting hybridomas were replated, screened again and, if still positive for human IgG, anti-PTK7 monoclonal antibodies were subcloned at least twice by limiting dilution. The stable subclones were then cultured in vitro to generate small amounts of antibody in tissue culture medium for further characterization.

Hybridoma clones 3G8, 3G8a, 4D5, 12C6, 12C6a and 7C8 were selected for further analysis.

Example 2

Structural Characterization of Human Monoclonal Antibodies 3G8, 3G8a, 4D5, 12C6, 12C6a and 7C8

The cDNA sequences encoding the heavy and light chain variable regions of the 3G8, 3G8a, 4D5, 12C6, 12C6a and 7C8 monoclonal antibodies were obtained from the 3G8, 3G8a, 4D5, 12C6, 12C6a and 7C8 hybridomas, respectively, using standard PCR techniques and were sequenced using standard DNA sequencing techniques.

The nucleotide and amino acid sequences of the heavy chain variable region of 3G8 are shown in FIG. 1A and in SEQ ID NO:41 and 1, respectively.

The nucleotide and amino acid sequences of the light chain variable region of 3G8 are shown in FIG. 1B and in SEQ ID NO:45 and 5, respectively.

Comparison of the 3G8 heavy chain immunoglobulin sequence to the known human germline immunoglobulin heavy chain sequences demonstrated that the 3G8 heavy chain utilizes a VH segment from human germline VH 3-30.3, an undetermined D segment, and a JH segment from human germline JH 4b. The alignment of the 3G8 VH sequence to the germline VH 3-30.3 sequence is shown in FIG. 5. Further analysis of the 3G8 VH sequence using the Kabat system of CDR region determination led to the delineation of the heavy chain CDR1, CDR2 and CD3 regions as shown in FIGS. 1A and 5, and in SEQ ID NOs: 11, 15 and 19, respectively.

Comparison of the 3G8 light chain immunoglobulin sequence to the known human germline immunoglobulin light chain sequences demonstrated that the 3G8 light chain utilizes a VL segment from human germline VK L15 and a JK segment from human germline JK 1. The alignment of the 3G8 VL sequence to the germline VK L15 sequence is shown in FIG. 9. Further analysis of the 3G8 VL sequence using the Kabat system of CDR region determination led to the delineation of the light chain CDR1, CDR2 and CD3 regions as shown in FIGS. 1B and 9, and in SEQ ID NOs: 23, 29 and 35, respectively.

The nucleotide and amino acid sequences of the heavy chain variable region of 3G8a are shown in FIG. 1A and in SEQ ID NO:41 and 1, respectively.

The nucleotide and amino acid sequences of the light chain variable region of 3G8a are shown in FIG. 1C and in SEQ ID NO:46 and 6, respectively.

Comparison of the 3G8a heavy chain immunoglobulin sequence to the known human germline immunoglobulin heavy chain sequences demonstrated that the 3G8a heavy chain utilizes a VH segment from human germline VH 3-30.3, an undetermined D segment, and a JH segment from human germline JH 4b. The alignment of the 3G8a VH sequence to the germline VH 3-30.3 sequence is shown in FIG. 5. Further analysis of the 3G8a VH sequence using the Kabat system of CDR region determination led to the delineation of the heavy chain CDR1, CDR2 and CD3 regions as shown in FIGS. 1A and 5, and in SEQ ID NOs: 11, 15 and 19, respectively.

Comparison of the 3G8a light chain immunoglobulin sequence to the known human germline immunoglobulin light chain sequences demonstrated that the 3G8a light chain utilizes a VL segment from human germline VK L15 and a JK segment from human germline JK 3. The alignment of the 3G8a VL sequence to the germline VK L15 sequence is shown in FIG. 9. Further analysis of the 3G8a VL sequence using the Kabat system of CDR region determination led to the delineation of the light chain CDR1, CDR2 and CD3 regions as shown in FIGS. 1C and 9, and in SEQ ID NOs: 24, 30 and 36, respectively.

The nucleotide and amino acid sequences of the heavy chain variable region of 4D5 are shown in FIG. 2A and in SEQ ID NO:42 and 2, respectively.

The nucleotide and amino acid sequences of the light chain variable region of 4D5 are shown in FIG. 2B and in SEQ ID NO:47 and 7, respectively.

Comparison of the 4D5 heavy chain immunoglobulin sequence to the known human germline immunoglobulin heavy chain sequences demonstrated that the 4D5 heavy chain utilizes a VH segment from human germline VH 3-30.3, an undetermined D segment, and a JH segment from human germline JH 4b. The alignment of the 4D5 VH sequence to the germline VH 3-30.3 sequence is shown in FIG. 6. Further analysis of the 4D5 VH sequence using the Kabat system of CDR region determination led to the delineation of the heavy chain CDR1, CDR2 and CD3 regions as shown in FIGS. 2A and 6, and in SEQ ID NOs: 12, 16 and 20, respectively.

Comparison of the 4D5 light chain immunoglobulin sequence to the known human germline immunoglobulin light chain sequences demonstrated that the 4D5 light chain utilizes a VL segment from human germline VK A10 and a JK segment from human germline 3K 5. The alignment of the 4D5 VL sequence to the germline VK A10 sequence is shown in FIG. 10. Further analysis of the 4D5 VL sequence using the Kabat system of CDR region determination led to the delineation of the light chain CDR1, CDR2 and CD3 regions as shown in FIGS. 2B and 10, and in SEQ ID NOs: 25, 31 and 37, respectively.

The nucleotide and amino acid sequences of the heavy chain variable region of 12C6 are shown in FIG. 3A and in SEQ ID NO:43 and 3, respectively.

The nucleotide and amino acid sequences of the light chain variable region of 12C6 are shown in FIG. 3B and in SEQ ID NO:48 and 8, respectively.

Comparison of the 12C6 heavy chain immunoglobulin sequence to the known human germline immunoglobulin heavy chain sequences demonstrated that the 12C6 heavy chain utilizes a VH segment from human germline VH DP44, an undetermined D segment, and a JH segment from human germline JH 4b. The alignment of the 12C6 $V_H$ sequence to the germline VH DP44 sequence is shown in FIG. 7. Further analysis of the 12C6 $V_H$ sequence using the Kabat system of CDR region determination led to the delineation of the heavy chain CDR1, CDR2 and CD3 regions as shown in FIGS. 3A and 7, and in SEQ ID NOs: 13, 17 and 21, respectively.

Comparison of the 12C6 light chain immunoglobulin sequence to the known human germline immunoglobulin light chain sequences demonstrated that the 12C6 light chain utilizes a VL segment from human germline VK A27 and a JK segment from human germline JK 2. The alignment of the 12C6 VL sequence to the germline VK A27 sequence is shown in FIG. 11. Further analysis of the 12C6 VL sequence using the Kabat system of CDR region determination led to the delineation of the light chain CDR1, CDR2 and CD3 regions as shown in FIGS. 3B and 11, and in SEQ ID NOs: 26, 32 and 38, respectively.

The nucleotide and amino acid sequences of the heavy chain variable region of 12C6a are shown in FIG. 3A and in SEQ ID NO:43 and 3, respectively.

The nucleotide and amino acid sequences of the light chain variable region of 12C6a are shown in FIG. 3C and in SEQ ID NO:49 and 9, respectively.

Comparison of the 12C6a heavy chain immunoglobulin sequence to the known human germline immunoglobulin heavy chain sequences demonstrated that the 12C6a heavy chain utilizes a VH segment from human germline VH DP44, an undetermined D segment, and a JH segment from human germline JH 4b. The alignment of the 12C6a $V_H$ sequence to the germline VH DP44 sequence is shown in FIG. 7. Further analysis of the 12C6a VH sequence using the Kabat system of CDR region determination led to the delineation of the heavy chain CDR1, CDR2 and CD3 regions as shown in FIGS. 3A and 7, and in SEQ ID NOs: 13, 17 and 21, respectively.

Comparison of the 12C6a light chain immunoglobulin sequence to the known human germline immunoglobulin light chain sequences demonstrated that the 12C6a light chain utilizes a VL segment from human germline VK L15 and a JK segment from human germline JK 2. The alignment of the 12C6a $V_L$ sequence to the germline VK L15 sequence is shown in FIG. 12. Further analysis of the 12C6a VL sequence using the Kabat system of CDR region determination led to the delineation of the light chain CDR1, CDR2 and CD3 regions as shown in FIGS. 3C and 12, and in SEQ ID NOs: 27, 33 and 39, respectively.

The nucleotide and amino acid sequences of the heavy chain variable region of 7C8 are shown in FIG. 4A and in SEQ U) NO:44 and 4, respectively.

The nucleotide and amino acid sequences of the light chain variable region of 7C8 are shown in FIG. 4B and in SEQ ID NO:50 and 10, respectively.

Comparison of the 7C8 heavy chain immunoglobulin sequence to the known human germline immunoglobulin heavy chain sequences demonstrated that the 7C8 heavy chain utilizes a VH segment from human germline VH 3-33, a D segment from human germline 3-10, and a JH segment from human germline JH 6b. The alignment of the 7C8 VH sequence to the germline VH 3-33 sequence is shown in FIG. 8. Further analysis of the 7C8 VH sequence using the Kabat system of CDR region determination led to the delineation of the heavy chain CDR1, CDR2 and CD3 regions as shown in FIGS. 4A and 8, and in SEQ ID NOs: 14, 18 and 22, respectively.

Comparison of the 7C8 light chain immunoglobulin sequence to the known human germline immunoglobulin light chain sequences demonstrated that the 7C8 light chain utilizes a VL segment from human germline VK L6 and a JK segment from human germline JK 3. The alignment of the 7C8 VL sequence to the germline VK L6 sequence is shown in FIG. 13. Further analysis of the 7C8 VL sequence using the Kabat system of CDR region determination led to the delineation of the light chain CDR1, CDR2 and CD3 regions as shown in FIGS. 4B and 13, and in SEQ ID NOs: 28, 34 and 40, respectively.

Example 3

Mutation of mAb 12C6 and Alternative Germline Usage

As discussed in Example 2 above, monoclonal antibodies 12C6 and 12C6a utilize a heavy chain variable region derived from a human DP-44 germline sequence present in the HCo7 transgene of the HuMab Mouse® strain. Since DP-44 is not a germline sequence that is utilized in the native human immunoglobulin repertoire, it may be advantageous to mutate the VH sequence of 12C6 and 12C6a to reduce potential immunogenicity. Preferably, one or more framework residues of the 12C6 or 12C6a VH sequence is mutated to a residue(s) present in the framework of a structurally related VH germline sequence that is utilized in the native human immunoglobulin repertoire For example, FIG. 7 shows the alignment of the 12C6 and 12C6a VH sequence with the DP44 germline sequence and also to two structurally related human germline sequences, VH 3-23 and VH 3-7. Given the relatedness of these sequences, one can predict that one can select a human antibody that specifically binds to human PTK7 and that utilizes a VH region derived from a VH 3-23 or VH 3-7 germline sequence. Moreover, one can mutate one or more residues within the 12C6 or 12C6a VH sequence that differ from the residue(s) at the comparable position in the VH 3-23 or VH 3-7 sequence to the residue(s) that is present in VH 3-23 or VH 3-7, or to a conservative amino acid substitution thereof.

Example 4

Characterization of Binding Specificity and Binding Kinetics of Anti-PTK7 Human Monoclonal Antibodies In this example, binding affinity and binding kinetics of anti-PTK7 antibodies were examined by Biacore analysis. Binding specificity, and cross-competition were examined by flow cytometry.

Binding Specificity by Flow Cytometry

HEK3 cell lines that express recombinant human PTK7 at the cell surface were developed and used to determine the specificity of PTK7 human monoclonal antibodies by flow cytometry. HEK3 cells were transfected with expression plasmids containing full length cDNA encoding transmembrane forms of PTK7. Binding of the 7C8 anti-PTK7 human monoclonal antibody was assessed by incubating the transfected cells with the anti-PTK7 human monoclonal antibody at a concentration of 10 µg/ml. The cells were washed and binding was detected with a FITC-labeled anti-human IgG Ab. Flow cytometric analyses were performed using a FACScan flow cytometry (Becton Dickinson, San Jose, Calif.). The results are depicted in FIG. 14. The anti-PTK7 human monoclonal antibody 7C8 bound to the HEK3 cells transfected with PTK7 but not to HEK3 cells that were not transfected with human PTK7. This data demonstrates the specificity of anti-PTK7 human monoclonal antibodies for PTK7.

Binding Specificity by ELISA

The binding of anti-PTK7 antibodies was also assessed by standard ELISA to examine the specificity of binding for PTK7.

Figure 15:
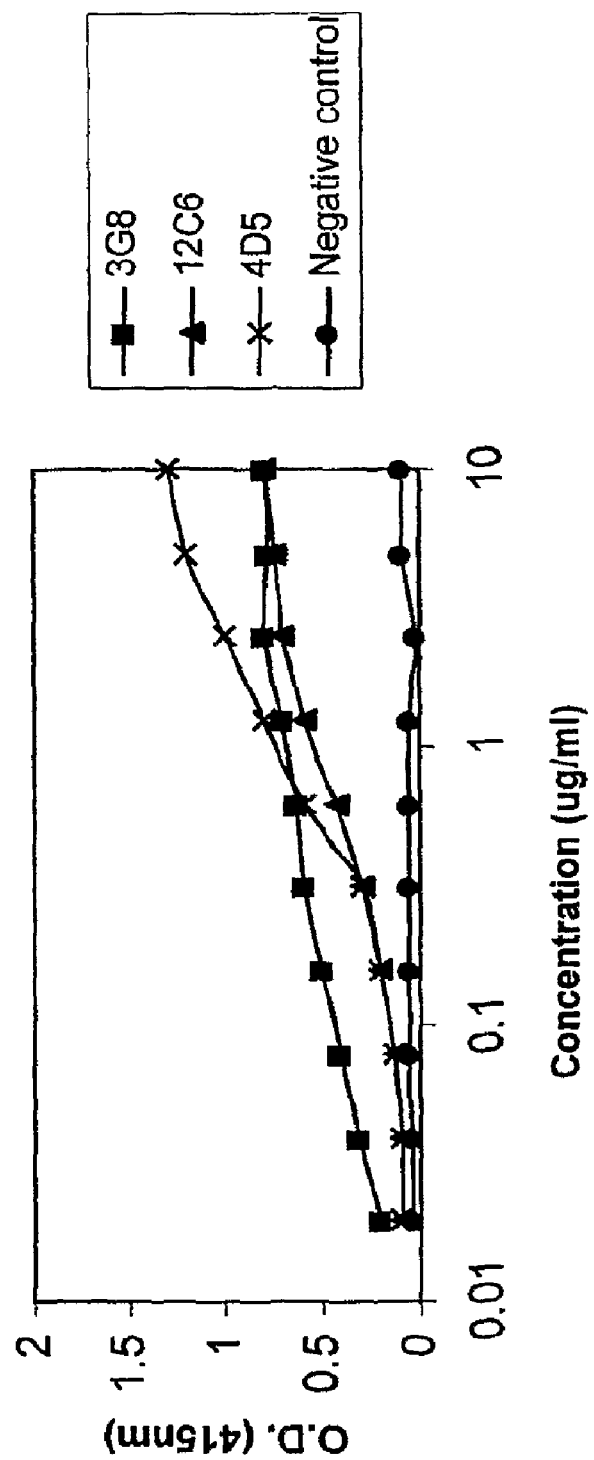
FIG. 15 shows the results of ELISA experiments demonstrating that human monoclonal antibodies against human PTK7 specifically bind to PTK7.

Recombinant extracellular domain of PTK7 was tested for binding against the anti-PTK7 human monoclonal antibodies 3G8, 4D5, 12C6 and 12C6a at different concentrations. Standard ELISA procedures were performed. The anti-PTK7 human monoclonal antibodies were added at a starting concentration of 10 µg/ml and serially diluted at a 1:2 dilution. Goat-anti-human IgG (kappa chain-specific) polyclonal antibody conjugated with horseradish peroxidase (HRP) was used as secondary antibody. The results are shown in FIG. 15. Each of the anti-PTK7 human monoclonal antibodies 3G8, 4D5, 12C6 and 12C6a bound to PTK7. This data demonstrates the specificity of anti-PTK7 human monoclonal antibodies for PTK7.

Epitope Mapping of Anti-PTK7 Antibodies

Flow cytometry was used to determine epitope grouping of anti-PTK7 HuMAbs. Wilms' tumor cells G-401 (ATCC Acc No. CRL-1441) were transfected with expression plasmids containing full length cDNA encoding transmembrane forms of PTK7. Epitope binding of each anti-PTK7 human monoclonal antibody was assessed by incubating $1 \times 10^5$ transfected cells with 10 µg/ml of cold anti-PTK7 human monoclonal antibody, washed, and followed by the addition of 10 µg/ml of a fluorescence-conjugated anti-PTK7 human monoclonal antibody. Binding was detected with a FITC-labeled anti-human IgG Ab. Flow cytometric analyses were performed using a FACScan flow cytometry (Becton Dickinson, San Jose, Calif.). Upon analysis of the data, the anti-PTK7 antibodies have been categorized into 3 epitope groups—group A, which includes 7D11, group B, which includes 3G8 and 3G8a and group C, which includes 7C8, 12C6 and 12C6a.

Example 5

Figure 16:
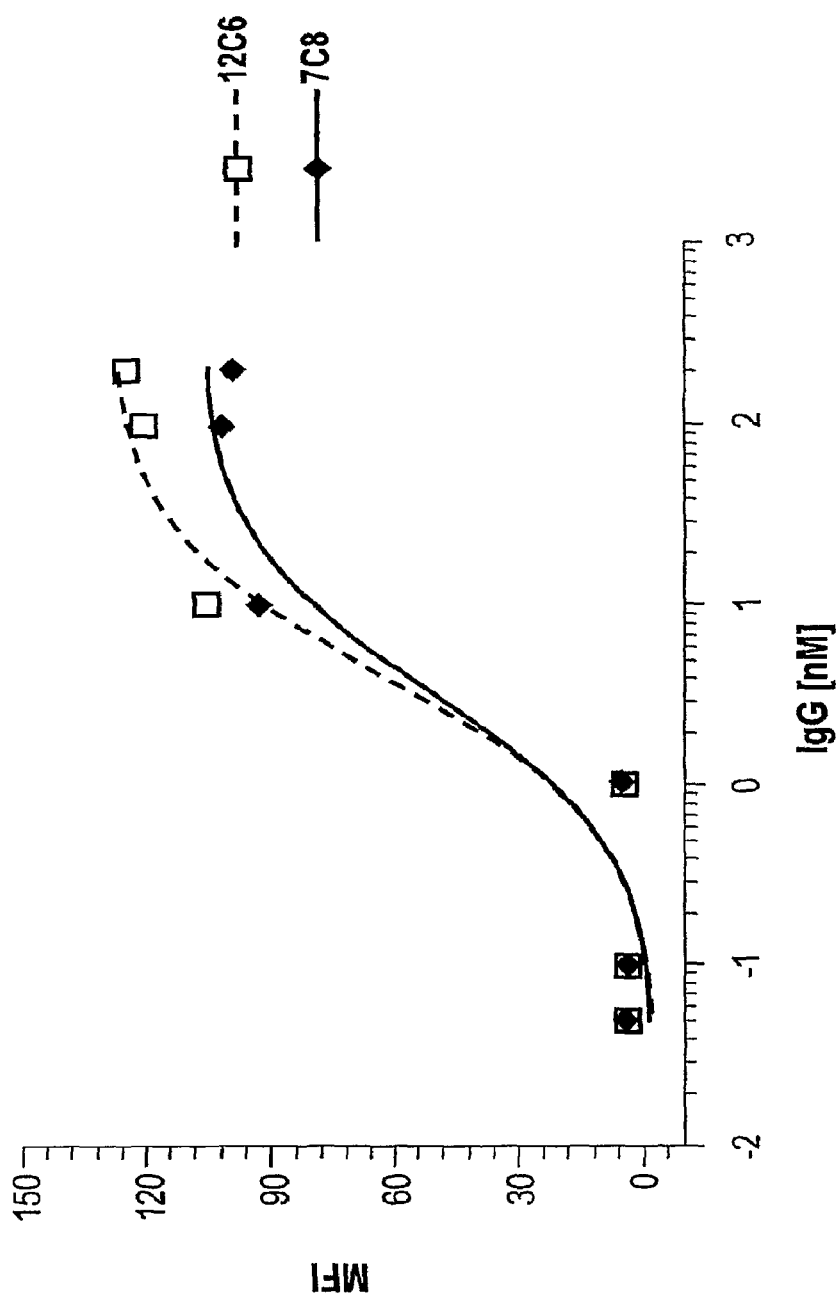
FIG. 16 shows the results of flow cytometry experiments demonstrating that antibodies directed against human PTK7 binds the cell surface of Wilms' tumor cells.

Characterization of Anti-PTK7 Antibody Binding to PTK7 Expressed on the Surface of Human Cancer Cells The nephroblastoma Wilms' tumor cell line G-401 (ATCC Acc No. CRL-1441) was tested for binding of the HuMAb anti-PTK7 human monoclonal antibodies 12C6 and 7C8 at different concentrations. Binding of the anti-PTK7 human monoclonal antibodies was assessed by incubating $1 \times 10^5$ cells with antibody at a starting concentration of 30 µg/ml and serially diluting the antibody at a 1:10 dilution. The cells were washed and binding was detected with a PE-labeled anti-human IgG Ab. Flow cytometric analyses were performed using a FACScan flow cytometry (Becton Dickinson, San Jose, Calif.). The results are shown in FIG. 16. The anti-PTK7 monoclonal antibodies 12C6 and 7C8 bound to the nephroblastoma Wilms' tumor cell line in a concentration dependent manner, as measured by the mean fluorescent intensity (MFI) of staining. The $EC_{50}$ values for the anti-PTK7 monoclonal antibodies 12C6 and 7C8 was 4.035 nM and 3.428 nM, respectively.

These data demonstrate that the anti-PTK7 HuMAbs bind to kidney cancer cell lines.

Example 6

Binding of Human Anti-PTK7 Antibody to Cancer Cell Lines

Anti-PTK7 antibodies were tested for binding to a variety of cancer cell lines by flow cytometry.

Figure 17:
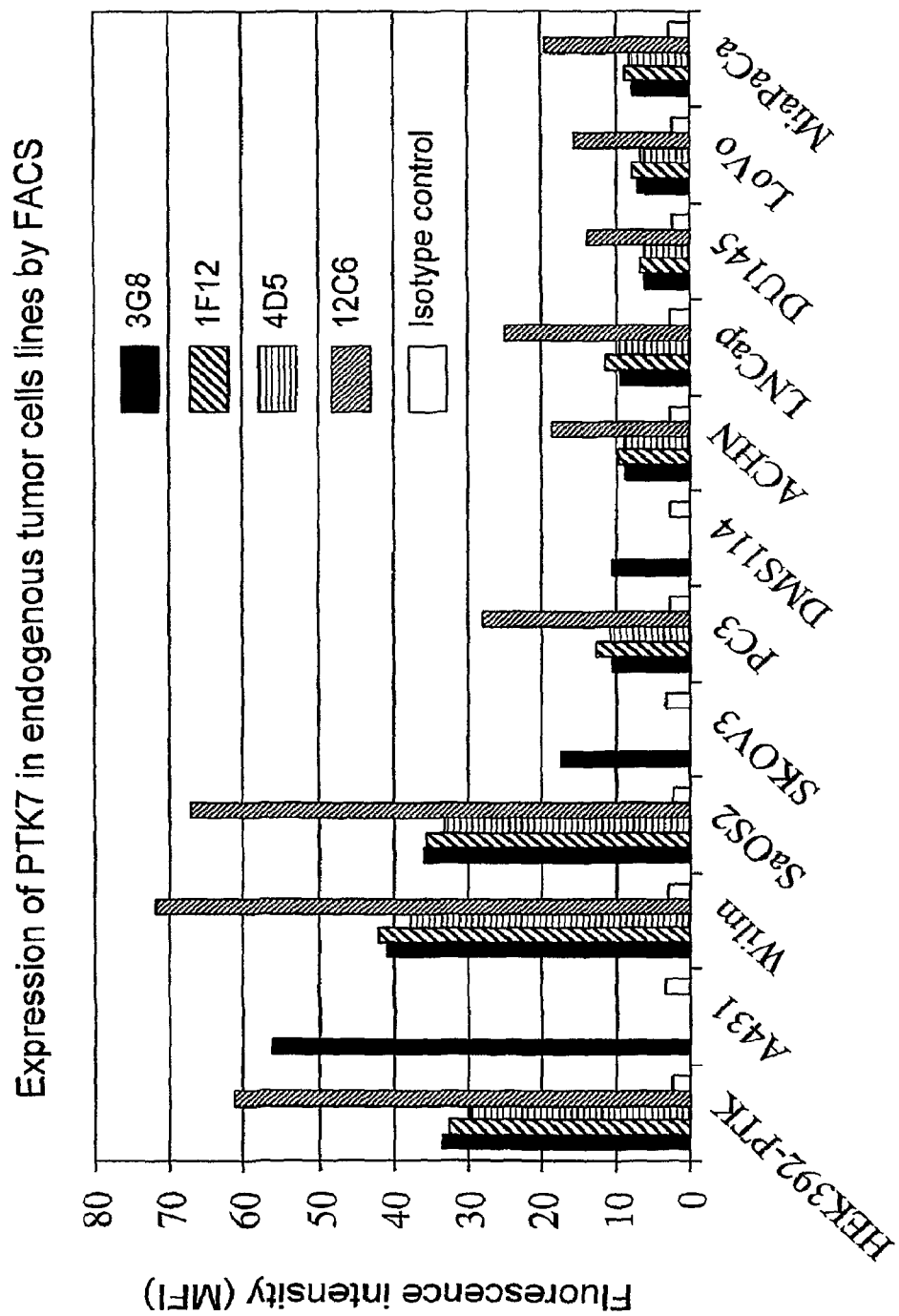
FIG. 17 shows the results of flow cytometry experiments demonstrating that antibodies directed against human PTK7 binds the cell surface of a variety of cancer cell lines.

Binding of the 3G8, 12C6a, 4D5 and 12C6 anti-PTK7 human monoclonal antibodies to a panel of cancer cell lines was assessed by incubating cancer cell lines with anti-PTK7 human monoclonal antibodies at a concentration of 10 µg/ml. The cancer cell lines that were tested were A-431 (ATCC Acc No. CRL-1555), Wilms tumor cells G-401 (ATCC Acc No. CRL-1441), Saos-2 (ATCC Acc No. HTB-85), SKOV-3 (ATCC Acc No. HTB-77), PC3 (ATCC Acc No. CRL-1435), DMS114 (ATCC Acc No. CRL-2066), ACHN (ATCC Acc No. CRL-1611), LNCaP (ATCC Acc No. CRL-1740), DU 145 (ATCC Acc No. HTB-81), LoVo (ATCC Acc No. CCL-229) and MIA PaCa-2 (ATCC Acc No. CRL-1420). An isotype control antibody was used as a negative control. The cells were washed and binding was detected with a FITC-labeled anti-human IgG Ab. Flow cytometric analyses were performed using a FACScan flow cytometry (Becton Dickinson, San Jose, Calif.). The results are shown in FIG. 17. The anti-PTK7 monoclonal antibodies 3G8, 12C6a, 4D5 and 12C6 bound to the cancer cell lines A-431, Wilms tumor cells G-401, Saos-2, SKOV-3, PC3, DMS114, ACHN, LNCaP, DU 145, LoVo and MIA PaCa-2, as measured by the mean fluorescent intensity (MFI) of staining. These data demonstrate that the anti-PTK7 HuMAbs bind to a range of cancer cells that express cell surface PTK7.

Example 7

Binding of Anti-PTK7 to Human T, B and Dendritic Cells

Anti-PTK7 antibodies were tested for binding to CD4+, CD8+ T-cells, CD19+ B-cells and human blood myeloid dendritic cells expressing PTK7 on their cell surface by flow cytometry.

Figure 18:
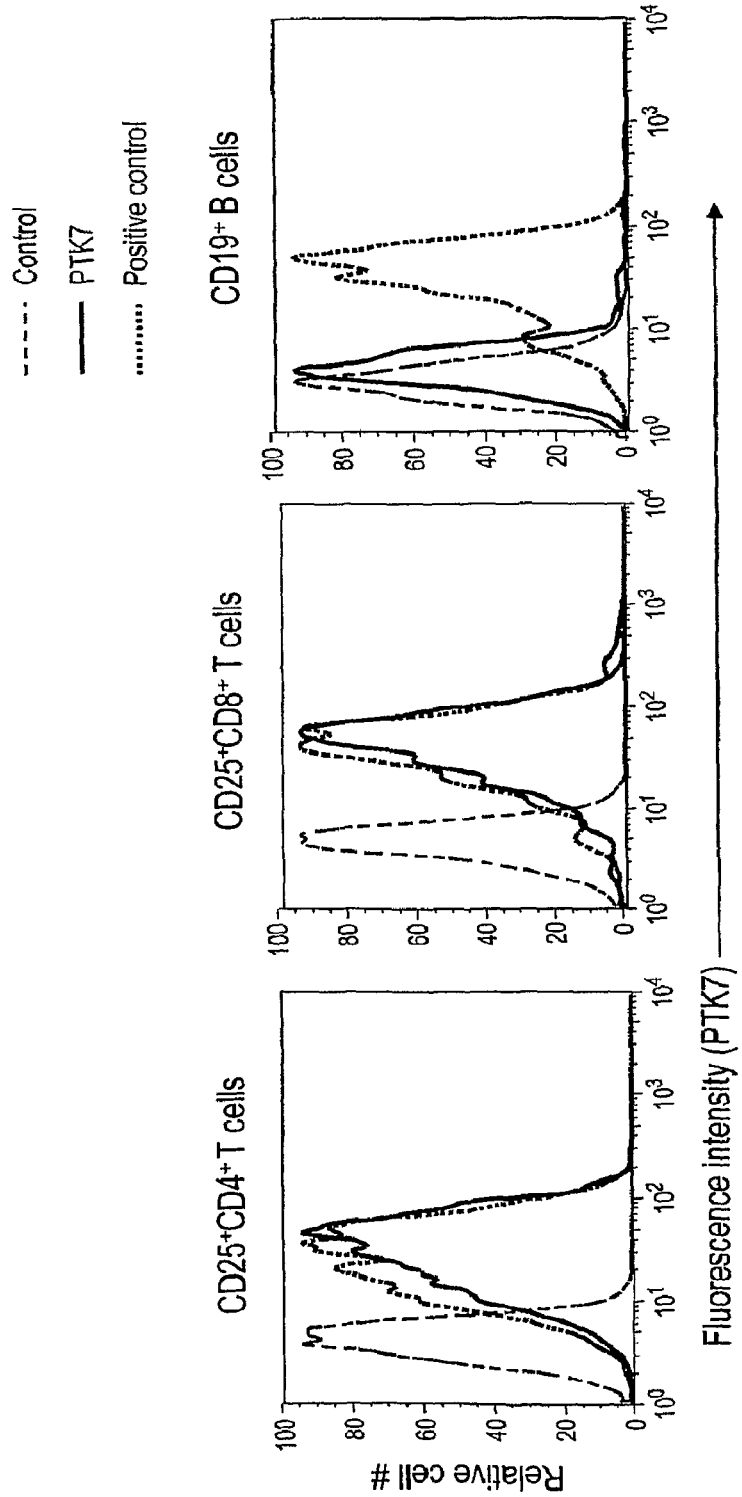
FIG. 18 shows the results of flow cytometry experiments demonstrating that antibodies directed against human PTK7 binds the cell surface of dendritic cells.
Figure 19:
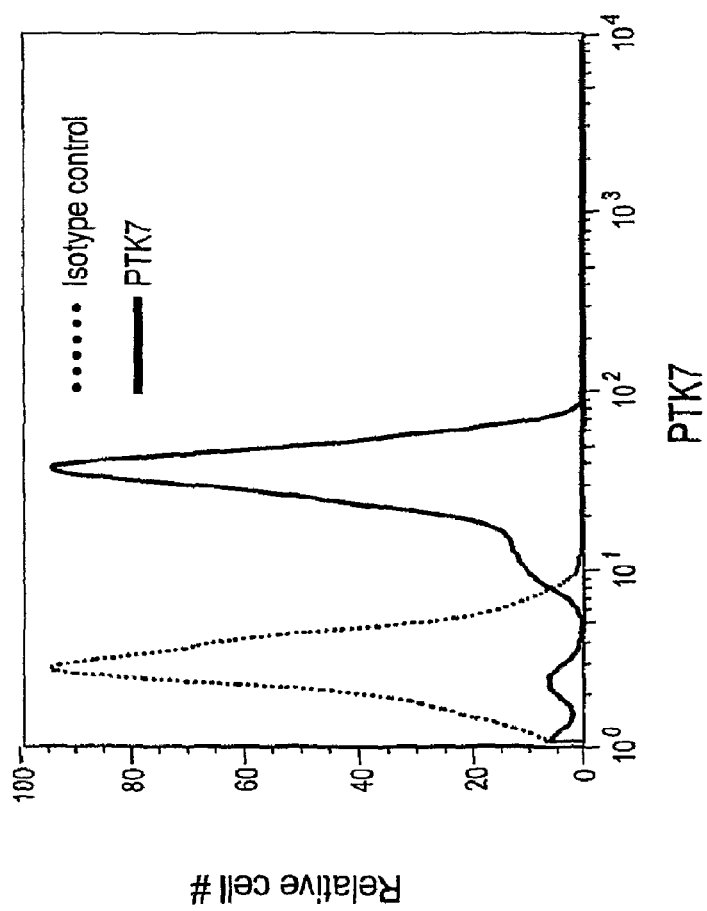
FIG. 19 shows the results of flow cytometry experiments demonstrating that antibodies directed against human PTK7 bind to CD4+ and CD8+ T-lymphocytes, but not to B-lymphocytes.
Figure 20A:
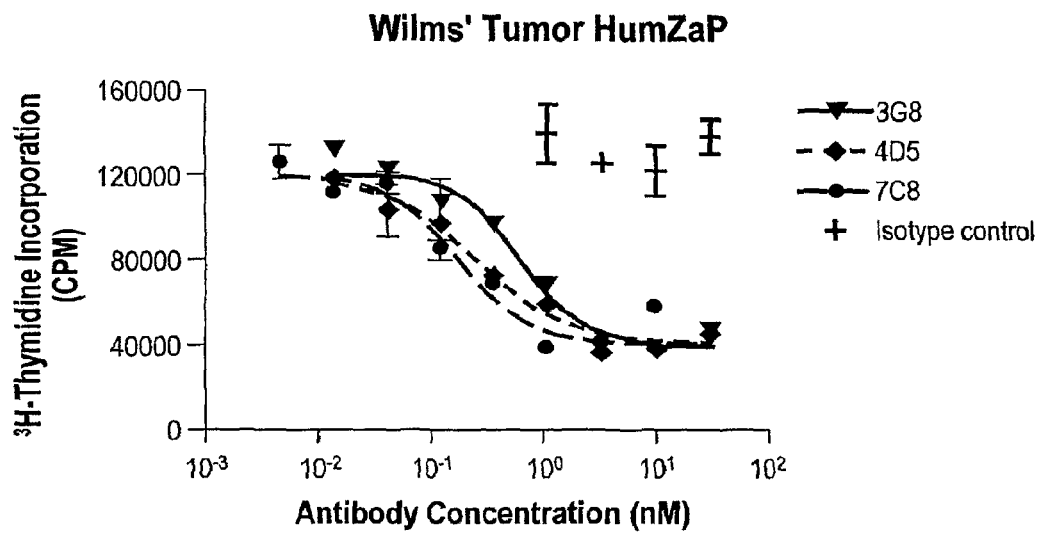
FIG. 20 shows the results of Hum-Zap internalization experiments demonstrating that human monoclonal antibodies against human PTK7 can internalize into PTK7+ cells. (A) Internalization of the human antibodies 3G8, 4D5 and 7C8 into Wilms' tumor cells. (B) Internalization of the human antibody 12C6 into Wilms' tumor cells. (C) Internalization of the human antibodies 7C8 and 12C6 into A-431 tumor cells. (D) Internalization of the human antibodies 7C8 and 12C6 into PC3 tumor cells.
Figure 20B:
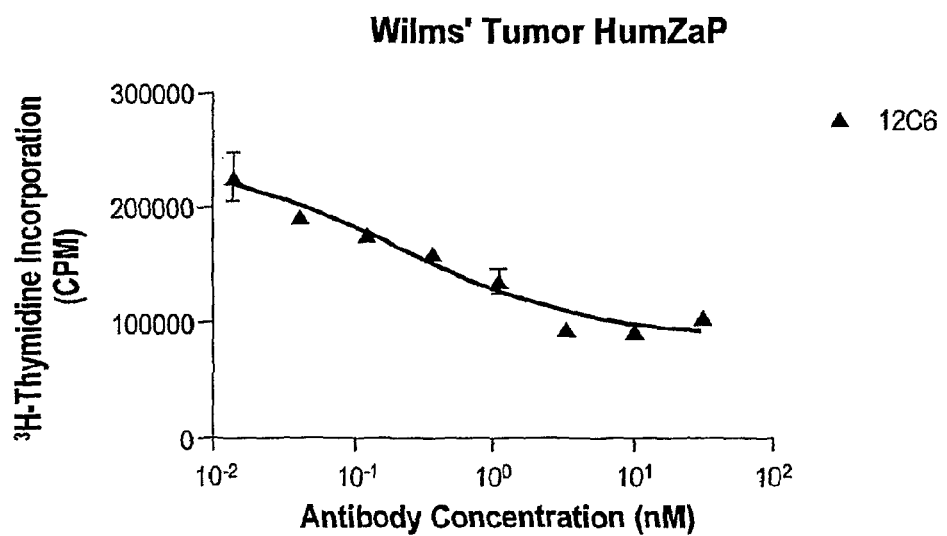
Figure 20C:
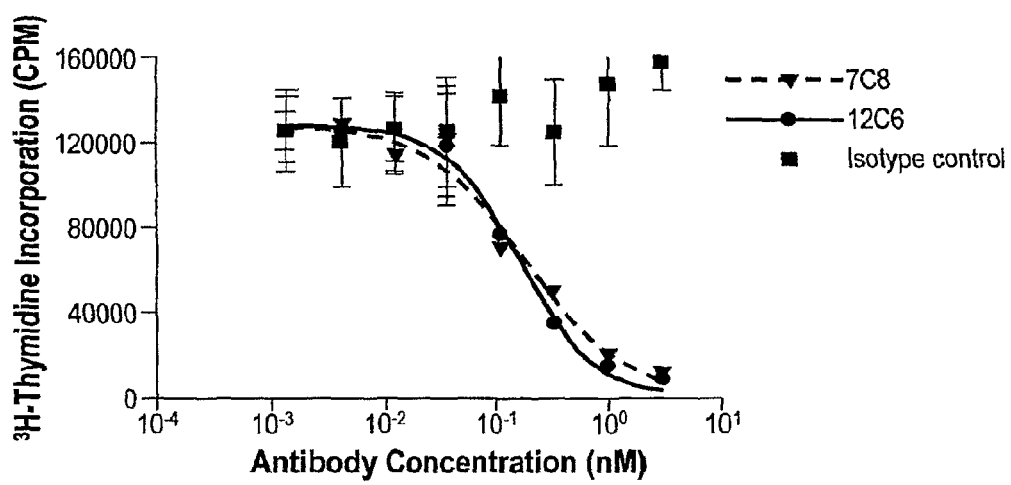
Figure 20D:
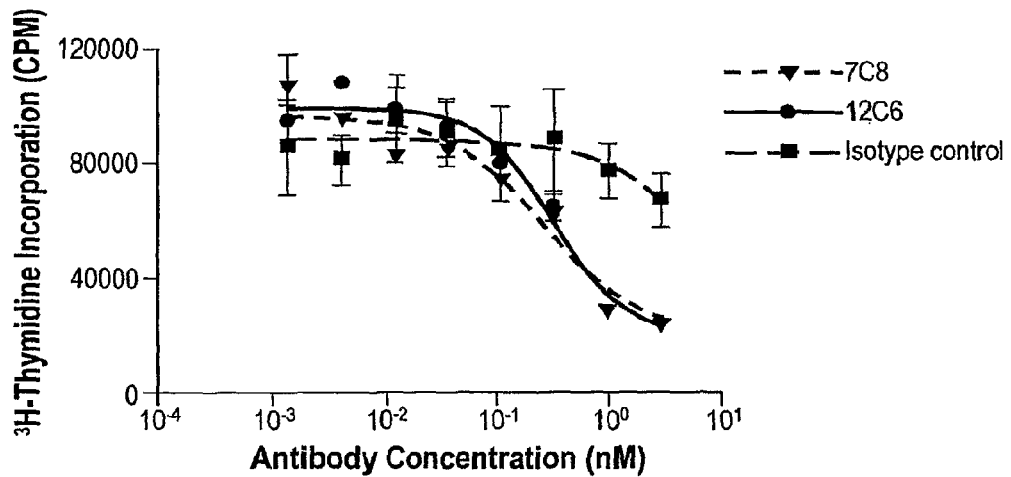

Human T cells were activated by anti-CD3 antibody to induce PTK7 expression on T cells prior to binding with a human anti-PTK7 monoclonal antibody. Binding of the 7c8 anti-PTK7 human monoclonal antibody was assessed by incubating the cells with anti-PTK7 human monoclonal antibodies at a concentration of 10 µg/ml. In some experiments, a known antibody that binds a T and B-cell specific marker was used as a positive control. The cells were washed and binding was detected with a FITC-labeled anti-human IgG Ab. Flow cytometric analyses were performed using a FACScan flow cytometry (Becton Dickinson, San Jose, Calif.). The results are shown in FIGS. 18 (activated human T cells and B-cells) and 19 (dendritic cells). The anti-PTK7 monoclonal antibody 7C8 bound to activated human CD4+ and CD8+ T cells and dendritic cells, but not to B-cells, as measured by the mean fluorescent intensity (MFI) of staining. These data demonstrate that the anti-PTK7 HuMAbs bind to human T-cells and dendritic cells.

Example 8

Internalization of Anti-PTK7 Monoclonal Antibody

Anti-PTK7 HuMAbs were tested for the ability to internalize into PTK7-expressing cell lines using a Hum-Zap internalization assay. The Hum-Zap assay tests for internalization of a primary human antibody through binding of a secondary antibody with affinity for human IgG conjugated to the toxin saporin.

The PTK7-expressing cancer cell lines Wilms tumor G-401 (ATCC Acc No. CRL-1441), A431 (ATCC Acc No. CRL-1555) and PC3 (ATCC Acc No. CRL-1435) were seeded at $1\times10^4$ cells/well in 100 µl wells directly. The anti-PTK7 HuMAb antibodies 3G8, 4D5, 12C6 or 7C8 were added to the wells at a starting concentration of 30 nM and titrated down at 1:3 serial dilutions. An isotype control antibody that is non-specific for PTK7 was used as a negative control. The Hum-Zap (Advanced Targeting Systems, San Diego, Calif., IT-22-25) was added at a concentration of 11 nM and plates were allowed to incubate for 72 hours. The plates were then pulsed with 1.0 µCi of $^3$H-thymidine for 24 hours, harvested and read in a Top Count Scintillation Counter (Packard Instruments, Meriden, Conn.). The results are shown in FIGS. 20A-D. The anti-PTK7 antibodies 3G8, 4D5, 12C6 and 7C8 showed an antibody concentration dependent decrease in $^3$H-thymidine incorporation in the PTK7-expressing Wilms' Tumor cancer cell line. The anti-PTK7 antibodies 12C6 and 7C8 showed an antibody concentration dependent decrease in $^3$H-thymidine incorporation in the PTK7-expressing cancer cell lines A-431 and PC3. The $EC_{50}$ value for the anti-PTK7 antibodies 3G8, 4D5, 12C6 and 7CS in Wilms' tumor cells was 0.6437 nM, 0.2516 nM, 0.2053 nM and 0.1788 nM, respectively. The $EC_{50}$ value for the anti-PTK7 antibodies 12C6 and 7C8 in A-431 cells was 0.1657 nM and 0.1826 nM, respectively. The $EC_{50}$ value for the anti-PTK7 antibodies 12C6 and 7C8 in PC3 tumor cells was 0.3175 nM and 0.2648 nM, respectively. This data demonstrates that the anti-PTK7 antibodies 3G8, 4D5, 12C6 and 7C8 internalize into cancer cells.

Example 9

Assessment of Cell Killing of a Toxin-Conjugated Anti-PTK7 Antibody on Human Cancer Cell Lines In this example, anti-PTK7 monoclonal antibodies conjugated to a toxin were tested for the ability to kill PTK7+ human cancer cell lines in a cell proliferation assay.

Figure 21:
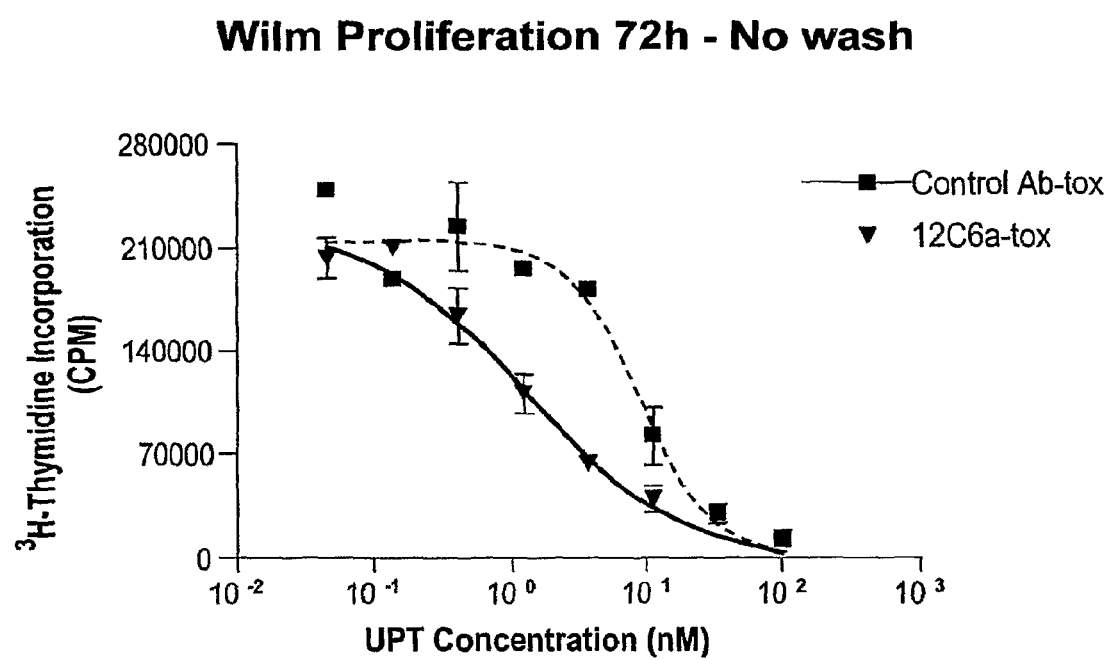
FIG. 21 shows the results of a cell proliferation assay demonstrating that toxin-conjugated human monoclonal anti-PTK7 antibodies kill human kidney cancer cell lines.

The anti-PTK7 HuMAb antibody 12C6a was conjugated to a toxin via a linker, such as a peptidyl, hydrazone or disulfide linker. Examples of toxin compounds that may be conjugated to the antibodies of the current invention are described in U.S. patent application Ser. No. 12/088,066 (published as US2008/0279868). The PTK7-expressing Wilms' tumor human kidney cancer cell line G-401 (ATCC Acc No. CRL-1441) was seeded at $10^4$ cells/well in 100 µl wells for 3 hours. An anti-PTK7 antibody-toxin conjugate was added to the wells at a starting concentration of 100 nM and titrated down at 1:3 serial dilutions. Plates were allowed to incubate for 48 hours. The plates were then pulsed with 1 µCi of $^3$H-thymidine for 24 hours before termination of the culture, harvested and read in a Top Count Scintillation Counter (Packard Instruments). FIG. 21 shows the effects of the 12C6a-conjugate on the Wilms' tumor cells. The anti-PTK7 antibody 12C6a showed an antibody-toxin concentration dependent decrease in $^3$H-thymidine incorporation in PTK7-expressing Wilms' tumor human kidney cancer cell line.

This data demonstrates that anti-PTK7 antibodies conjugated to toxin show specific cytotoxicity to human kidney cancer cells.

Example 10

Assessment of Cell Killing of a Toxin-Conjugated Anti-PTK7 Antibody on Human Tumor Cell Lines In this example, anti-PTK7 monoclonal antibodies conjugated to a toxin were tested for the ability to kill PTK7+ human tumor cell lines having either low, intermediate or high cell surface expression of PTK7 in a cell proliferation assay.

Figure 22:
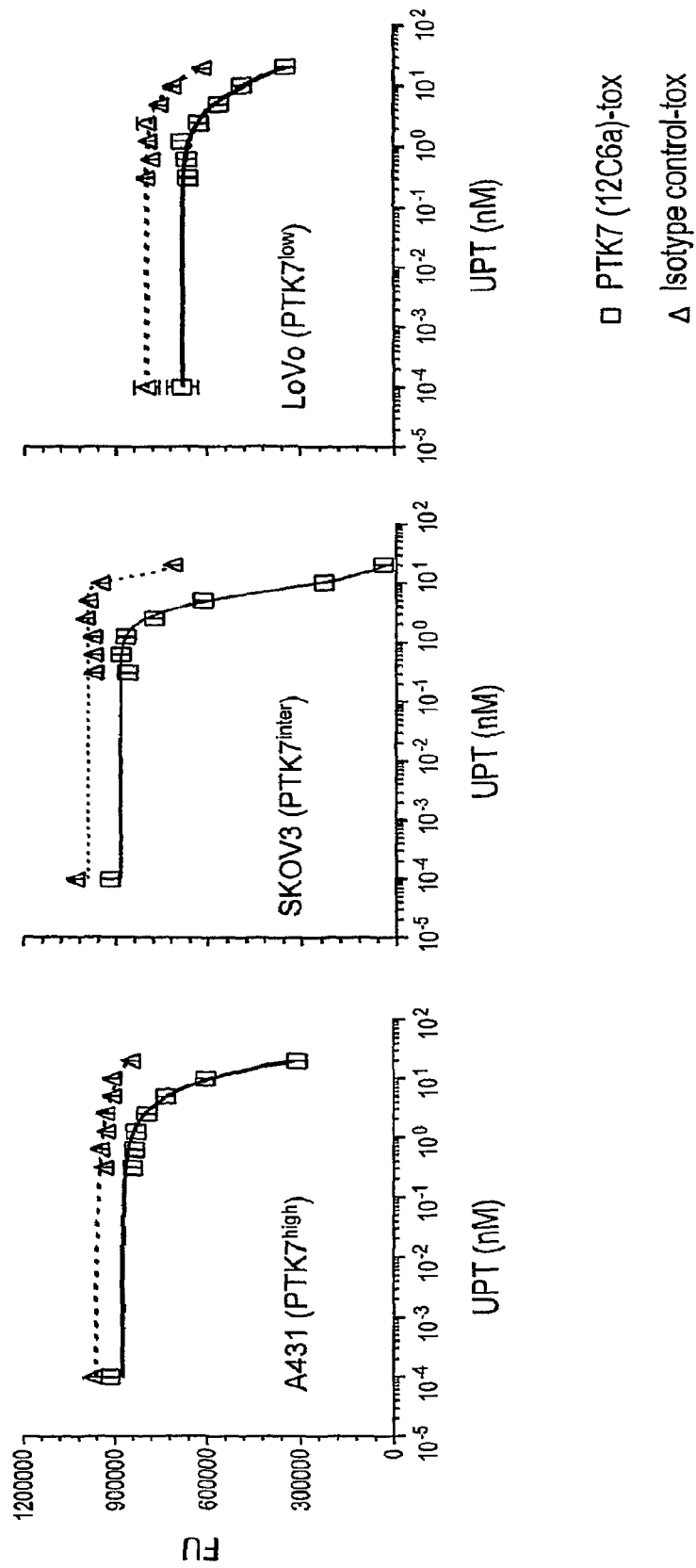
FIG. 22 shows the results of a cell proliferation assay demonstrating that toxin-conjugated human monoclonal anti-PTK7 antibodies kill cell lines expressing low to high levels of PTK7 expression.

The anti-PTK7 HuMAb antibody 12C6a was conjugated to a toxin via a linker, such as a peptidyl, hydrazone or disulfide linker. Examples of toxin compounds that may be conjugated to the antibodies of the current invention are described in U.S. patent application Ser. No. 12/088,066 (published as US2008/0279868). The PTK7-expressing human tumor cancer cell lines A-431, SKOV3, and LoVo were seeded at $10^4$ cells/well in 100 µl wells. The cell lines were previously tested for cell surface expression of PTK7 in a standard FACS assay. The A-431 cell line expressed the highest level of PTK7 cell surface expression and the LoVo cell line expressed the lowest level of PTK7 cell surface expression. An anti-PTK7 antibody-toxin conjugate was added to the wells at a starting concentration of 20 nM and titrated down at 1:2 serial dilutions. An isotype control antibody was used as a negative control. Plates were allowed to incubate for 3 hours and the unbound (free) antibody-toxin conjugates were washed out. The plates continued to incubate for 96 hrs and the killing activity (FU, fluorescent unit) was measured by cell viability in CellTiter-Glo® Luminescent assay according to protocol (Promega, Wis., USA, Technical bulletin No. 288) using a BIO-TEK reader (Bio-Tek Instruments, Inc, Vt., USA). The results are shown in FIG. 22. The anti-PTK7-toxin conjugate showed an antibody-toxin concentration dependent decrease in the proliferation assay in PTK7-expressing $A431^{high}$, $SKOV3^{inter}$, and $LoVo^{low}$.

This data demonstrates that anti-PTK7 antibodies conjugated to toxin show specific cytotoxicity to various human cancer cells.

Example 11

Immunohistochemistry with 3G8, 12C6a, 2E11

The ability of the anti-PTK7 HuMAbs 3G8, 12C6a, and 2E11 to recognize PTK7 by immunohistochemistry was examined using clinical biopsies from lung cancer, breast cancer, bladder cancer, pancreatic cancer, colon cancer, ovarian cancer, small intestine cancer & prostate cancer.

For immunohistochemistry, 5 µm frozen sections were used (Ardais Inc, USA). After drying for 30 minutes, sections were fixed with acetone (at room temperature for 10 minutes) and air-dried for 5 minutes. Slides were rinsed in PBS and then pre-incubated with 10% normal goat serum in PBS for 20 min and subsequently incubated with 10 µg/ml fitcylated antibody in PBS with 10% normal goat serum for 30 min at room temperature. Next, slides were washed three times with PBS and incubated for 30 min with mouse anti-FITC (10 µg/ml DAKO) at room temperature. Slides were washed again with PBS and incubated with Goat anti-mouse HRP conjugate (DAKO) for 30 minutes at room temperature. Slides were washed again 3× with PBS. Diaminobenzidine (Sigma) was used as substrate, resulting in brown staining. After washing with distilled water, slides were counterstained with hematoxyllin for 1 min. Subsequently, slides were washed for 10 secs in running distilled water and mounted in glycergel (DAKO) Clinical biopsy immunohistochemical staining displayed positive staining in the lung cancer, breast cancer, bladder cancer, pancreatic cancer, colon cancer, ovarian cancer, small intestine cancer & prostate cancer sections. Normal tissue was always negative for PTK7 staining whereas within malignant tissue, both cancer activated fibroblasts and cancerous epithelial cells were observed to be positive for PTK7 staining. The identity of the cancer activated fibroblasts was confirmed in bladder cancer and breast cancer sections by staining with a Fibroblast Activation Protein antibody (FAP, Alexis Biochemicals, San Diego, USA). FAP is a known marker of cancer activated fibroblasts (Hofheinz et al. (2003) *Oncologie* 26:44-48).

Example 12

Invasion Assay

Figure 23:
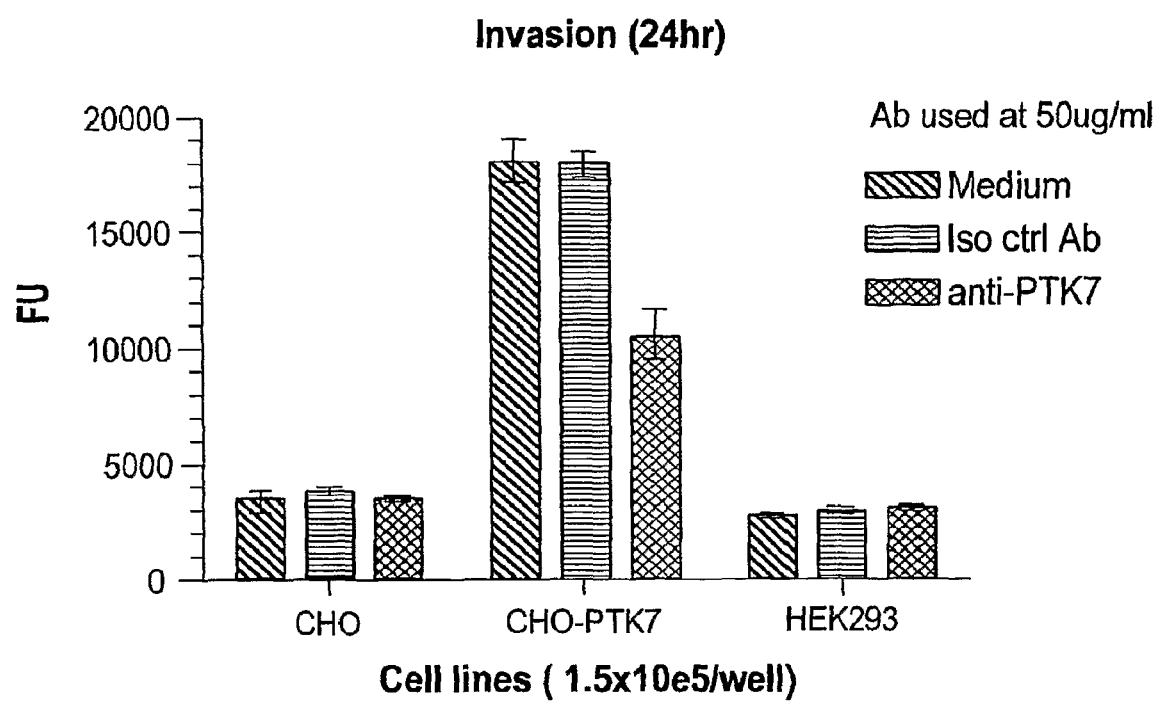
FIG. 23 shows the results of an invasion assay demonstrating that anti-PTK7 antibodies inhibit the invasion mobility of cells expressing PTK7 on the cell surface.

In this example, antibodies directed against PTK7 were tested for the ability to affect cell invasion in a CHO cell line transfected with PTK7.
The assay was done using a HTS 96-Multiwell Insert System (Cat#351162, BD Biosciences, Calif.) according to the protocol. Either a CHO parent cell line, CHO cells transfected with full-length PTK7 or a control HEK293 cell line were mixed with either a pool of antiPTK7 HuMabs or an isotype control antibody prior to the addition of the cells into the inserts. The mixture (cells+Ab pool) was added into an insert well in the invasion plate. Following incubation at 37° C. with 5% $CO_2$ for 24 hours, the cells were labeled with a fluorescent dye and cells that invaded to the bottom of the membrane were quantitated using a fluorescence plate reader. The results are shown in FIG. 23. This data demonstrates that anti-PTK7 antibodies inhibit the invasion mobility of cells expressing PTK7 on the cell surface.

Example 13

Treatment of In Vivo Pancreatic Cancer Cell Xenograft Model using Naked and Cytotoxin-Conjugated Anti-PTK7 Antibodies This Example discloses the in vivo treatment of mice implanted with a pancreatic cell carcinoma tumor with toxin-conjugated anti-PTK7 antibodies to examine the in vivo effect of the antibodies on tumor growth.

Figure 24:
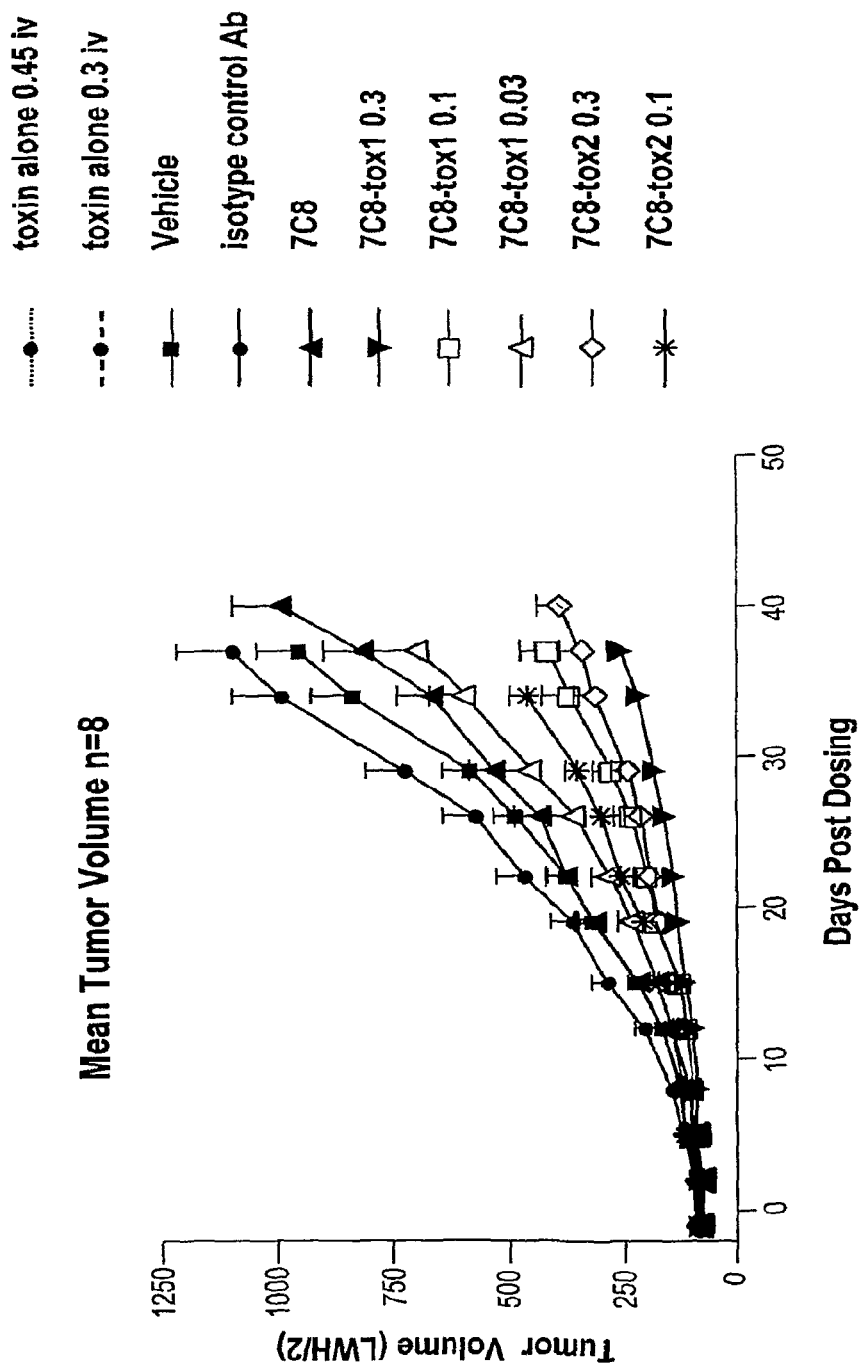
FIG. 24 shows the results of an in vivo tumor xenograft study demonstrating that anti-PTK7 antibodies conjugated to a toxin slowed tumor growth progression in pancreatic cancer.

HPAC (human pancreatic adenocarcinoma, ATCC Accession Number CRL-2119) or other suitable pancreatic cancer cells were expanded in vitro using standard laboratory procedures. Male Ncr athymic nude mice (Taconic, Hudson, N.Y.) between 6-8 weeks of age were implanted subcutaneously in the right flank with $2.5 \times 10^6$ HPAC cells in 0.2 ml of PBS/Matrigel (1:1) per mouse. Mice were weighed and measured for tumors three dimensionally using an electronic caliper twice weekly after implantation. Tumor volumes were calculated as height×width×length/2. Mice with HPAC tumors averaging 90 $mm^3$ were randomized into treatment groups. The mice were administered a single intravenous dose with PBS vehicle, naked anti-PTK7 antibody or toxin-conjugated anti-PTK7 HuMAb on Day 0 at the dosage indicated (µmol/kg). Examples of toxin compounds that may be conjugated to the antibodies of the current invention were described in the pending U.S. patent application Ser. No. 11/134,826 and the pending U.S. patent application designated MEDX-0034US4. Mice were monitored for tumor growth for 61 days post dosing. Mice were euthanized when the tumors reached tumor end point (2000 $mm^3$) or ulcerated. Anti-PTK7 antibodies conjugated to a toxin slowed tumor growth progression. The results are shown in FIG. 24. The anti-tumor effect of the anti-PTK7 toxin conjugate was dose dependent, with the greatest effect seen at a dose of 0.3 µmol/kg. Treatment with anti-PTK7 toxin conjugate was well tolerated, with subjects never experiencing greater than 5% median body weight loss (data not shown). Thus, treatment with an anti-PTK7 antibody-toxin conjugate has a direct in vivo inhibitory effect on pancreatic cancer tumor growth.

Example 14

Treatment of In Vivo Breast Cancer Cell Xenograft Model Using Naked and Cytotoxin-Conjugated Anti-PTK7 Antibodies This Example discloses the in vivo treatment of mice implanted with an adriamycin resistance breast carcinoma tumor with toxin-conjugated anti-PTK7 antibodies to examine the in vivo effect of the antibodies on tumor growth.

Figure 25:
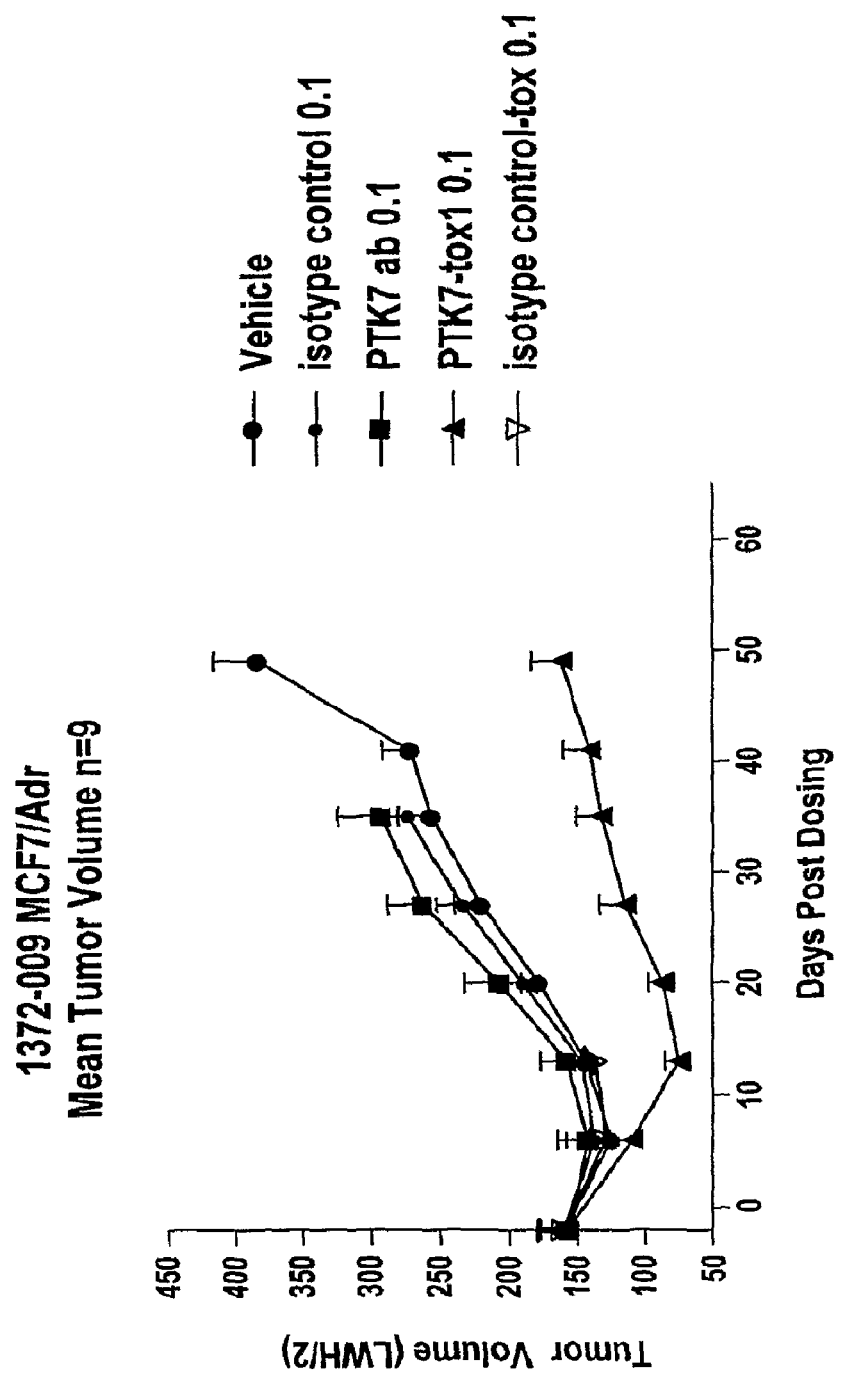
FIG. 25 shows the results of an in vivo tumor xenograft study demonstrating that anti-PTK7 antibodies conjugated to a toxin slowed tumor growth progression in breast cancer.

MCF7-adr (human breast cancer cell line resistant to adriamycin) were expanded in vitro using standard laboratory procedures. Female CB17.SCID mice (Taconic, Hudson, N.Y.) between 6-8 weeks of age were implanted subcutaneously with 1.7 mg 90-day release estrogen pellets, 3.0 mm size (Innovative Research of America, Sarasota, Fla.) at the neck region one day prior to being implanted subcutaneously in the right flank with $10 \times 10^6$ MCF7-Adr cells in 0.2 ml of PBS/Matrigel (1:1) per mouse. Mice were weighed and measured for tumors three dimensionally using an electronic caliper twice weekly after implantation. Tumor volumes were calculated as height×width×length/2. Mice with MCF7-adr tumors averaging 160 $mm^3$ were randomized into treatment groups. The mice were administered a single intravenous dose at 0.1 µmol/kg with PBS vehicle, naked anti-PTK7 antibody or toxin-conjugated anti-PTK7 HuMAb on Day 0. Examples of toxin compounds that may be conjugated to the antibodies of the current invention were described in the pending U.S. patent application Ser. No. 11/134,826 and the pending U.S. patent application designated MEDX-0034US4. Mice were monitored for tumor growth for 63 days post dosing. Mice were euthanized when the tumors were ulcerated. The results are shown in FIG. 25. Anti-PTK7 antibody toxin conjugates slowed tumor growth progression.

Thus, treatment with an anti-PTK7 antibody-toxin conjugate has a direct in vivo inhibitory effect on breast cancer tumor growth.

| SEQ ID NO: | SEQUENCE |
|---|---|
| 1 | VH a.a. 3G8, 3G8a |
| 2 | VH a.a. 4D5 |
| 3 | VH a.a. 12C6, 12C6a |
| 4 | VH a.a. 7C8 |
| 5 | VK a.a. 3G8 |
| 6 | VK a.a. 3G8a |
| 7 | VK a.a. 4D5 |
| 8 | VK a.a. 12C6 |
| 9 | VK a.a. 12C6a |
| 10 | VK a.a. 7C8 |
| 11 | VH CDR1 a.a. 3G8 |
| 12 | VH CDR1 a.a. 4D5 |
| 13 | VH CDR1 a.a. 12C6 |
| 14 | VH CDR1 a.a. 7C8 |
| 15 | VH CDR2 a.a. 3G8 |
| 16 | VH CDR2 a.a. 4D5 |
| 17 | VH CDR2 a.a. 12C6 |
| 18 | VH CDR2 a.a. 7C8 |
| 19 | VH CDR3 a.a. 3G8 |
| 20 | VH CDR3 a.a. 4D5 |
| 21 | VH CDR3 a.a. 12C6 |
| 22 | VH CDR3 a.a. 7C8 |
| 23 | VK CDR1 a.a. 3G8 |
| 24 | VK CDR1 a.a. 3G8a |
| 25 | VK CDR1 a.a. 4D5 |
| 26 | VK CDR1 a.a. 12C6 |
| 27 | VK CDR1 a.a. 12C6a |
| 28 | VK CDR1 a.a. 7C8 |
| 29 | VK CDR2 a.a. 3G8 |
| 30 | VK CDR2 a.a. 3G8a |
| 31 | VK CDR2 a.a. 4D5 |
| 32 | VK CDR2 a.a. 12C6 |
| 33 | VK CDR2 a.a. 12C6a |
| 34 | VK CDR2 a.a. 7C8 |
| 35 | VK CDR3 a.a. 3G8 |
| 36 | VK CDR3 a.a. 3G8a |
| 37 | VK CDR3 a.a. 4D5 |
| 38 | VK CDR3 a.a. 12C6 |
| 39 | VK CDR3 a.a. 12C6a |
| 40 | VK CDR3 a.a. 7C8 |
| 41 | VH n.t. 3G8, 3G8a |
| 42 | VH n.t. 4D5 |
| 43 | VH n.t. 12C6, 12C6a |
| 44 | VH n.t. 7C8 |
| 45 | VK n.t. 3G8 |
| 46 | VK n.t. 3G8a |
| 47 | VK n.t. 4D5 |
| 48 | VK n.t. 12C6 |
| 49 | VK n.t. 12C6a |
| 50 | VK n.t. 7C8 |
| 51 | VH 3-30.3 germline a.a. |
| 52 | VH DP44 germline a.a. |
| 53 | VH 3-33 germline a.a. |
| 54 | VK L15 germline a.a. |
| 55 | VK A10 germline a.a. |
| 56 | VK A27 germline a.a. |
| 57 | VK L6 germline a.a. |
| 58 | PTK7 a.a. |
| 59 | JH4b germline a.a |
| 60 | JH4b germline a.a. |
| 61 | 3-7 germline a.a. |
| 62 | 3-23 germline a.a. |
| 63 | JH4b germline a.a |
| 64 | JH6b germline a.a. |
| 65 | JK1 germline a.a. |
| 66 | JK5 germline a.a. |
| 67 | JK2 germline a.a. |
| 68 | JK2 germline a.a. |
| 69 | JK3 germline a.a. |

We claim:

1. An isolated monoclonal antibody, or an antigen-binding portion thereof, wherein the antibody specifically binds to human protein tyrosine kinase 7 (PTK7) and comprises a heavy chain variable region comprising the amino acid sequence of SEQ ID NO:2 and a light chain variable region comprising the amino acid sequence of SEQ ID NO:7.

2. An isolated monoclonal antibody, or an antigen-binding portion thereof, wherein the antibody competes for binding to human PTK7 with the antibody of claim 1.

3. An isolated monoclonal antibody, or an antigen-binding portion thereof, wherein the antibody specifically binds to human protein tyrosine kinase 7 (PTK7) and comprises a heavy chain and a light chain variable region, and wherein the heavy chain variable region comprises SEQ ID NO:2.

4. An isolated monoclonal antibody, or an antigen-binding portion thereof, wherein the antibody specifically binds to human protein tyrosine kinase 7 (PTK7) and comprises a heavy chain and a light chain variable region, and wherein the light chain variable region comprises SEQ ID NO:7.

5. An isolated monoclonal antibody, or an antigen-binding portion thereof, wherein the antibody specifically binds to human protein tyrosine kinase 7 (PTK7) and comprises:

a) a heavy chain variable region CDR1 comprising SEQ ID NO:12;
b) a heavy chain variable region CDR2 comprising SEQ ID NO:16;
c) a heavy chain variable region CDR3 comprising SEQ ID NO:20;
d) a light chain variable region CDR1 comprising SEQ ID NO:25;
e) a light chain variable region CDR2 comprising SEQ ID NO:31; and
f) a light chain variable region CDR3 comprising SEQ ID NO:37.

6. A composition comprising the antibody or antigen-binding portion thereof, of any one of claims 1 and 3-5, and a pharmaceutically acceptable carrier.

7. An immunoconjugate comprising the antibody or antigen-binding portion thereof, of any one of claims 1 and 3-5, linked to a therapeutic agent.

8. A composition comprising the immunoconjugate of claim 7 and a pharmaceutically acceptable carrier.

9. The immunoconjugate of claim 7, wherein the therapeutic agent is a cytotoxin or a radioactive isotype.

* * * * *

UNITED STATES PATENT AND TRADEMARK OFFICE
CERTIFICATE OF CORRECTION

| | | |
|---|---|---|
| PATENT NO. | : 8,222,375 B2 | Page 1 of 1 |
| APPLICATION NO. | : 12/095986 | |
| DATED | : July 17, 2012 | |
| INVENTOR(S) | : Jonathan Alexander Terrett et al. | |

It is certified that error appears in the above-identified patent and that said Letters Patent is hereby corrected as shown below:

In the claims, please replace "a cytotoxin or a radioactive isotype" in line 59 of column 102 with --a cytotoxin or a radioactive isotope--.

Signed and Sealed this
Eleventh Day of September, 2012

David J. Kappos
*Director of the United States Patent and Trademark Office*